United States Patent
Meade et al.

(10) Patent No.: US 10,786,582 B2
(45) Date of Patent: *Sep. 29, 2020

(54) GD(III)-DITHIOLANE GOLD NANOPARTICLE CONJUGATES

(71) Applicant: Northwestern University, Evanston, IL (US)

(72) Inventors: Thomas J. Meade, Willmette, IL (US); Matthew W. Rotz, Chicago, IL (US); Robert J. Holbrook, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/504,021

(22) Filed: Jul. 5, 2019

(65) Prior Publication Data

US 2019/0321492 A1 Oct. 24, 2019

Related U.S. Application Data

(63) Continuation of application No. 15/192,377, filed on Jun. 24, 2016, now Pat. No. 10,406,249.

(60) Provisional application No. 62/185,323, filed on Jun. 26, 2015.

(51) Int. Cl.
*A61K 49/08* (2006.01)
*A61K 49/18* (2006.01)

(52) U.S. Cl.
CPC ........ *A61K 49/085* (2013.01); *A61K 49/1878* (2013.01)

(58) Field of Classification Search
CPC .......................... A61K 49/1878; A61K 49/085
See application file for complete search history.

(56) References Cited

U.S. PATENT DOCUMENTS

| | | | |
|---|---|---|---|
| 2006/0222595 A1 | 10/2006 | Mukherjee et al. | |
| 2010/0260676 A1* | 10/2010 | Hanson | A61K 49/0002 424/9.1 |
| 2010/0291222 A1 | 11/2010 | Yu et al. | |
| 2014/0142253 A1 | 5/2014 | Srivastava et al. | |

FOREIGN PATENT DOCUMENTS

| | | |
|---|---|---|
| WO | WO93/06868 | 4/1993 |
| WO | WO94/08629 | 4/1994 |
| WO | WO94/09056 | 4/1994 |
| WO | WO96/26754 | 9/1996 |
| WO | WO2015/034925 | 3/2015 |

OTHER PUBLICATIONS

Park et al., Bioorg. Med. Chem. Lett., 2010, 20(7), p. 2287-91. (Year: 2010).*

Reberdiere et al., Tetrahedron Letters, 2012, 53, p. 6115-6118). (Year: 2012).*
Abbruzzese, The challenge of pancreatic cancer. Int J Gastrointest Cancer. 2003;33(1):1-2.
Alric et al., Gadolinium Chelate Coated Gold Nanoparticles as Contrast Agents for Both X-ray Computed Tomography and Magnetic Resonance Imaging. J Am Chem Soc. May 7, 2008;130(18):5908-15.
Arvizo et al., Modulating Pharmacokinetics, Tumor Uptake and Biodistribution by Engineered Nanoparticles. PLoS One. 2011;6(9):e24374.
Bellingan et al., Adhesion Molecule-dependent Mechanisms Regulate the Rate of Macrophage Clearance During the Resolution of Peritoneal Inflammation.J Exp Med. Dec. 2, 2002;196(11):1515-21.
Birchard et al., Suspected pancreatic cancer: evaluation by dynamic gadolinium-enhanced 3D gradient-echo MRI. AJR Am J Roentgenol. Sep. 2005;185(3):700-3.
Botsikas et al., Pancreatic magnetic resonance imaging after manganese injection distinguishes type 2 diabetic and normoglycemic patients. Islets. May-Jun. 2012;4(3):243-8.
Brust et. al., Synthesis of thiol-derivatized gold nanoparticles in a two-phase Liquid-Liquid system. J. Chem. Soc., Chem. Commun., 1994, 801-802.
Burda et al., Chemistry and Properties of Nanocrystals of Different Shapes. Chem Rev. Apr. 2005;105(4):1025-102.
Daniel et al., Gold nanoparticles: Assembly, Supramolecular Chemistry, Quantum-Size-Related Properties, and Applications toward Biology, Catalysis, and Nanotechnology. Chem Rev. Jan. 2004;104(1):293-346.
Dempsey et al., MRI safety review. Semin Ultrasound CT MR. Oct. 2002;23(5):392-401.
Diehl et al., MR imaging of pancreatic lesions. Comparison of manganese-DPDP and gadolinium chelate. Invest Radiol. Sep. 1999;34(9):589-95.
Ferreira et al., Gold nanoparticles functionalised with fast water exchanging Gd3+ chelates: linker effects on the relaxivity. Dalton Trans. Mar. 7, 2015;44(9):4016-31.
Grimm et al., Magnetic resonance imaging of the pancreas and pancreatic tumors in a mouse orthotopic model of human cancer. Int J Cancer. Sep. 20, 2003;106(5):806-11.
Harrison et al., Multimeric Near IR-MR Contrast Agent for Multimodal In Vivo Imaging. J Am Chem Soc. Jul. 22, 2015;137(28):9108-16.
Hidalgo et al., Addressing the challenges of pancreatic cancer: Future directions for improving outcomes. Pancreatology. Jan.-Feb. 2015;15(1):8-18.
Hung et al., Graphene Oxide Enhances Cellular Delivery of Hydrophilic Small Molecules by Co-incubation. ACS Nano. Oct. 28, 2014;8(10):10168-77.
Hung et al., Mechanisms of Gadographene-Mediated Proton Spin Relaxation. J Phys Chem C Nanomater Interfaces. Aug. 8, 2013;117(31).
Irure et al., Sugar/gadolinium-loaded gold nanoparticles for labelling and imaging cells by magnetic resonance imaging. Biomater. Sci. 2013;1:658-668.

(Continued)

*Primary Examiner* — Michael G. Hartley
*Assistant Examiner* — Leah H Schlientz
(74) *Attorney, Agent, or Firm* — Casimir Jones SC; David W. Staple

(57) ABSTRACT

Provided herein are compositions Gd(III)-dithiolane gold nanoparticle conjugates and methods of use thereof. In particular, compositions and method find use in in vivo imaging (e.g., magnetic resonance imaging (MRI)), for example, of pancreatic tissue.

14 Claims, 30 Drawing Sheets

Specification includes a Sequence Listing.

(56) References Cited

OTHER PUBLICATIONS

Jensen et al., Spherical Nucleic Acid Nanoparticle Conjugates as an RNAi-Based Therapy for Glioblastoma. Sci Transl Med. Oct. 30, 2013;5(209):209ra152.
Klein, Identifying people at a high risk of developing pancreatic cancer. Nat Rev Cancer. Jan. 2013;13(1):66-74.
Koh et al., Diffusion-Weighted MRI in the Body: Applications and Challenges in Oncology. AJR Am J Roentgenol. Jun. 2007;188(6):1622-35.
Lasagna-Reeves et al., Bioaccumulation and toxicity of gold nanoparticles after repeated administration in mice. Biochem Biophys Res Commun. Mar. 19, 2010;393(4):649-55.
Lee et al., Theranostic nanoparticles with controlled release of gemcitabine for targeted therapy and MRI of pancreatic cancer.ACS Nano. Mar. 26, 2013;7(3):2078-89.
Lewis et al., Lanthanide-coated gold nanoparticles for biomedical applications. Coord. Chem. Rev. 2014;273-274:213-225.
Miller et al., MRI of adenocarcinoma of the pancreas. AJR Am J Roentgenol. Oct. 2006;187(4):W365-74.
Park et al., Gold nanoparticles functionalised by Gd complex of DTPA-bis(amide) conjugate of glutathione as an MRI contrast agent. Bioorg Med Chem Lett. Dec. 1, 2008;18(23):6135-7.
Patra et al., Fabrication of gold nanoparticles for targeted therapy in pancreatic cancer. Adv Drug Deliv Rev. Mar. 8, 2010;62(3):346-61.
Patra et al., Targeted delivery of gemcitabine to pancreatic adenocarcinoma using cetuximab as a targeting agent. Cancer Res. Mar. 15, 2008;68(6):1970-8.
Rotz et al., High Relaxivity Gd(III)-DNA Gold Nanostars: Investigation of Shape Effects on Proton Relaxation. ACS Nano. Mar. 24, 2015;9(3):3385-96.
Sadauskas et al., Kupffer cells are central in the removal of nanoparticles from the organism. Part Fibre Toxicol. Oct. 19, 2007;4:10.
Schima, MRI of the pancreas: tumours and tumoursimulating processes. Cancer Imaging. Dec. 20, 2006;6:199-20.
Shellock et al., MRI Safety Update 2008: Part 1, MRI Contrast Agents and Nephrogenic Systemic Fibrosis. AJR Am J Roentgenol. Oct. 2008;191(4):1129-39.
Song et al., Multimodal Gadolinium-Enriched DNA-Gold Nanoparticle Conjugates for Cellular Imaging. Angew Chem Int Ed Engl. 2009;48(48):9143-7.
Strauch et al., Reporter Protein-Targeted Probes for Magnetic Resonance Imaging. J Am Chem Soc. Oct. 19, 2011;133(41):16346-9.
Sukerkar et al., A Steroid-Conjugated Magnetic Resonance Probe Enhances Contrast in Progesterone Receptor Expressing Organs and Tumors in Vivo. Mol Pharm. Aug. 1, 2011;8(4):1390-400.
Sung et al., Multimetallic Complexes and Functionalized Gold Nanoparticles Based on a Combination of d- and f-Elements. Inorg Chem. Feb. 17, 2014;53(4):1989-2005.
Templeton et al., Monolayer-Protected Cluster Molecules. ACC Chem Res. Jan. 2000;33(1):27-36.
Tomalia et al., Starburst Dendrimers: Molecular-Level Control of Size, Shape, Surface Chemistry, Topology, and Flexibility from Atoms to Macroscopic Matter, Agnew Chem Int Ed Engl 1990;29:138-175.
Torres et al., Preliminary results of MR imaging with superparamagnetic iron oxide in pancreatic and retroperitoneal disorders. Radiographics. Sep. 1991;11(5):785-91; discussion 792-3.
Tummala et al., Imaging of pancreatic cancer: An overview.J Gastrointest Oncol. Sep. 2011;2(3):168-74.
Willinek et al., Clinical advantages of 3.0 T MRI over 1.5 T. Eur J Radiol. Jan. 2008;65(1):2-14.
Zeng et al., Lipid-AuNPs@PDA Nanohybrid for MRI/CT Imaging and Photothermal Therapy of Hepatocellular Carcinoma. ACS Appl Mater Interfaces. Aug. 27, 2014;6(16):14266-77.
International Search Report and Written Opinion for PCT/US2016/039300, dated Sep. 19, 2016, 13 pages.

\* cited by examiner

Lip-DO3AGd

Lip-DTPAGd

SEQUENCE LISTING

<160> NUMBER OF SEQ ID NOS: 1

<210> SEQ ID NO 1
<211> LENGTH: 24
<212> TYPE: DNA
<213> ORGANISM: Artificial sequence
<220> FEATURE:
<223> OTHER INFORMATION: synthesized oligonucleotide

<400> SEQUENCE: 1
tttttttttt tttttttttt tttt                24

GD(III)-DITHIOLANE GOLD NANOPARTICLE CONJUGATES

CROSS REFERENCE TO RELATED APPLICATIONS

This invention is a continuation of U.S. patent application Ser. No. 15/192,377, filed Jun. 24, 2016, now allowed, which claims the priority benefit of U.S. Provisional Patent Application 62/185,323, filed Jun. 26, 2015, each of which is incorporated by reference in its entirety.

STATEMENT REGARDING FEDERALLY SPONSORED RESEARCH OR DEVELOPMENT

This invention was made with government support under U54 CA151880 awarded by the National Institutes of Health. The government has certain rights in the invention.

FIELD

Provided herein are compositions Gd(III)-dithiolane gold nanoparticle conjugates and methods of use thereof. In particular, compositions and method find use in in vivo imaging (e.g., magnetic resonance imaging (MRI)), for example, of pancreatic tissue.

BACKGROUND

Gold nanoparticles provide a robust platform for targeted delivery of therapeutics in research and medical applications. However, gold nanoparticle conjugates for biological and medical applications have severe limitations in in vivo experiments. Tracking the particles in vivo generally require sacrifice of the subject, which results in a loss of temporal resolution.

SUMMARY

Provided herein are compositions Gd(III)-dithiolane gold nanoparticle conjugates and methods of use thereof. In particular, compositions and method find use in in vivo imaging (e.g., magnetic resonance imaging (MRI)), for example, of pancreatic tissue.

In some embodiments, provided herein are systems using dithiolane-modified Gd(III) contrast agents that provide facile functionalization of gold nanoparticle platforms without additional chemical reagents. This allows users (e.g., researchers, clinicians, etc.) to, for example, take advantage of MRI's excellent spatial and temporal resolution for tracking gold nanoparticles.

In some embodiments, dithiolane-modified Gd(lll) contrast agents are functionalized onto gold nanoparticle surfaces through gold-thiol bond formation. In some embodiments, provided herein are gold nanoparticle conjugates that are functionalized with contrast agents that accumulate in pancreatic tissue of mice. This technology allows monitoring the progression of mouse pancreatic size in longitudinal studies through MRI without sacrifice of the subject (e.g., progression of pancreatic size in diabetic mouse models or tumor progression). Furthermore, gold nanoparticles, functionalized with targeting and therapeutic components, can be post-modified with contrast agents for tracking in MRI.

In some embodiments, compositions and methods herein find use in, for example, clinical diagnostics, theranostics, cell labeling for magnetic resonance imaging, etc. In some embodiments, superior cell uptake of the Gd(III)-modified gold particles herein allow for in vivo cell tracking applications.

In some embodiments, the gold nanoparticles functionalized with dithiolane-modified Gd(III) contrast agents, as described herein, accumulate in pancreatic tissue. This technology allows, for example, monitoring the progression of pancreatic size in longitudinal studies (e.g., progression of pancreatic size in diabetic models of tumor progression).

In some embodiments, small Gd(III) lipoic acid conjugates feature reagent-free AuNP conjugation (e.g., no reducing agent), which allows a facile post-conjugation addition of MR imaging capacity to synthesized AuNP constructs, such as DNA-AuNPs. Embodiments herein allow for facile addition of MRI contrast agents to pre-functionalized Au nanoparticle constructs. Such embodiments allow tracking of AuNPs in vivo using, for example, MRI.

In some embodiments, the nanoparticle conjugates described herein feature modular chelate/lipoic acid ligand synthesis, providing the capacity to complex other relevant biological metals such as radionuclides (e.g., $^{99m}$Tc (SPECT), $^{64}$Cu, $^{68}$Ga (PET)) with fast metalation kinetics and high thermodynamic stability constants, in addition to fast particle binding kinetics (e.g., hours, relative to days with salt aging, and neutral pH versus acidic pH for competing conjugation strategies).

In some embodiments, compositions and methods herein provide advantages of, for example: improved spatial resolution compared to PET, bioluminescence, CT, and ultrasound; improved temporal resolution versus histochemical staining, no T2 contrast (which darkens images), etc.

In some embodiments, Gd(III)-lipoic acid complexes are conjugated to AuNP surfaces presenting extremely high Gd(III) chelate loading on the particles surface, and greater particle stability in buffer and cell media, relative to Gd(III)-DNA-AuNP conjugates. In some embodiments, Gd(III) lipoic acid complexes are synthesized in a variety of forms, wherein the specific relaxometric and stability features of the Gd(III) complexes are optimized.

In some embodiments, methods herein feature a straightforward conjugation procedure with only mixing of purified Gd(III) lipoic acid conjugate to AuNP formulation with stirring (e.g., for 1-48 hours (e.g., 1, 2, 3, 4, 5, 6, 8, 12, 16, 20, 24 hours) and purification (e.g., by centrifugation (e.g. repeated centrifugation)), without other required reagents (e.g., no reducing agent required). In some embodiments, a 5-membered thiolane ring allows for conjugation chemistry to the AuNP surface without secondary reducing reagents.

In some embodiments, provided herein are compositions comprising: a chelated metal-ion contrast agent conjugated to a gold nanoparticle by a dithiolane linkage. In some embodiments, the metal ion is selected from the group consisting of Mn(II), Gd(III), Dy(III), Ho(III), Er(III), Eu(III), Tb(III), Sm(III), Ce(III), Pr(III), Yb(III), Tm(III), Nd(III), and Tb(IV). In some embodiments, the metal ion is Gd(III). In some embodiments, the metal ion is chelated by a chelation moiety selected from the group consisting of ethylenediaminetetraacetic acid (EDTA), diethylenetriaminepentaacetic acid (DTPA), 1,4,8,11-tetraazacyclododecane-1,4,8,11-tetraacetic acid (TETA), triethylene tetraamine hexaacetic acid (TTHA), 1,4,7,10-tetraazacyclododecane-1,4,7,10-tetraacetic acid (DOTA), TAGA, 1,4,7,10-tetraazacyclododecane-1,4,7,10-tetra (methylene phosphonic acid) (DOTP), diethylenetriaminepentaacetic acid (DTPA), 3,9-bis(methylcarbamoylmethyl)-3,6,9-triazaundecanedioic acid; N,N'-(Carboxymethyliminobisethylene)bis [N-

(methylcarbamoylmethyl)glycine]; N,N'-Bis[(methylcarbamoyl)methyl][N,N'-bis(carboxymethyl)[2,2'-(carboxymethylimino)bis(ethaneamine)]] (DTPA-BMA), 1,4,7,10-tetraazacyclododecane-1,7-bis(acetic acid) (DO2P), and 1,4,7-tris(carboxymethyl)-1,4,7,10-tetraazacyclododecane (DO3A). In some embodiments, the chelation moiety comprises DO3A. In some embodiments, the chelation moiety comprises DTPA. In some embodiments, the dithiolane linkage is the reaction product of a dithiolane functional group and the gold nanoparticle, and comprises two bonds between the sulfurs of the dithiolane functional group and the gold nanoparticle.

In some embodiments, compositions further comprise a linker moiety between the chelated metal-ion contrast agent and the dithiolane linkage. In some embodiments, the linker moiety comprises an alkyl chain, heteroalkyl chain, substituted alkyl chain, or substituted heteroalkyl chain. In some embodiments, the linker moiety comprises $(CH_2)_xCONH(CH_2)_y$, wherein x is 2-10 and y is 2-10. In some embodiments, the linker moiety comprises $(CH_2)_4CONH(CH_2)_6$. In some embodiments, the linker moiety and the dithiolane comprise lipoic acid. In some embodiments, the linker comprises a 1,2,3-triazole. In some embodiments, the linker comprises the reaction product of an azide and an alkyne.

In some embodiments, compositions do not comprise nucleic acid (e.g., no functional moieties linked to the gold nanoparticle by oligonucleotide linkers).

In some embodiments, the metal ion is selected from the list consisting of Mn(II), Gd(III), Dy(III), Ho(III), Er(III), Eu(III), Tb(III), Sm(III), Ce(III), Pr(III), Yb(III), Tm(III), Nd(III), and Tb(IV) coordinated by a chelation moiety selected from the list consisting of EDTA, DTPA, TTHA, DOTA, TAGA, DOTP, DTPA-BMA, DO2P, and DO3A, wherein the chelation moiety is linked to the gold nanoparticle by a linker moiety and a dithilane linkage. In some embodiments, the metal ion is Gd(III) and the chelation moiety is DTPA or DO3A.

In some embodiments, compositions further comprise a functional moiety linked to the gold nanoparticle by an oligonucleotide linker. In some embodiments, the oligonucleotide is linked to the gold nanoparticle by a terminal thiol on the oligonucleotide. In some embodiments, the oligonucleotide comprises a 3' thiol group for linkage to the gold nanoparticle. In some embodiments, the oligonucleotide comprises a 5' thiol group for linkage to the gold nanoparticle. In some embodiments, the functional moiety is to the 5' or 3' end of the oligonucleotide. In some embodiments, the functional moiety is a contrast agent, optically-detectable moiety, therapeutic agent, or targeting moiety. In some embodiments, the oligonucleotide comprises one or more modified nucleotides for attachment of the functional moiety. In some embodiments, the oligonucleotide comprises a terminal modified nucleotide for attachment of the functional moiety. In some embodiments, the oligonucleotide further comprises one or more internal modified nucleotides for attachment of additional functional moieties.

In some embodiments, provided herein are methods comprising administering a composition described herein to a subject, tissue, sample, or cell. In some embodiments, the composition is administered locally to a site of treatment, diagnosis, or observation. In some embodiments, the composition is administered systemically. In some embodiments, the composition is administered to the peritoneum.

In some embodiments, provided herein are methods of observing a cell, tissue, and/or organ of a subject comprising administering a composition described herein to a subject, and imaging the cell, tissue, and/or organ by magnetic resonance imaging.

In some embodiments, provided herein are methods of imaging the pancreas of a subject, comprising: (a) administering a composition described herein to the subject; (b) allowing the composition to concentrate in the pancreas; and (c) imaging all or a portion of the subject magnetic resonance imaging. In some embodiments, the composition is administered systemically. In some embodiments, the composition is administered to the peritoneum. In some embodiments, the composition is administered to the pancreas.

In some embodiments, provided herein are methods of conjugating a functional moiety to a gold nanoparticle with a lipoic acid molecule, comprising: (a) conjugating the functional moiety to that carboxylic acid group of the lipoic acid molecule; and (b) conjugating the dithiolane of the lipoic acid molecule to the gold nanoparticle.

In some embodiments, provided herein are methods of conjugating a functional moiety to a gold nanoparticle, comprising: (a) reacting a dithiolane-linked azide group with a functional-moiety-linked alkyne group to generate a dithiolane-linked functional moiety; (b) conjugating the dithiolane-linked functional moiety to the gold nanoparticle by binding the dithiolane to the gold nanoparticle.

Additional embodiments and details within the scope herein are described, for example, in the Detailed Description and Examples 1-5.

DEFINITIONS

Figure 1:
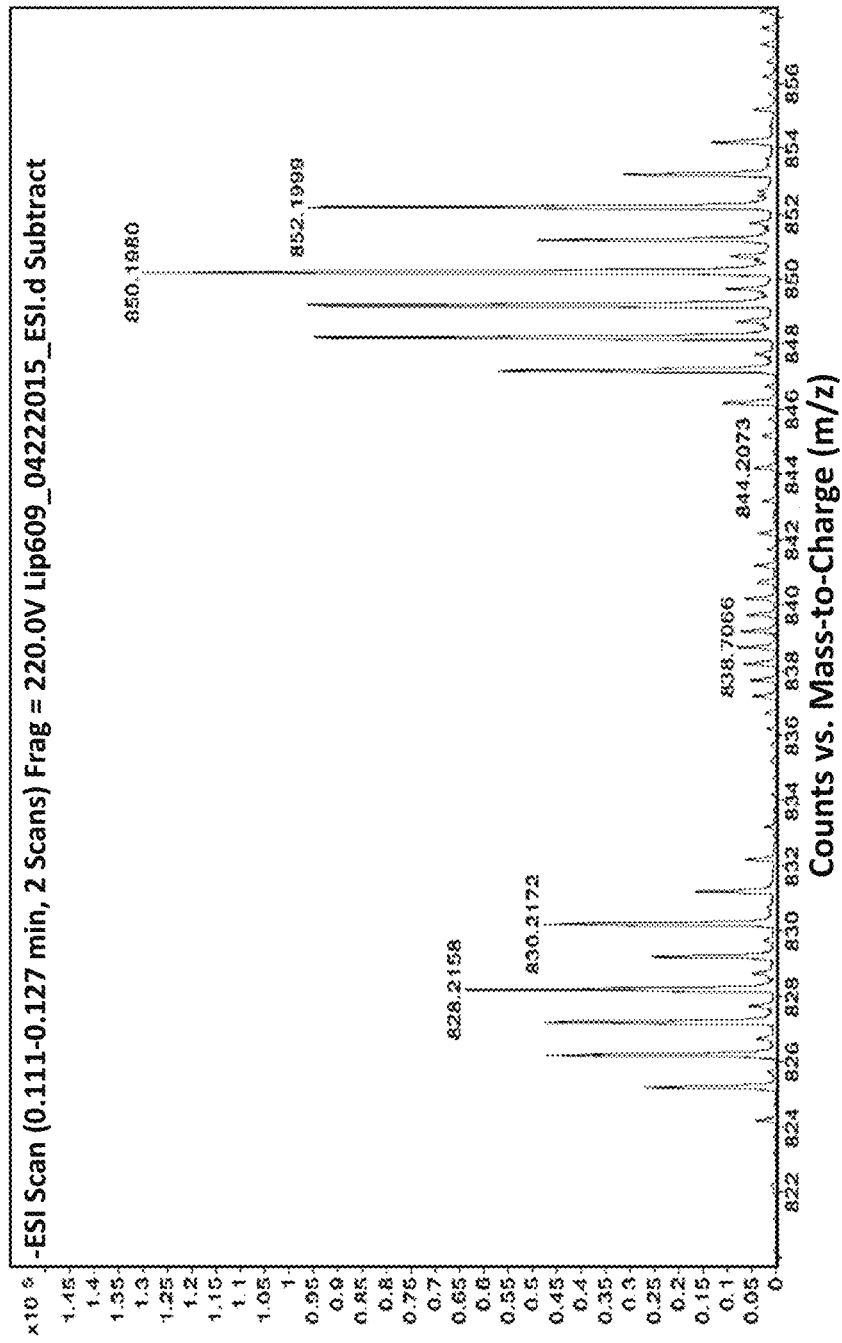
FIG. 1. High resolution ESI-TOF spectrum of dt-Gd(III) complex 4 for $[M+H]^+$ and $[M+Na]^+$.
Figure 2A:
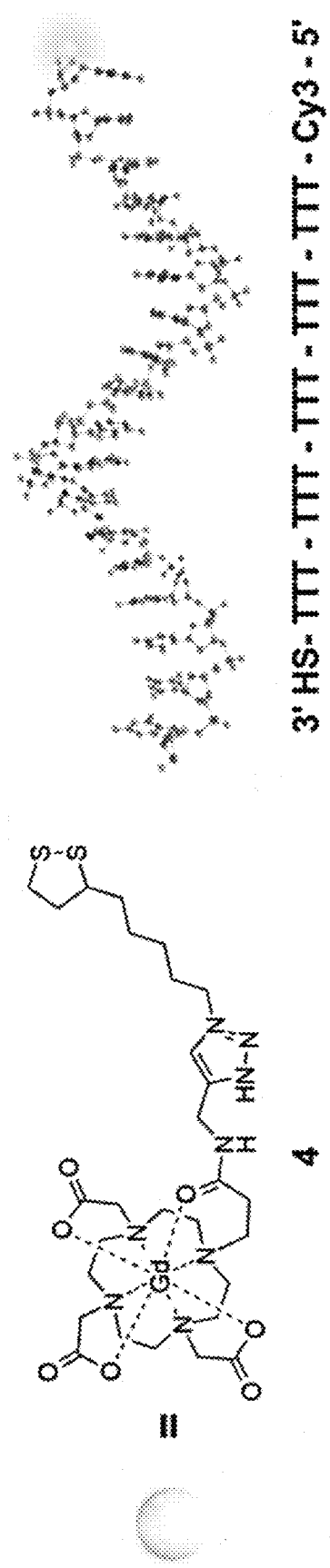
FIGS. 2A-D. Particle functionalization strategies. (a) Component dt-Gd(III) (complex 4) and 5'-Cy3 poly dT DNA used in these studies. (b) Synthetic scheme of dt-Gd (III) pure particle conjugates achieved without the presence of reducing agents. (c) Standard salt aging conjugation protocol using 5' Cy3 poly dT SNAs starting from citrate-stabilized AuNPs. (d) Post-conjugation protocol for dt-Gd (III) backfilling using poly-dT SNAs.
Figure 2B:
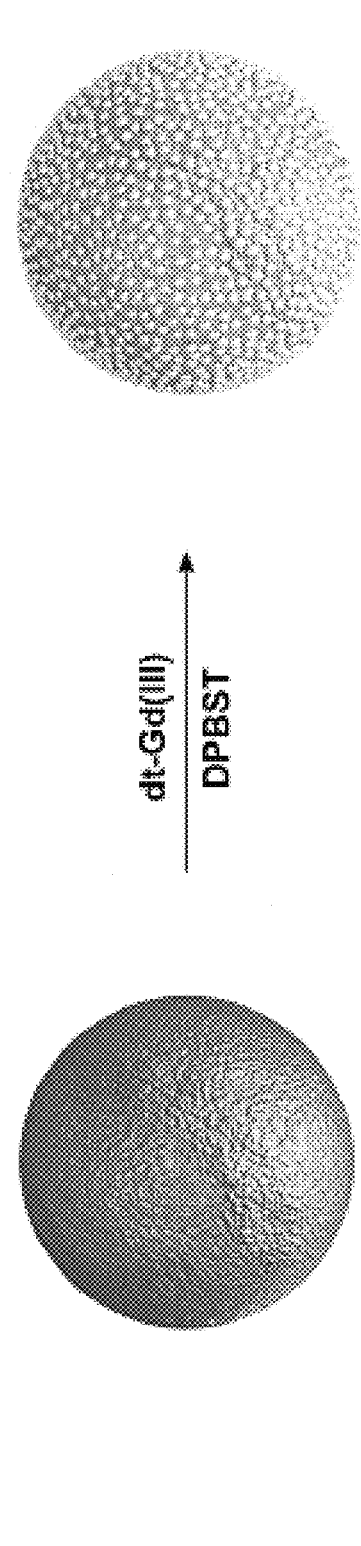
Figure 2C:
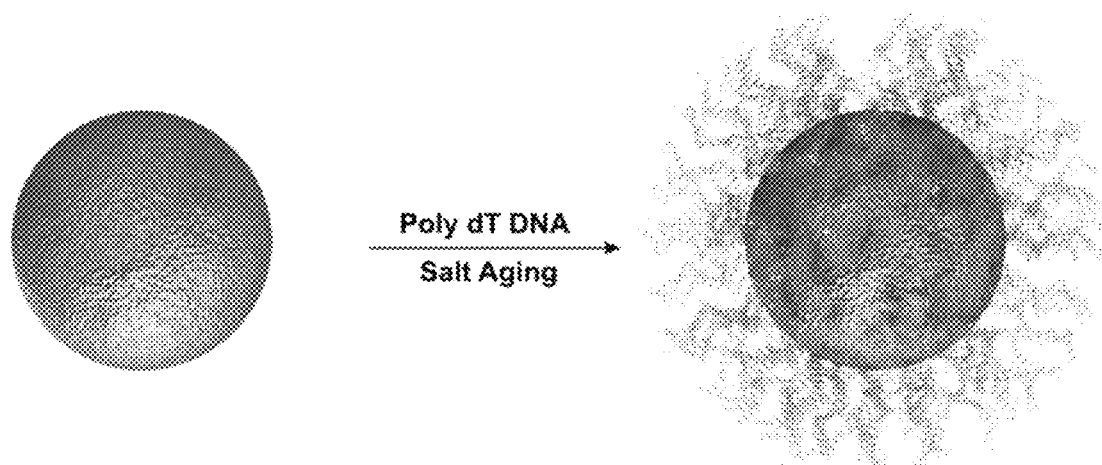
Figure 2D:
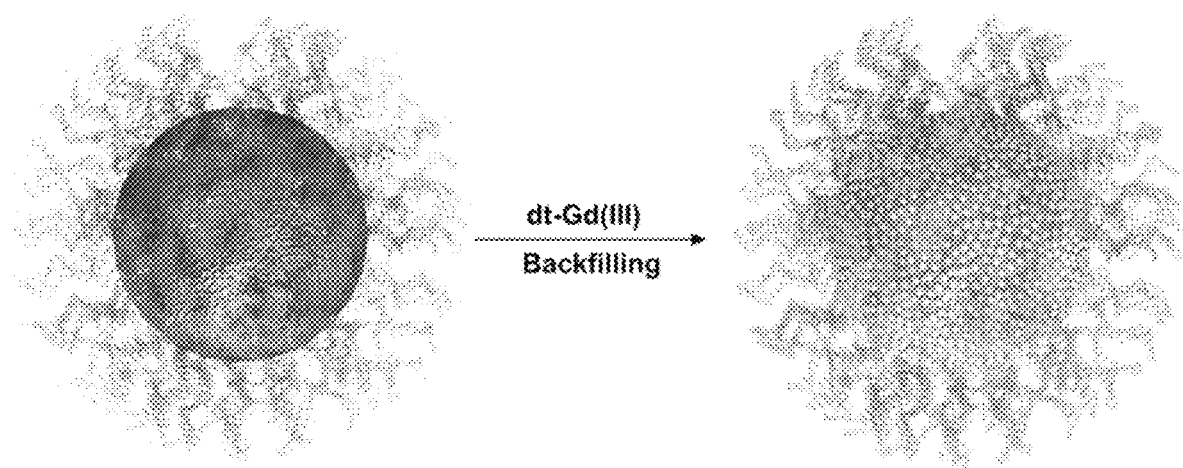

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a Gd(III)-dithiolane gold nanoparticle conjugate" is a reference to one or more Gd(III)-dithiolane gold nanoparticle conjugates, unless the context clearly dictates otherwise.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "substantially" refers to less than 5% variation, and preferably less than 1% variation. For example, for a structure that is "substantially spherical," diameters in all dimensions are within 5% error of each other (and preferably within 1% of each other).

The term "about" allows for a degree of variability in a value or range. As used herein, the term "about" refers to values within 10% of the recited value or range (e.g., about 50 is the equivalent of 45-55).

As used herein, the term "theranostic" refers to the characteristic of having the combined effects of a therapeutic and a diagnostic. For example, a "theranostic nanoparticle" has utility as both a diagnostic and therapeutic agent or displays both diagnostically- and therapeutically-useful moieties.

As used herein, the terms "nanoparticles" and "nanostructures" are used synonymously to refer to particles having diameters in all dimensions of greater than 1 nm and less than 1 am. Nanoparticles are typically spherical or substantially spherical. Nanostrcutures may also be cylindrical, star-shaped, or any other useful shape. All embodiments herein indicated as nanoparticles may also encompass nanostructures (e.g., nanostars), or may be limited to spherical nanoparticles, unless otherwise indicated.

As used herein the terms "spherical nucleic acid" (SNA) or "spherical nucleic acid conjugate" refers to three-dimensional conjugates of densely functionalized and highly oriented nucleic acids covalently attached to the surfaces of nanoparticles.

As used herein, the term "physiologic conditions" refers to solution or reaction conditions roughly simulating those most commonly found in mammalian organisms, particularly humans (e.g., not relating to specific micorenvironments within organisms (e.g., not the acidic conditions (pH 5.0) commonly found in tumor microenvironments and cellular late endosomes) or other rare conditions, unless specifically-noted). While variables such as temperature, availability of cations, and pH ranges may vary, "physiologic conditions" typically mean a temperature of 35-40° C., with about 37° C. being particularly preferred, and a pH of 7.0-8.0, with about 7.5 being particularly preferred. The conditions may also include the availability of cations, preferably divalent and/or monovalent cations, with a concentration of about 2-15 mM $Mg^{2+}$ and 0 1.0 M $Na^+$ being particularly preferred.

As used herein, the term "oligonucleotide" refers to a short polymer of 50 or fewer nucleotide monomers (e.g., 2, 3 4, 5, 6, 7, 8, 9, 10, 11, 12 13, 14, 15, 16, 17, 18, 19, 20, 21, 22, 24, 25, 26, 27, 28, 29, 30, 31, 32 33, 34, 35, 36, 37, 38, 39, 40, 41, 42 43, 44, 45, 46, 47, 48, 49, 50, or any ranges therebetween (e.g., 8-24 nucleotides). Oligonucleotides may be double-stranded oligonucleotide or single-stranded, may comprise deoxyribonucleotides and/or ribonucleotides, and may or natural and/or synthetic/modified nucleotides.

As used herein, the term "targeting moiety" refers to a molecule or macromolecule that has specificity to a marker on or expressed particular cell-type, tissue type, subcellular location, etc. The marker may be extracellular (e.g., on a cell surface or secreted by a cell) or intracellular (e.g., in the cytosol or on/in a specific organelle). The presence of a targeting moiety on a nanoparticle conjugate described herein facilitates localization of the nanoparticle conjugate to a desired tissue, cell, organelle, etc. within a subject.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated or evaluated for a disease or condition.

As used herein, the term "sample" refers to any material, biological fluid, tissue, or cell obtained or otherwise derived from a subject. This includes blood (e.g., whole blood, leukocytes, peripheral blood mononuclear cells, buffy coat, plasma, and serum), sputum, tears, mucus, nasal washes, nasal aspirate, breath, urine, semen, saliva, peritoneal washings, ascites, cystic fluid, meningeal fluid, amniotic fluid, glandular fluid, lymph fluid, nipple aspirate, bronchial aspirate, bronchial brushing, synovial fluid, joint aspirate, organ secretions, cells, a cellular extract, and cerebrospinal fluid. This also includes experimentally separated fractions of all of the preceding. For example, a blood sample can be fractionated into serum, plasma, or into fractions containing particular types of blood cells, such as red blood cells or white blood cells (leukocytes). In some embodiments, a sample can be a combination of samples from an individual, such as a combination of a tissue and fluid sample. The term "sample" may also include materials containing homogenized solid material, such as from a stool sample, a tissue sample, or a tissue biopsy; and materials derived from a tissue culture or a cell culture. Any suitable methods for obtaining a sample can be employed; exemplary methods include, e.g., phlebotomy, swab, and a fine needle aspirate biopsy procedure. Exemplary tissues susceptible to fine needle aspiration include lymph node, lung, lung washes, BAL (bronchoalveolar lavage), thyroid, breast, pancreas, and liver. Samples can also be collected, e.g., by micro dissection, bladder wash, smear, or ductal lavage. A sample obtained or derived from an individual includes any such sample that has been processed in any suitable manner (e.g., filtered, diluted, pooled, fractionated, concentrated, etc.) after being obtained from the individual. A sample may also be a reaction mixture or in vitro cell or tissue culture.

"Diagnose", "diagnosing", "diagnosis", and variations thereof refer to the detection, determination, or recognition of a health status or condition of an individual on the basis of one or more signs, symptoms, data, or other information pertaining to that individual. The health status of an individual can be diagnosed as healthy/normal (e.g., a diagnosis of the absence of a disease or condition) or diagnosed as ill/abnormal (e.g., a diagnosis of the presence of a disease or condition, etc.). The terms "diagnose", "diagnosing", "diagnosis", etc., encompass, with respect to a particular disease or condition, the initial detection of the disease; the characterization or classification of the disease; the detection of the progression, remission, or recurrence of the disease; and the detection of disease response after the administration of a treatment or therapy to the individual.

"Prognose", "prognosing", "prognosis", and variations thereof refer to the prediction of a future course of a disease or condition in an individual who has the disease or condition (e.g., predicting patient survival, predicting the need for interventions, predicting the aggressiveness of a disease, predicting the responsiveness of a disease to a particular treatment, etc.), and such terms encompass the evaluation of disease response after the administration of a treatment or therapy to the individual. Example prognoses include likelihood of mortality (e.g., <1%, <5%, <10<, <20%, <30%, <40%, <50%, >50%, >60%, >70%, >80%, >90%, >95%, >99%), likelihood of responsiveness/resistance to treatment (e.g., <1%, <5%, <10<, <20%, <30%, <40%, <50%, >50%, >60%, >70%, >80%, >90%, >95%, >99%), likely lifespan (e.g., <1 month, <2 months, <3 month, <6 months, <1 year, 2 years, 3 years, >3 years, etc.).

"Evaluate", "evaluating", "evaluation", and variations thereof encompass both "diagnosis" and "prognosis" and also encompass determinations or predictions about the future course of a disease or condition in an individual who does not have the disease as well as determinations or predictions regarding the likelihood that a disease or condition will recur in an individual who apparently has been cured of the disease. The term "evaluate" also encompasses assessing an individual's response to a therapy, such as, for example, determining the aggressiveness of a disease or condition, predicting whether an individual is likely to respond favorably to a therapeutic agent or is likely to develop resistance to a therapeutic agent, selecting a therapeutic agent for administration to an individual, or monitoring or determining an individual's response to a therapy that has been administered to the individual.

As used herein, "detecting" includes the use of both the instrument used (if used) to observe and record a signal, the reagents required to generate that signal, and/or analysis of signals to generate an image or value. In various embodiments, a level is detected using any suitable method, including magnetic resonance imaging, fluorescence, microscopy, other imagine techniques (e.g., CT, PET, SPECT, etc.), etc.

DETAILED DESCRIPTION

Provided herein are compositions Gd(III)-dithiolane gold nanoparticle conjugates and methods of use thereof. In particular, compositions and method find use in in vivo imaging (e.g., magnetic resonance imaging (MRI)), for example, of pancreatic tissue.

I. DNA Gold Nanoparticle Conjugates

Experiments were conducted during development of embodiments herein to maintain the modularity and utility of spherical nucleic acid conjugates (e.g., high stability, beneficial hybridization thermodynamics and kinetics, nuclease resistance, etc.), and to improve Gd(III) payload using a backfilling approach. A marked advantage in nanoconjugate contrast agents (CAs) relative to small molecule Gd(III) complexes is that particle payload necessarily increases the local concentration of Gd(III), and simultaneously provides increased r1 relaxivity, particularly at low magnetic field strengths. Described herein are compositions and methods that further increase Gd(III) proton relaxation efficiency (r1, in mM−1 s−1), particle loading, and particle stability to facilitate the use for longer-term temporal studies in applications such as regenerative medicine, tumor targeting, etc.

In some embodiments, the density of 3' thiolated DNA packing on a spherical gold nanoparticle surface is limited by the negative charge present on the polyanionic backbone of immobilized oligonucleotides. 15 nm particles were found to contain 19 pmol/cm$^2$ when salt-aged to concentrations corresponding to 0.11 DNA/nm$^2$, or 78 DNA/AuNP). By comparison, densities for organic ligands are found to reach as high as 6.26±0.59 monothiolated organic ligands per nm$^2$ for gold nanoparticles of comparable size. With a suitably designed pendant thiol Gd(III) complex, SNAs are post-functionalized with Gd(III) to generate a high payload, high stability hybrid spherical nucleic acid Gd(III) gold nanoparticle conjugate. To this end, experiments were conducted during development of embodiments herein to synthesize a 1,2-dithiolane containing Gd(III) complex derived from (±)-lipoic acid, bearing optimized inner sphere water exchange (τm) and two anchor points for surface immobilization to the gold nanoparticle surface. Provided herein is a scalable approach to the synthesis of a 1,2 dithiolane modified Gd(III) DNA gold nanoparticle conjugates (dt-Gd (III) SNAs). Experiments conducted during development of embodiments herein evaluate the performance and stability of the dt-Gd(III) SNAs. The dt-Gd(III) SNAs demonstrate the ability to bind previously synthesized SNAs at high surface densities, and can be backfilled onto the surface of these particles without the need for reducing agents. Furthermore, this nanoconjugate design is observed to increase r1 relaxivity per Gd(III), and particle payload by greater than 3-fold when compared to DNA-GdIII@AuNPs, while maintaining the high stability, biocompatibility and exhibit improved cellular uptake at lower incubation concentrations relative to the other nanoconjugates.

Experiments conducted during development of embodiments herein demonstrate that using a dithiolane functionalized Gd(III) complex, a new type of backfilled spherical nucleic acid conjugate (dt-Gd(III) SNA) is synthesized which exhibits increased r1 relaxivity, improved Gd(III) loading, comparable conjugate stability and increased cellular uptake at lower incubations concentrations relative to the previous generation of DNA-GdIII@AuNP. Taken together, the greater low field relaxivity, improved Gd(III) loading and more efficient cellular uptake allow the use of less agent per cell labeling trial, thereby increasing the efficiency of the overall process. In addition, due to the modular synthesis of SNAs, different DNA sequences and different functional groups (e.g., targeting groups may replace the Cy3 on exemplary design) may be included. Embodiments herein facilitate the use of Gd(III) nanoconjugates for new cell labeling or targeting applications through the straightforward use of this backfilling methodology.

II. Pancreatic Tissue Labeling for MRI with Gd(III)-Dithiolane Gold Nanoparticles Magnetic resonance imaging (MRI) has emerged as an established technique for providing clinical diagnosis and molecular imaging. It provides tomographic information of live biological specimens with high spatiotemporal resolution and excellent soft tissue contrast without the use of radiotracers or ionizing radiation. As a result, long-term longitudinal studies are possible without significant harm to the specimen. However, lack of intrinsic contrast can limit definitive detection of desired tissue. In these cases, contrast agents (CAs) are used to differentiate tissue types that would otherwise be indistinct. Paramagnetic chelates of Gd(III) are commonly used as CAs, as they shorten the longitudinal relaxation times (T1) of proximal water protons in regions of CA accumulation, and as a result, generate positive image contrast. The efficiency of a CA to reduce T1 of surrounding water protons is determined by the CA's concentration and relaxivity, r1 ($mM^{-1}s^{-1}$), as defined by equation 1:

$$\frac{1}{T_1} = \frac{1}{T_{1,Solvent}} + r_1[Gd(III)].$$

Due to the dependency of T1 on the concentration of Gd(III), CA accumulation strategies that target specific biological areas are of interest. In some embodiments, CAs utilizing small molecule targeting or nanomaterial platforms deliver Gd(III) to regions of interest, providing greater accumulation, and subsequent shorter T1 for greater MR contrast enhancement.

The study of pancreatic diseases is vital to human health. However, insufficient imaging of the pancreas has limited the detection and treatment of a variety of disease states. In particular, pancreas imaging in mice for pancreatic disease models is challenging since the organ is not a defined solid retroperitoneal organ but rather a thin membrane, spread throughout the upper abdomen and lying immediately adjacent to the gut. Furthermore, low intrinsic contrast of the pancreas in T1-weighted MRI and artifacts from motion and intestinal gas can negatively affect the image quality, making detection of the pancreas difficult. To overcome these limitations, accumulation of Gd(III) CAs to the pancreas for image contrast enhancement is desired.

Provided in embodiments herein are Gd(III)-based CAs for accumulation and contrast enhancement of the pancreas. Through functionalization of spherical AuNPs with small molecule Gd(III) CAs, accumulation and image contrast enhancement in the pancreas by systemic IP administration is achieved. To study this system, a variety of Gd(III) CAs were modified with a terminal thiolane ring through conjugation to lipoic acid, and subsequently conjugated to the AuNP surface using gold-thiol chemistry. IP administration of these Lip-Gd(@AuNPs to C56 black mice are shown to accumulate to the pancreas and provide subsequent enhancement MR image contrast at 9.4 T. This facile Lip-Gd@AuNP system provides a nanomaterial platform that utilizes the surface properties for high Gd(III) CA loading of AuNPs and targeted delivery to pancreatic tissue for MRI.

Experiments conducted during development of embodiments herein have demonstrated the facile synthesis of Lip-Gd@AuNPs and their ability to accumulate to the pancreas in vivo and provides MR image contrast enhancement. The modular and facile AuNPs functionalization was demonstrated by the synthesis and development of Lip-DO3AGd@AuNP and Lip-DTPAGd@AuNP systems. Biodistribution experiments demonstrate the accumulation of these AuNPs to the pancreas. TEM and Histology demonstrate nanoparticle uptake in pancreatic tissue through. As a result of this pancreatic accumulation, significant MR image contrast enhancement of the pancreas is observed through IP administration of Lip-Gd@AuNPs. In addition to in vivo studies, cell labeling in MDA-MB-231 cells is demonstrated.

These AuNPs provides a robust platform for the development of Gd(III)-based MRI CAs.

In some embodiments, AuNP conjugates do not comprise nucleic acid linkers.

III. Compositions

In some embodiments, provided herein are nanoparticle conjugates comprising a nanoparticle core and displaying one or more (e.g., 2, 3, 4, 5, 6, 7, 8, or more) different pendant groups on their surface. In some embodiments, the nanoparticle core comprises a core material (e.g., gold (Au), etc.) and a surface that is amenable to attachment of pendant groups (e.g., covalently or noncovalently) via specific chemistry (e.g., either inherently or through surface functionalization). In some embodiments, pendant groups comprise an attachment moiety (e.g., thiol, dithiolane, etc.), linker moiety (e.g., nucleic acid, peptide, alkyl chain, heteroalkyl chain, etc.), and/or functional moiety (e.g., metal chelation moiety, fluorophore, therapeutic, etc.).

In some embodiments, the compositions herein comprise nanoparticle cores conjugated to one or more different pendant groups. The nanoparticle cores that find use in embodiments herein may be of any suitable material. In some embodiments, the nanoparticle core is inorganic. In some embodiments, the nanoparticle core comprises one or more of iron, iron oxide, gold, platinum silica, silver, titanium dioxide, etc. In some embodiments, nanoparticles are gold nanoparticles.

In some embodiments, the surface of the nanoparticle core is suitable for attachment (e.g., covalent or noncovalent) of pendant groups. In some embodiments, the surface of the nanoparticle is the core material.

In some embodiments, nanoparticles may have a propensity to aggregate and/or precipitate out of solution, resulting in a non-uniform dispersion of the nanoparticles and/or leading to a loss of the desired effects of the nanoparticles. In some embodiments, to inhibit aggregation, nanoparticles are surrounded by a surface protective layer. The surface protective layer may comprise a wide variety of molecules or combinations thereof which inhibit nanoparticle aggregation. In some embodiments the molecules comprise organic and/or inorganic compounds which can be chemically or physically bound to the nanoparticle core, depending on the properties of the materials selected. Methods of bonding are well-known in the art, including but not limited to covalent and ionic bonding, as well as physical adsorption. In some embodiments, the nanoparticles are citrate-stabilized gold nanoparticles.

In some embodiments, the surface of the nanoparticle is functionalized to facilitate pendant attachment. In some embodiments, the surface of a nanoparticle is functionalized to produce a surface-functionalized nanoparticle. In some embodiments, chemical moieties and/or functional groups on (or conjugated to) the nanoparticle surface include, but are not limited to: amino groups, aldehyde groups, carboxylate groups, thiol groups, hydroxyl, haloalkyl, acyl halide, alkyne, azide, biotin, or any suitable biological, organic and/or inorganic functional groups. In some embodiments, the surface of a nanoparticle is not surface functionalized.

In some embodiments, nanoparticle cores are spherical or substantially-spherical and have diameters of less than 500 nm (e.g., <400 nm, <300 nm, <200 nm, <100 nm, <50 nm, <40 nm, <30 nm, <20 nm). In some embodiments, nanoparticle cores have diameters of 5-50 nm (e.g., 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, or any ranges therebetween (e.g., 10-20 nm, etc.)).

In some embodiments, the compositions herein comprise one or more different pendant groups displayed on the surface, and/or conjugated to, nanoparticle cores. The pendant groups are constructed of one or more moieties, selected from, for example, an attachment moiety (e.g., a functional group that binds to and/or is reactive with the surface of the nanoparticle core), a linker moiety (e.g., substantially linear moiety that extends from the core), one or more functional moieties (e.g., metal chelation moiety, fluorophore, therapeutic moiety, etc.), etc.

In some embodiments, pendant groups comprise an attachment moiety. In some embodiments, an attachment moiety comprises a functional group that facilitates attachment (e.g., covalent or noncovalent) of the pendant group to the nanoparticle core. In some embodiments, particularly when the nanoparticle core is a metal core (e.g., Au Ag, Pt, etc.) or stabilized (e.g., citrate-stabilized) metal core, an attachment moiety comprises a sulfur-containing functional group, such as a thiol-based, or dithiol-based, functional group. Multiple embodiments of sulfur-containing functional groups are available for use (See, e.g., M. Brust et. al., "Synthesis of thiol-derivatized gold nanoparticles in a two-phase Liquid-Liquid system," Journal of the Chemical Society, Chemical Communications, p 801, 1994; A. C. Templeton, W. P. Wuelfing, and R. W. Murray, "Monolayer-Protected Cluster Molecules," Accounts of Chemical Research, vol. 33, no. 1, p 27-36, 2000; M-C. Daniel and D. Astruc, "Gold nanoparticles: Assembly, Supramolecular Chemistry, Quantum-Size-Related Properties, and Applications toward Biology, Catalysis, and Nanotechnology," Chemical Reviews, vol. 104, no. 1, p 293-346, 2004; incorporated by reference in their entireties). Sulfur-containing attachment functional groups include, but are not limited to, a wide range of straight-chain alkanethiols ($C_3$-$C_{24}$), ω-functionalized alkanethiolates (functionalized with Br, CN, vinyl, ferrocene, phenyl, —OH, —COOH, —COOCH$_3$, and anthraquinone groups), thiolated polymers, p-mercaptophenol, aromatic alkanethiols, phenyl alkanethiols, mercaptoalkyl-trialkoxysilane, disulfides, xanthates, dithiols (e.g., dithiolanes (e.g., 1,2-dithiolane and 1,3-dithiolane), etc.), trithiols, and tetrathiols. In some embodiments, a pendant group is conjugated to a nanoparticle core by a dithiolnae or thiol attachment moiety.

While several examples of sulfur-containing or thiol-based attachment moieties are provided above, pendant attachment is not so limited. A wide range of functional group may suffice in certain embodiments herein. For example, non-sulfur-containing attachment moieties may include, but are not limited to, citrates (e.g. trisodium citrate), phosphines, phosphine oxides, amines, carboxylates, isocyanides, quarternary ammonium salts, surfactants, and polymers.

In some embodiments, the attachment moieties described above serve to conjugate a functional moiety (e.g., chelation moiety, fluorophore, therapeutic moiety, etc.) to the nanoparticle core. In some embodiments, the attachment moiety and the functional moiety of the pendant group are directly attached. However, in other embodiments, a linking moiety is provided between the attachment moiety and the functional moiety.

In some embodiments, a linking moiety is a substantially-linear (e.g., allowing for branching, substituents, modifications, and/or pendants off the linear chain or backbone) moiety that connects the attachment moiety to a functional moiety. Any suitable linker may find use in embodiments herein. Indeed, a variety of linker moieties are contemplated, and suitable linkers could comprise, but are not limited to, alkyl groups, methylene carbon chains, ether, polyether, alkyl amide linkers, a peptide linkers, a modified peptide linkers, a poly(ethylene glycol) (PEG) linker, a streptavidin-biotin or avidin-biotin linker, polyaminoacids (e.g. polylysine), functionalized PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (WO94/08629, WO94/09056 and WO96/26754, herein incorporated by reference in their entireties), oligonucleotide linker (e.g., poly dT), phospholipid derivatives, alkenyl chains, alkynyl chains, disulfide, or combinations thereof.

In some embodiments, a linker moiety is an organic chain (e.g., linear or substantially-linear) comprising any combination of alkyl, alkenyl, alkynyl, phenyl, benzyl, halo, fluoro, chloro, bromo, bromo, iodo, hydroxyl, carbonyl, aldehyde, haloformyl, carbonate ester, carboxylate, carboxyl, ester, hydroperoxy, peroxy, ether, hemiacetal, hemiketal, acetal, ketal, orthoester, amide, amine, imine, imide, azide, azo, cyanate, nitrate, nitrite, nitrile, nitro, nitroso, pyridine, thiol, sulfide, disulfide, sulfoxide, sulfone, sulifinic acid, sulfonic acid, thiocyanate, thione, thial, phosphine, phosphonic acid, phosphate, and/or phosphodiester groups. Any suitable linkers, utilizing any suitable functional groups, are within the scope of embodiments herein.

In some embodiments, a linker moiety comprises a carbon chain (e.g., alkyl) of 2-24 carbons (e.g., 2, 3, 4, 5, 6, 7, 8, 9, 10, 11, 12, 13, 14, 15, 16, 17, 18, 19, 20, 21, 22, 23, 24, or any ranges therebetween). In some embodiments, the carbon chain comprises one or more substituent or pendant functional groups (e.g., =O, —OH, —NH2, etc.). In some embodiments, one or more carbons of the chain are substituted with a heteroatom (e.g., N, S, O, S). In some embodiments, the carbons chain comprises one or more double or triple bonds.

In some embodiments, the linker moiety is lipoic acid.

In some embodiments, a linker moiety comprises a nucleic acid (e.g., DNA, RNA, etc.). In some embodiments, a linker moiety comprises an oligonucleotide. In some embodiments, a linker moiety comprises a single-stranded oligonucleotide. In some embodiments, an oligonucleotide linker moiety is 2-50 nucleotides in length (e.g., 2, 3 4, 5, 6, 7, 8, 9, 10, 11, 12 13, 14, 15, 16, 17, 18, 19, 20, 21, 22, 24, 25, 26, 27, 28, 29, 30, 31, 32 33, 34, 35, 36, 37, 38, 39, 40, 41, 42 43, 44, 45, 46, 47, 48, 49, 50, or any ranges therebetween (e.g., 8-24 nucleotides). In some embodiments, the 5' end of an oligonucleotide linker moiety is attached to a functional moiety and the 3' end of the oligonucleotide linker moiety is attached to an attachment moiety. In some embodiments, the 3' end of an oligonucleotide linker moiety is attached to a functional moiety and the 5' end of the oligonucleotide linker moiety is attached to an attachment moiety. In some embodiments, one or more functional moieties (e.g., chelation moiety, fluorophore, therapeutic moiety, etc.) are attached to one or more bases (e.g., comprising reactive side-chain modifications (e.g., C6 amino modifier dT modified bases, etc.)) within the oligonucleotide linker.

In some embodiments, one or more modified nucleotides incorporated into a nucleic acid (e.g., nucleic acid linker) herein. Suitable modified nucleotides that are used, in some embodiments, include, but are not limited to: C6 amino modifier dT modified bases, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. Other suitable modified nucleotides are understood in the field.

In some embodiments, an oligonucleotide linker is a oligomer (e.g., 2-50 monomers) of deoxy-thymine nucleotides. In some embodiments, an oligonucleotide linker comprises an oligomer of deoxy-thymine nucleotides and modified (e.g., C6 amino modifier dT modified bases) deoxy-thymine nucleotides. In some embodiments, the modified bases comprise location for attachment of functional moieties.

In some embodiments, pendant groups comprise a functional moiety. In some embodiments, the functional moiety is present on the distal end of the pendant moiety (e.g., the proximal end being attached to the core). In some embodiments, one or more functional moieties are attached along the length of a linker moiety. In some embodiments, a linker moiety comprises a distal functional moiety and one or more functional moieties are attached along the length of a linker moiety.

Any chemical moieties that impart a diagnostic and/or therapeutic functionality to the nanoparticle conjugates described herein may find use in embodiments herein. A functional group includes, but is not limited to, a nucleic acid molecule, a protein, a peptide, a peptide nucleic acid, an epitope recognized by a ligand (e.g., biotin or streptavidin), an antibody, and antibody fragment, a hapten, a lipid, a fluorophore, a chromophore, a reporter molecule, a radionuclide, a metal chelator, an electron opaque molecule, an X-ray contrast reagent, a MRI contrast agent, an intercalator, a cross-linker, and the like.

In some embodiments, the functional moiety is a chelation moiety (e.g., a functional group or combination of functional groups capable of coordinating, for example, a metal ion). In some embodiments, the functional moiety is a chelation moiety and a coordinated metal ion. In some embodiments, a chelation moiety is selected from the group consisting of EDTA, DTPA, TTHA, DOTA, TAGA, DOTP, DTPA-BMA, DO2P, and HP-DO3A.

In some embodiments, a chelation moiety coordinates a metal ion that is useful as a contrast agent (e.g., MRI contrast agent). In some embodiments, metal ions useful in a diagnostic and/or therapeutic applications herein include, for example, metal ions (e.g., chelated metal ion) is selected from the group consisting of Mn(II), Gd(III), Dy(III), Ho(III), Er(III), Eu(III), Tb(III), Sm(III), Ce(III), Pr(III), Yb(III), Tm(III), Nd(III), and Tb(IV). In some embodiments, the metal ion is Gd(III).

In some embodiments, a chelation moiety coordinates a radionuclide. In some embodiments, radionuclides useful in a diagnostic and/or therapeutic applications herein include, for example, metallic radionuclides (e.g., metallic radioisotopes or metallic paramagnetic ions), including Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-67, Erbium-169, Europium-152, Gallium-64, Gallium-68, Gadolinium-153, Gadolinium-157 Gold-195, Gold-199, Hafnium-175, Hafnium-175-181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Titanium-44, Tungsten-185, Vanadium-48, Vanadium-49, Ytterbium-169, Yttrium-86, Yttrium-88, Yttrium-90, Yttrium-91, Zinc-65, and Zirconium-95. Radionuclides useful for imaging include radioisotopes of copper (Cu), gallium (Ga), indium (In), rhenium (Rh), and technetium (Tc), including isotopes $^{64}$Cu, $^{67}$Cu, $^{111}$In, $^{99m}$Tc, $^{67}$Ga or $^{68}$Ga.

In some embodiments, chelated metals herein are useful as X-ray contrast agents and include, for example, radioisotopes of Re, Sm, Ho, Lu, Yt, Pm, Bi, Pd, Gd, La, Au, Yb, Dy, Cu, Rh, Ag and Ir.

In some embodiments, a functional moiety is a detectable moiety, for example, and optically detectable moiety. In some embodiments, a functional moiety is a fluorophore, fluorescent dye, or fluorescent protein. Non-limiting examples of fluorophores or fluorescent dyes suitable for use as imaging agents include Alexa Fluor dyes (Invitrogen Corp.; Carlsbad, Calif.), fluorescein, fluorescein isothiocyanate (FITC), Oregon Green; rhodamine, Texas red, tetrarhodamine isothiocynate (TRITC), CyDye fluors (e.g., Cy2, Cy3, Cy5), and the like. Embodiments are not limited to such fluorophores, and additional fluorophores are within the scope herein. Examples of fluorescent proteins include, but are not limited to, green fluorescent protein, red fluorescent protein (e.g., DsRed), yellow fluorescent protein, cyan fluorescent protein, blue fluorescent protein, and variants thereof. Specific examples of GFP variants include, but are not limited to, enhanced GFP (EGFP), destabilized EGFP, the GFP variants, cerulean fluorescent proteins, and the yellow fluorescent protein. DsRed variants include mStrawberry, mCherry, mOrange, mBanana, mHoneydew, and mTangerine, mRaspberry and mPlum.

In some embodiments, a functional moiety is a targeting moiety. In some embodiments, a targeting moiety is tissue-specific, cell-specific, cancer-specific, disease-specific, and/or biomarker-specific. Suitable targeting moieties include a protein-binding partner or a receptor on the surface of a cell, which functions to target the nanoparticles to the specific cell and/or to a specific tissue type (e.g., diseased tissue), and/or or to interact with a specific moiety, either in vivo or in vitro. Suitable protein-binding partners include, but are not limited to, antibodies and functional fragments thereof, scaffold proteins, or peptides. Exemplary targeting moieties include: antibody, thyrotropin, melanotropin, lectin, glycoprotein, surfactant protein A, mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic, or an aptamer. Any targeting moiety capable of localizing, delivering, and/or concentrating the nanoparticle conjugates described herein in a desired location (e.g., cell, tissue, etc.) may find use in embodiments herein.

In some embodiments, a functional moiety is a crosslinking moiety, such as, but not limited to hydrazide, aryl azide, maleimide, iodoacetamide/bromoacetamide, N-hydroxysuccinimidyl ester, mixed disulfide such as pyridyl disulfide, glyoxal/phenylglyoxal, vinyl sulfone/vinyl sulfonamide, acrylamide, boronic ester, hydroxamic acid, imidate ester, isocyanate/isothiocyanate, or chlorotriazine/dichlorotriazine.

In some embodiments, a functional moiety is a therapeutic agent. Suitable therapeutic agents include, but are not limited to, norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepam; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-muscarinic agents; beta-muscarinic agents, such as carvedilol and metoprolol; antiarrhythmic agents; diuretics, such as chlorothlazide, hydrochlorothiazide, flumethiazide, hydroflumethiazide, bendroflumethiazide, methylchlorothiazide, trichloromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; 25yridine25amine25ries; antiproliferatives, such as methotrexate, FK506 (tacrolimus, Prograf), mycophenolate mofetil; chemotherapeutic agents; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and 25yridine analogues; antibiotics, such as anthracyclines, bleomycins, mitomycin, dactinomycin, and plicamycin; enzymes, such as L-asparaginase; farnesyl-protein transferase inhibitors; hormonal agents, such as estrogens/antiestrogens, androgens/antiandrogens, progestins, and luteinizing hormone-releasing hormone anatagonists, and octreotide acetate; microtubule-disruptor agents, such as ecteinascidins; microtubule-stabilizing agents, such as 25yridine25a, docetaxel, and epothilones A-F; plant-derived products, such as vinca alkaloids, epipodophyllotoxins, and taxanes; topoisomerase inhibitors; prenyl-protein transferase inhibitors; cyclosporins; steroids, such as prednisone and dexamethasone; cytotoxic drugs, such as 25yridine25ami and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

In some embodiments, nanoparticle conjugates comprise two or more different pendant conjugated to a nanoparticle core. In some embodiments, pendants have different attachment moieties (e.g. thiol and dithiolane). In some embodiments, pendants have different linking moieties (e.g. lipoic acid and oligonucleotide). In some embodiments, pendants have different functional moieties (e.g. MRI contrast agent and therapeutic, MRI contrast agent and optically-detectable moiety, etc.). In some embodiments, the inclusion of multiple different pendant groups on the nanoparticle core provides for bi-, tri, or multi-modal functionality (e.g., bimodal imaging, theranostics, etc.).

IV. Applications

The nanoparticle conjugate compositions (e.g., AuNp and contrast agent (e.g., Gd(III)) conjugates) described herein find use in a variety of research, therapeutic, diagnostic, screening, patient-evaluation, theranostic, and drug-development applications.

Experiments conducted during development of embodiments herein have demonstrated that conjugated gold nanoparticles (e.g., when administered peritoneally) concentrate in pancreatic tissues/cells. In some embodiments, such nanoparticle conjugates find use in imaging of the pancreas of a subject, and/or monitoring diseases, conditions, treatments, etc. related to the pancreas.

In some embodiments, the compositions and methods of generating conjugated gold nanoparticles described herein facilitate the attachment of two or more different functional groups to a single nanoparticle. Nanoparticles displaying two different functional groups facilitate bimodal imaging (e.g., contrast agent and optically-detectable moiety), theranostics (e.g., contrast agent and therapeutic agent), targeted therapies (e.g., targeting moiety and therapeutic agent), targeted imaging (e.g., targeting moiety and contrast agent), etc. In some embodiments, combinations of multiple different (e.g., 2, 3, 4, 5, 6 or more) functional groups (e.g., targeting moiety, contrast agent, therapeutic, radionuclide, optically-detectable moiety, etc.) provide nanoparticles that are useful for multiple applications and/or complex application requiring multiple functionalities.

Experiments conducted during development of embodiments herein demonstrate the capacity of nanoparticles displaying a first functional moiety conjugated to the nanoparticle by an oligonucleotide linker to be 'back-filled' with a second functional moiety using dithiolane conjugation to the nanoparticle. Such modularity provides for the generation of customizable nanoparticle conjugates displaying combinations of functional moieties tailored to specific tasks.

EXPERIMENTAL

Example 1

DNA Gold Nanoparticle Conjugates—Results

Design Parameters for a Backfilling Approach

The design of the exemplary dt-Gd(III) SNA system leverages numerous beneficial features of Gd(III) nanoconjugate CAs, including the stability and utility of the DNA-Gdn@AuNP conjugates, and the straightforward synthesis and scalability of other directly functionalized Gd(III) complex surface modified particle systems. The 1,2-dithiolane anchor was selected for the efficacy of the cyclic disulfide functionality as a surface ligand for gold, including its specific use for surface conjugation of modified DNAs to gold nanoparticles. The Gd(III) complex 3 was utilized in this work to ensure that inner sphere water exchange with the Gd(III) metal center ($\tau_m$) is operating at an optimal rate and because it is readily be conjugated to an azide bearing dithiolane anchor.

Synthesis and Characterization of dt-Gd(III) Complex

To generate the azide functionalized dithiolane linker suitable for covalent attachment to the Gd(III) complex, initial synthesis utilized the commercially available racemic mixture of (±)-lipoic acid. Reduction of the racemic mixture of dithiolanes in THF using Borane-THF complex at 0° C. to room temperature over 3 hours afforded a 95% yield of (±)-lipoic alcohol. Activation of the alcohol using p-toluenesulfonyl chloride in pyridine followed by extraction and substitution using sodium azide produced the lipoic azide in 69% overall yield through two steps. Finally, using the Cu(I)-catalyzed Huisgen 1,3 dipolar cycloaddition reaction, the final dt-Gd(III) complex (4) was synthesized (Scheme 1). Finding effective conditions for the dipolar cycloaddition reaction were non-trivial, and required consideration of very different solubilities between the organic soluble (±)-lipoic azide and the highly hydrophilic Gd(III) complex 3. After testing numerous solvents and combinations of solvents, including introduction of tris-hydroxypropyltriazolylamine (THPTA) for increased solubility and stabilization of Cu(I), a set of biphasic reaction conditions were attempted. Dissolving the organic azide in ethyl acetate, and the copper(II) sulfate and complex 3 in water at a 1:1 solvent volumes, the solutions were mixed, and a third equal part of methanol was added to facilitate miscibility of the layers. Sodium ascorbate was then added to reduce the Cu(II) to the catalytic species and the reaction was sealed and left to stir overnight. These conditions proved highly effective and showed a 100% coupling efficiency over 12 hours as indicated by loss of starting materials by ESI-MS. Final purification of complex 4 was achieved by HPLC and final characterization was confirmed by high resolution ESI-TOF mass spectrometry (FIG. 1).

Scheme 1

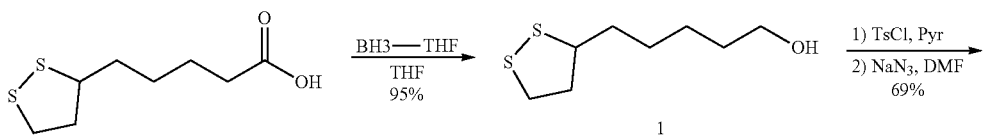

1

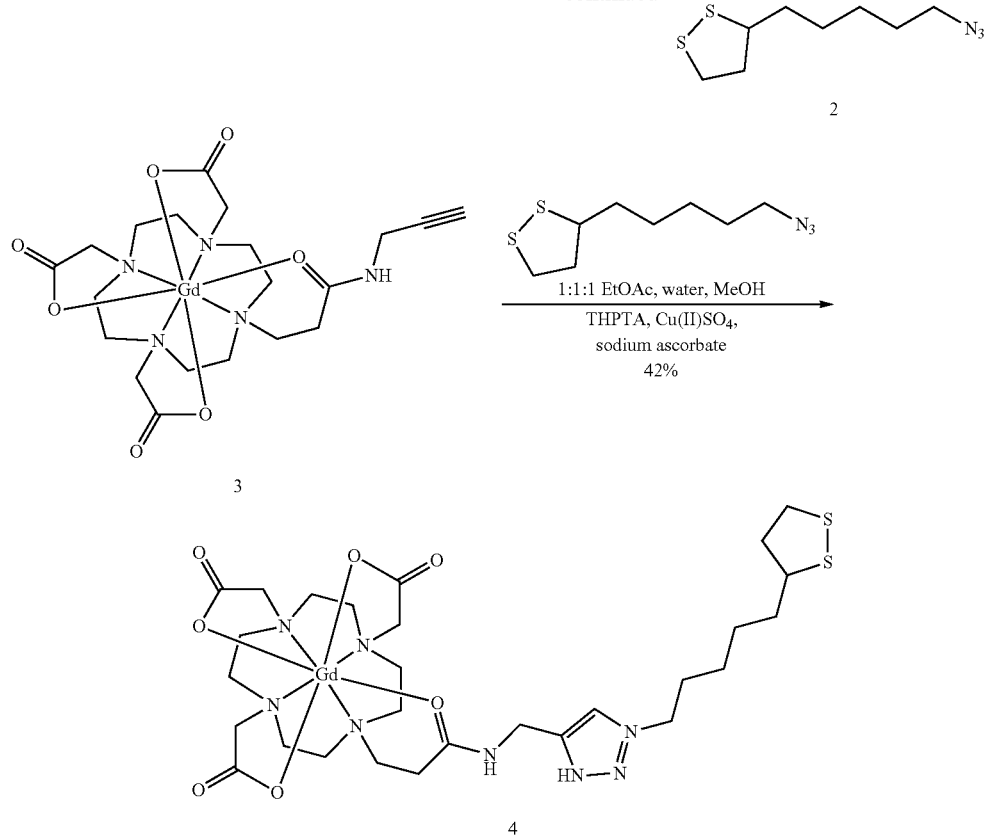

Scheme 1. Synthetic scheme of dt-Gd(III). Generation of the azide bearing dithiolane begins with reduction of the carboxylic acid to the corresponding alcohol (1), followed by activation and substitution of that position on the molecule by an azide (2). An azide-alkyne 1,3 dipolar cycloaddition of Gd(III) complex 3 with the compound 2 affords final complex 4, dt-Gd(III).

Synthesis of Backfilled SNAs

To test the backfilling approach, poly-dT SNAs were synthesized using the same batch of 13 nm citrate-stabilized gold nanoparticles as with dt-Gd(III) pure particle conjugates. Specifically, SNAs were made by salt-aging 3' thiolated 24-mer poly dT DNA bearing a 5' Cy3 fluorophore (FIGS. 2A-D). Upon completion of the conjugation process, particles were concentrated and purified from excess DNA, citrate and sodium chloride though successive rounds of centrifugation. To assess the DNA conjugation efficiency, SNAs were incubated with potassium cyanide to digest the gold cores, and UV/Vis measurement of Cy3 was used to quantify DNA concentration. Results indicated a total surface loading of 199±0.6 strands per particle. Using the purified poly-dT SNAs concentrated to ten times their initial concentration, 50 k equivalents of dt-Gd(III) were added directly, and functionalization was achieved with stirring over 24 hours. Advantageously, backfilling of SNAs was observed to proceed without the use of any reducing agents. The dt-Gd(III) SNAs were again purified by centrifugation, and were measured to generate an $r_1$ of 22.0 mM$^{-1}$ s$^{-1}$ at 37° C. (1.41 T), with a particle payload of 730±11 Gd(III) complexes per particle (Table 1). Relative to the dt-Gd(III) pure particle conjugates, a 23% improvement in $r_1$, is observed while sacrificing only 35% of the Gd(III) loading. In a subsequent synthesis of poly-dT SNAs, dt-Gd(III) was added directly to the DNA conjugation mixture to test the capacity of performing DNA conjugation and backfilling in one pot. By combining the DNA conjugation and backfilling procedures, and purifying particles similarly, the co-functionalization process produced dt-Gd(III) SNAs loaded with 691 dt-Gd(III) per particle after 24 hours, showing good agreement with previous batches of dt-Gd(III) SNAs.

TABLE 1 r1 relaxivity and particle loading values for the Gd(III) nanoconjugates reported. Ionic relaxivity describes the relaxivity per Gd(III), whereas particle relaxivity refers to the sum of these relaxivities per particle.

| | $r_1$ relaxivity (mM$^{-1}$ s$^{-1}$)$^a$ | | Paticle |
| --- | --- | --- | --- |
| | ionic | particle | Loading |
| dt-Gd(III) | 4.9 | NA | NA |
| dt-Gd(III) pure particle | 17.1 | 19270 | 1125 ± 17 |
| Gd-DNA@spheres$^b$ | 12.8 | 6620 | 515 ± 15 |
| dt-Gd(III) SNA | 22.0 | 16080 | 730 ± 11 |

Figure 3A:
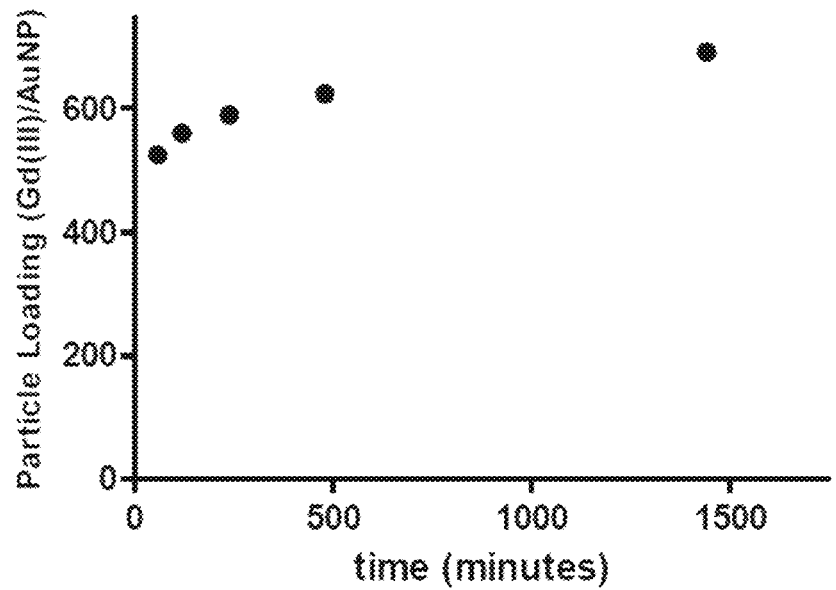
FIGS. 3A-B. Observed loading of dt-Gd(III) over 24 hours by a) Gd(III)/AuNP and b) % of total.
Figure 3B:
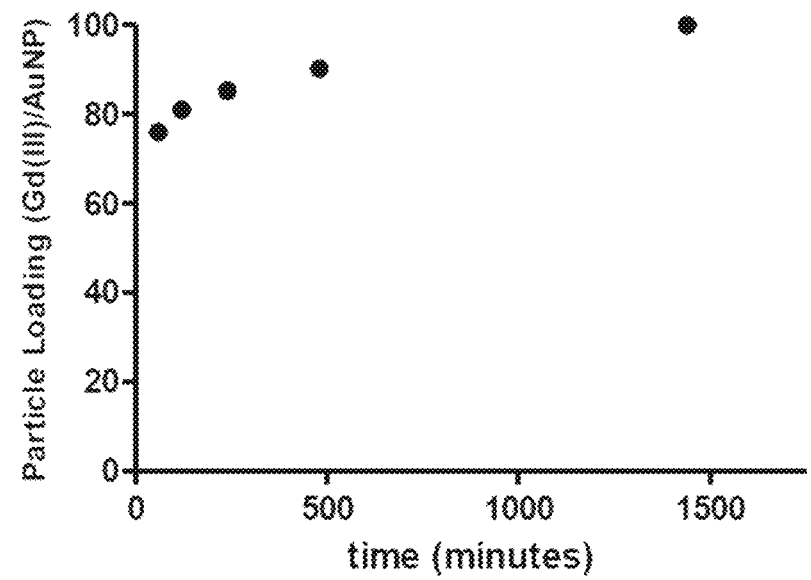
Figure 4A:
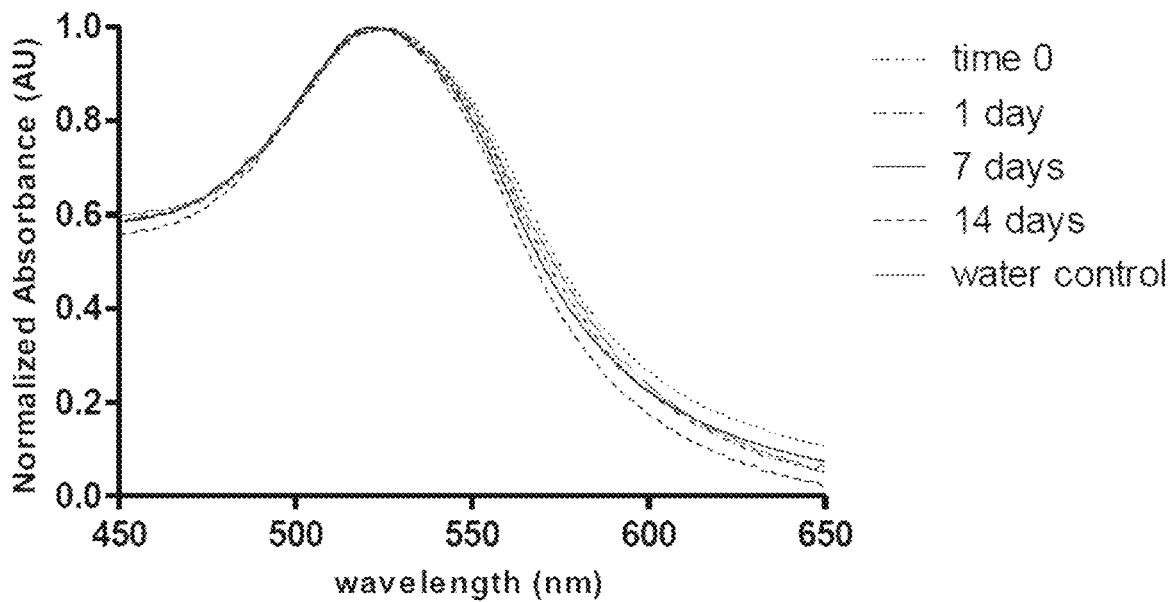
FIGS. 4A-F. Colloidal stability of dt-Gd(III) SNAs and DNA-Gd@spheres measured under various conditions over 14 days at 37° C. dt-Gd(III) SNAs were examined in (a) PBS, (b) 10% FBS and (c) FBS. DNA-Gd@spheres were examined in (d) PBS, (e) 10% FBS, and (f) FBS.
Figure 4B:
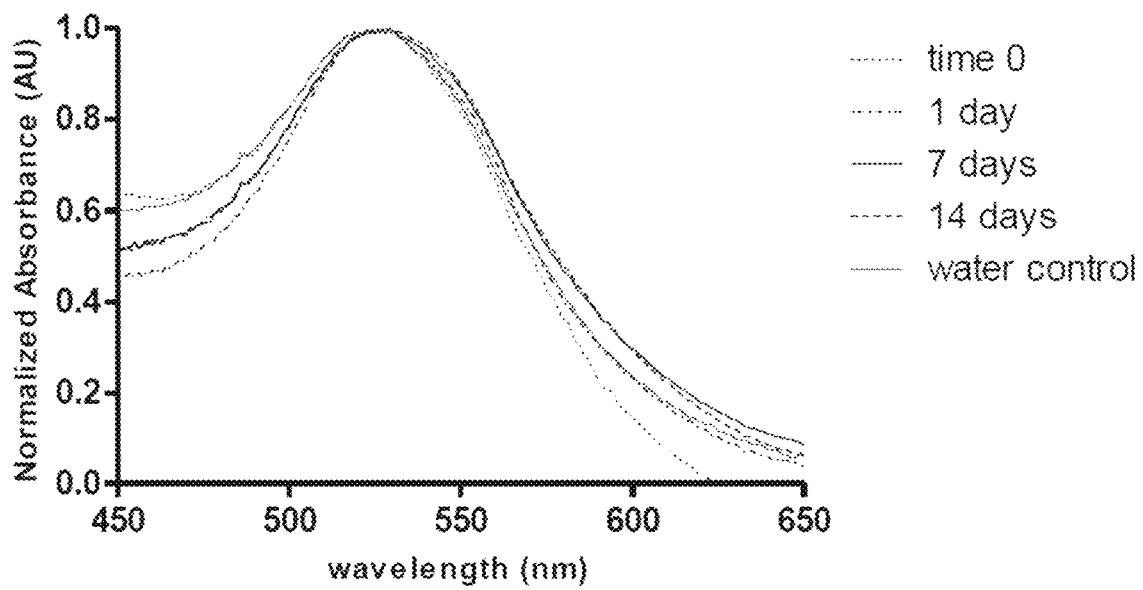
Figure 4C:
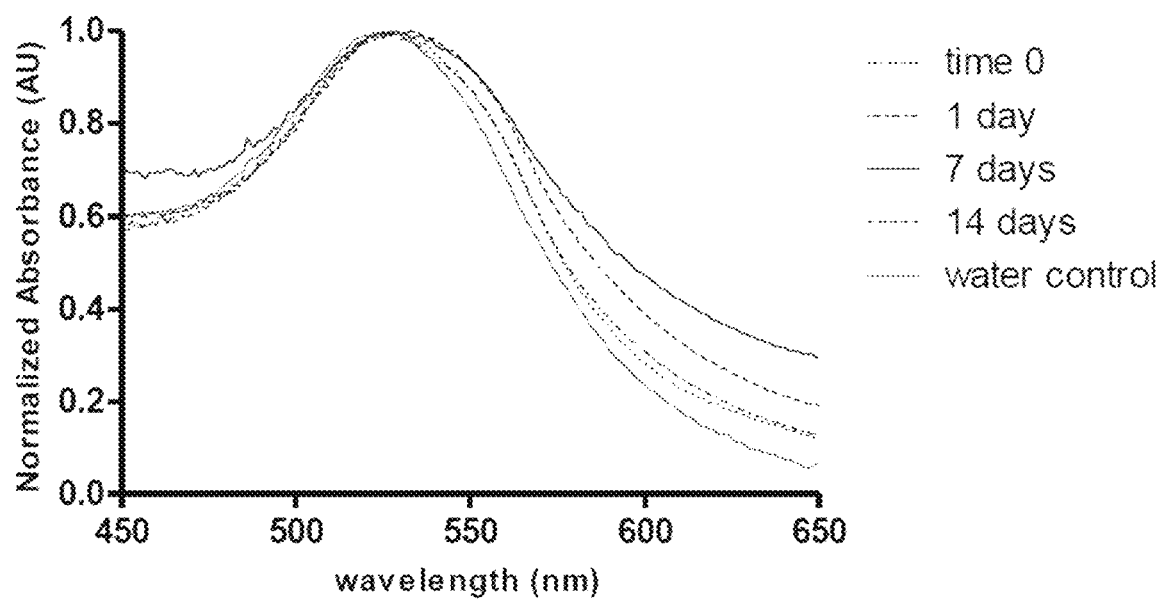
Figure 4D:
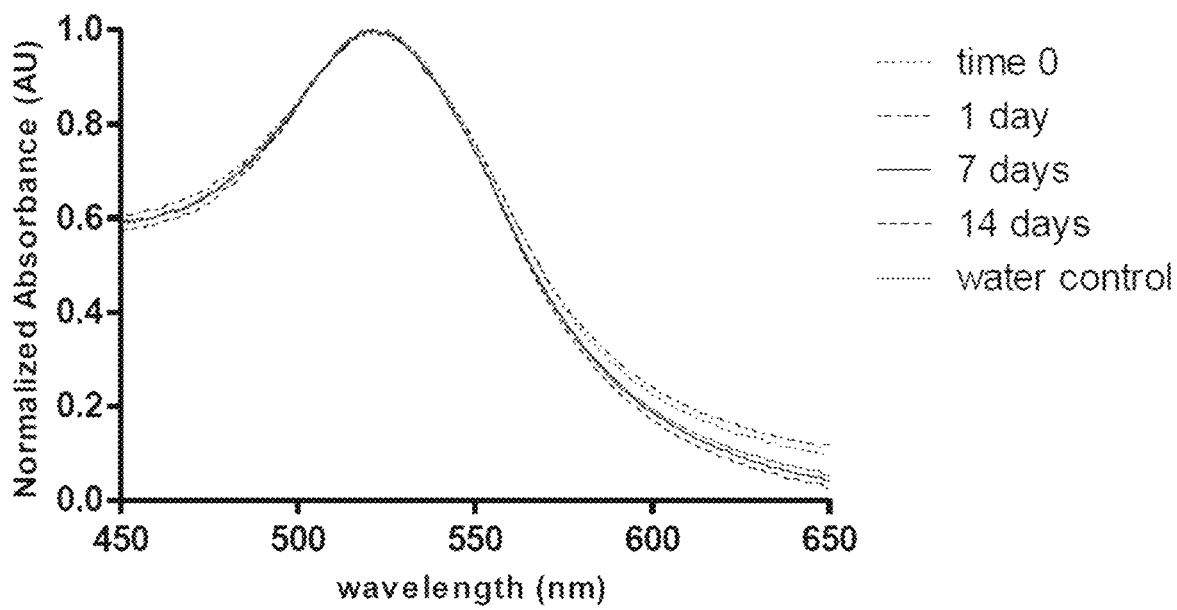
Figure 4E:
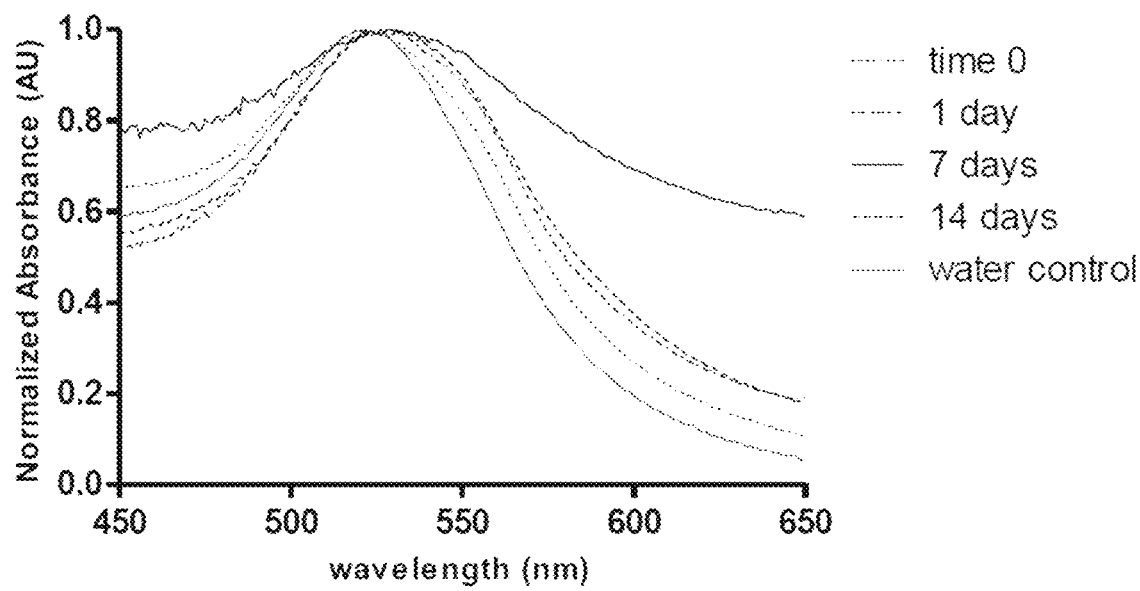
Figure 4F:
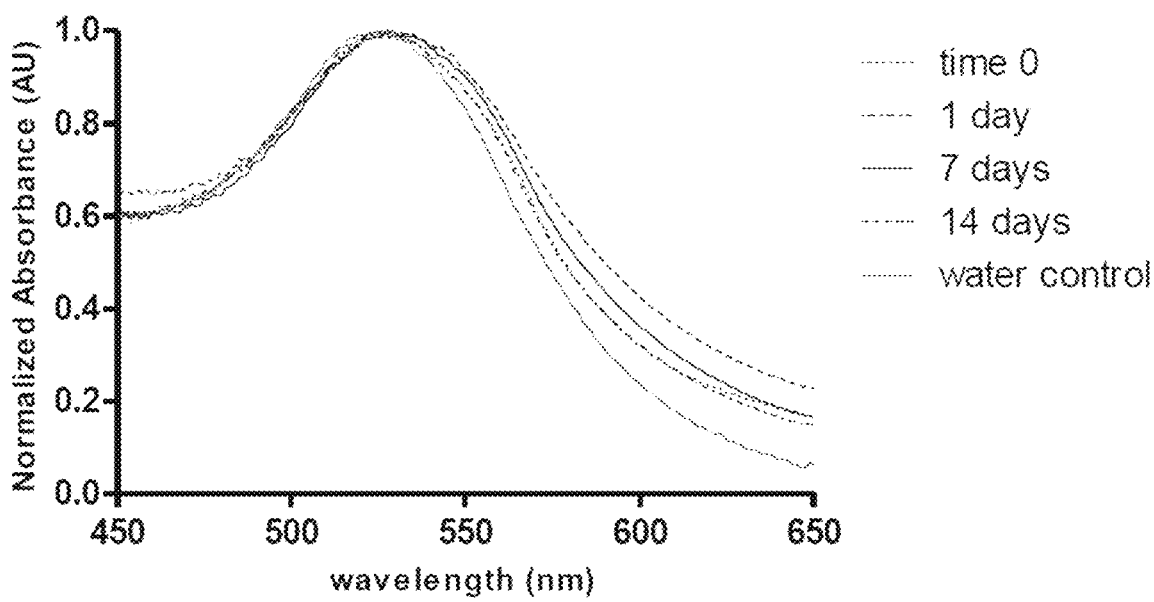

$^a$at 60 MHz, 37° C. in water plus 0.01% tween 20.
$^b$Synthesized and measured for this work, as previously deacribeb[22]
NA = not applicable Backfilling Kinetics For a more complete understanding of backfilling kinetics, a purified batch of poly-dT SNAs were mixed with dt-Gd(III) as described above, and aliquots were removed at 1, 2, 4, 8 and 24 hours. Particles from each time point were purified by the standard procedure, and results indicated that 76% of particle loading was complete within 60 minutes (FIGS. 3A-B). A final loading of particles in this batch after 24 hours totaled 687 Gd(III) per particle.

Comparison with Previous Generation Gd(III)-DNA AuNPs

To understand how dt-Gd(III) SNAs performed relative to the previous generation of Gd(III)-DNA gold nanoparticle conjugates, Gd-DNA@spheres were synthesized as described.[22] Analysis of these conjugates showed considerably better particle loading than all previously reported versions of this construct, totaling 515±15 Gd(III) complexes per particle and an $r_1$ of 12.8 $mM_{-1\,s-1}$ at 37° C. (1.41 T). Despite the remarkably high Gd(III) loading observed here for the Gd-DNA@spheres construct, the density of Gd(III) is still limited to only 0.97 complexes per $nm^2$ from 103±3 DNA per particle (corresponding to a DNA density of 0.19 DNA per $nm^2$). The limitation of further loading can be attributed to the density restrictions supplied by the negative charges on the DNA backbone, and the steric crowding imposed by the long covalent linker from the modified DNA bases. In comparison, dt-Gd(III) SNAs achieve improvements in the densities of both Gd(III) and DNA loading, better by 1.4- and 2-fold, respectively (Table 2). In some embodiments, achieving such a high density of oligonucleotide loading provides both increased utility for sequences tailored to specific applications, and enhances nuclease stability relative to less densely functionalized SNAs.

TABLE 2

Comparative surface densities of gold nanoparticle conjugates

| | Surface Density ($/nm^2$) | |
|---|---|---|
| | Gd(III) | DNA |
| dt-Gd(III) pure particle | 2.12 | NA |
| Gd-DNA@spheres | 0.97 | 0.19 |
| dtGd(III) SNAs | 1.38 | 0.38 | dt-Gd(III)-SNA Stability

Figure 5A:
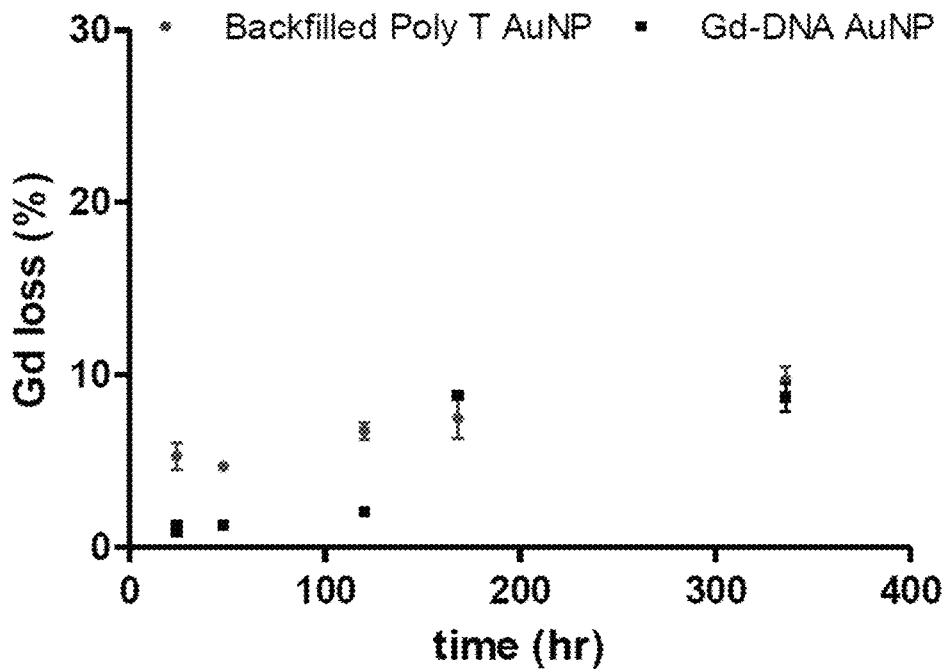
FIGS. 5A-C. Supernatant analysis of dt-Gd(III) SNAs and DNA-Gd@spheres in (a) PBS, (b) 10% FBS and (c) FBS.
Figure 5B:
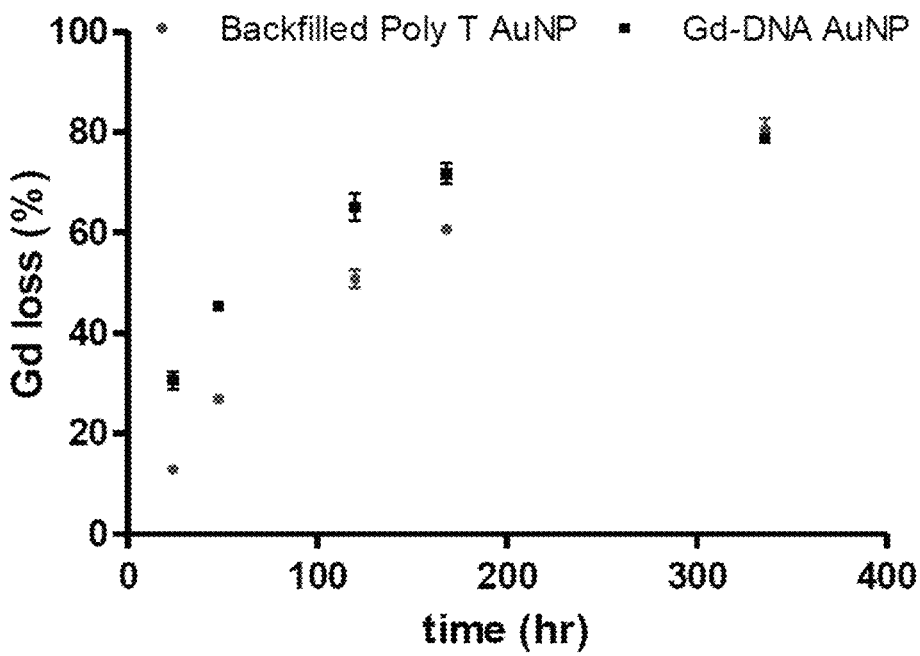
Figure 5C:
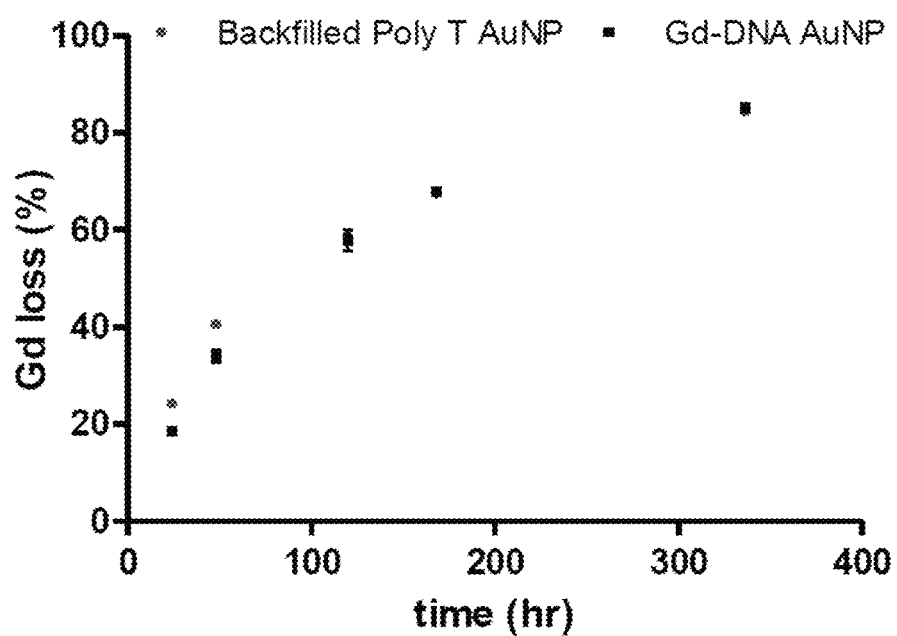

To study the effects of the 1,2-dithiolane on the stability of dt-Gd(III) SNAs, the backfilled conjugates were exposed to various cell culture related conditions alongside the Gd-DNA@sphere constructs. Specifically, concentrated solutions of both conjugates were diluted to equimolar concentrations in PBS, DMEM, 10% FBS in DMEM and 100% FBS and incubated at 37° C. under sterile conditions for two weeks. Particle concentration and Gd(III) loading was quantified at time zero for each solution, and each condition was run in duplicate. Time points were recorded at each of 24, 48, 120 168 and 336 hours by removal of an aliquot from the incubated solution followed by centrifugation, and ICP-MS analysis of supernatant Gd(III). Concurrently, the colloidal stability was assessed by observation of the plasmon resonance peak at time points of 1, 7 and 14 days for both constructs under all conditions above. After 24 hours, both nanoconjugates had crashed out of DMEM, while the remaining solutions all stayed visibly red and in solution through the duration of the study. The surface plasmon resonance peaks for each construct indicated maximum values at 527 and 521 nm for backfilled and Gd(III) DNA conjugated particles in water for time zero, and all solutions showed a variable increase in this value over 14 days, particularly solutions of FBS (FIGS. 4A-F). Results of the supernatant analysis were plotted as a percentage of loss from the starting Gd(III) concentration of fully loaded particles. These data indicated that under these stringent conditions, both constructs were very vulnerable to degradation under all conditions excepting PBS, despite the different presentation and number of thiols present on the monothiolated Gd(III) DNAs and the backfilled dt-Gd(III) complexes (FIGS. 5A-C).

Cellular Uptake and Toxicity of dt-Gd(III) SNAs

Figure 6A:
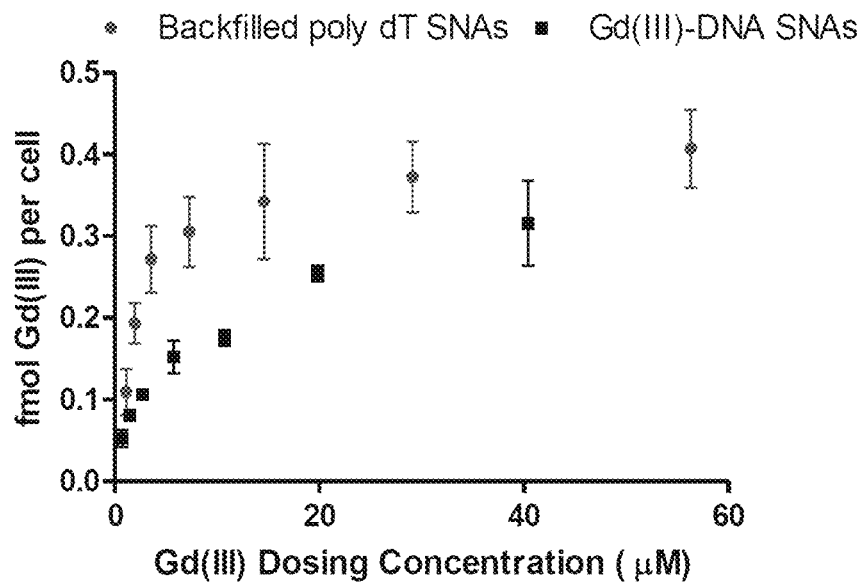
FIGS. 6A-B. 24 hour cell uptake experiment comparing dt-Gd(III) SNAs and DNA-Gd@spheres described by (a) Gd(III) dosing, or (b) AuNP dosing concentrations.
Figure 6B:
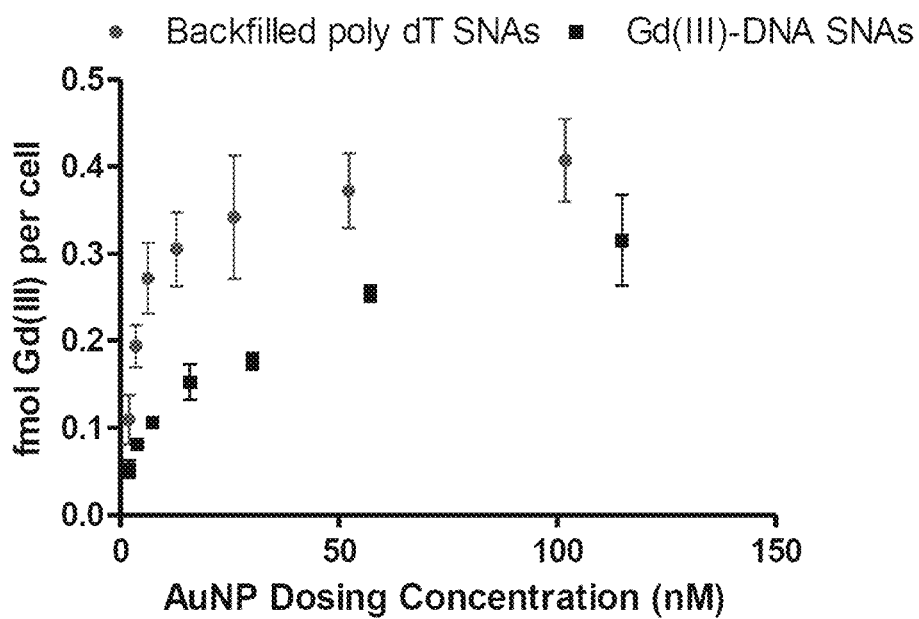

To test the biocompatibility and cellular uptake efficiency of dt-Gd(III) SNAs and Gd-DNA@spheres, HeLa cells were prepared and dosed using various dilutions of nanoconjugates in 10% FBS in DMEM. After 24 hours, cells were washed, trypsinized, and counted. At this time point, cell counts were as expected and no toxicity was observed for any of the incubation concentrations. Counted cells were digested in 1:1 $HNO_3$ and HCl and Gd(III) and gold content was examined using ICP-MS. Per concentration of nanoconjugates observed, the dt-Gd(III) SNAs provided improved Gd(III) uptake, particularly at lower incubation concentrations (FIGS. 6A-B). The improved Gd(III) payload was not the only cause of the improved uptake, as cells dosed with the dt-Gd(III) SNAs appeared to take up slightly more of the nanoconjugates at each of the concentrations examined. This detail may be explained by the higher density loading of DNA present on the dt-Gd(III) SNAs relative to the DNA-Gd@spheres, which are limited in the densities of DNA which can be achieved due to the steric crowding of the particle surface resultant from the long linker arm of the covalently attached Gd(III) complex; however, embodiments herein are not limited to any particular mechanism of action, and an understanding of the mechanism of action is not necessary to practice such embodiments.

Example 2

DNA Gold Nanoparticle Conjugates—Materials/methods

Chemical Synthesis and Characterization

Solvents and reagents were purchased from Sigma-Aldrich unless otherwise noted. Synthetic procedures were carried out under ambient conditions unless described otherwise. Chemical characterization was performed using a Varian 500 MHz NMR and a Bruker AutoFlex III MALDI spectrometer. Gd(III) complex purification was performed using a Varian Prostar 500 HPLC using a Waters C8 Sunfire 19×150 mm 5 µm column and mobile phases of Millipore water, and HPLC grade acetonitrile. Nanoparticle characterization was performed on JOEL 1230 and Hitachi HD7700 TEMs. UV/Vis/NIR spectra of colloidal solutions were collected on an Agilent UV/Vis spectrophotometer. DLS and zeta-20 potential measurements were obtained using a Brookhaven ZetaPals zeta potential and particle size analyzer. Oligonucleotides were synthesized using solid phase, controlled pore glass beads (CPGs) by standard techniques on a MerMade automated synthesizer. Reagents, protected 3' thiol modifier CPGs, and C6 amino modifier dT modified bases were purchased from Glen Research (Sterling, Va.). Oligonucelotides were deprotected from the solid phase using AMA conditions [(1:1 methylamine:ammonium hydroxide (sat.)] for sixty minutes. Oligonucleotide purification was performed by HPLC using a mobile phase consisting of 30 mM triethyl ammonium acetate buffer pH 7 (TEAA) and acetonitrile (ACN). A method containing a gradient of 75% Acetonitrile over 45 minutes was applied, as monitored by backbone and Cy3 wavelengths at 254 and 546 nm, respectively. Post-purification, oligonucleotides were lyophilized and stored at −20° C. Inorganic Gd(III) complex 4 (Scheme 1) was synthesized using standard organic chemistry techniques. ICP-MS was performed on either a computer-controlled (Plasmalab software) Thermo (Thermo Fisher Scientific, Waltham, Mass.) PQ ExCell ICP-MS equipped with a CETAC 500 autosampler or a computer-controlled (Plasmalab software) Thermo X series II ICP-MS equipped with an ESI (Omaha, Nebr., USA) SC-2 autosampler.

5-(1,2-dithiolan-3-yl)pentan-1-ol (1)

To a two-necked 250 mL round bottom flask was added a stir bar and (±) lipoic acid (1.00 g, 4.8 mmol). To this was added 50 mL of dry THF under nitrogen atmosphere, with stirring until complete dissolution of lipoic acid. The mixture was cooled to 0° C., at which time was added 1.0 M Borane-THF complex (7.3 mL, 7.3 mmol)) dropwise over ten minutes. The yellow solution was observed to bubble during addition of Borane-THF and was left to warm to room temperature with stirring over 3 hours. The reaction was again cooled to 0° C. and 5 mL of methanol was added dropwise to quench the remaining Borane-THF. After no further bubbling was observed, it was left open to air under positive flow of nitrogen until the majority of solvent had evaporated. The crude mixture was dissolved into 20 mL diethyl ether and extracted with saturated sodium bicarbonate (3×20 mL), brine (1×20 mL) and the diethyl ether layer was dried over sodium sulfate and evaporated by rotary evaporation. The crude mixture was purified by silica gel flash chromatography using conditions of 1:1 ethyl acetate: hexanes, visualized by CAM stain ($R_f$=0.45). Product is a viscous yellow oil. Yield: 0.879 g, 95.3% $^1$H NMR (500 MHz, Chloroform-d) δ 3.64 (t, J=6.5 Hz, $^1$H), 3.57 (dq, J=8.6, 6.4 Hz, 1H), 3.24-3.06 (m, 1H), 2.52-2.41 (m, 1H), 1.97-1.86 (m, OH), 1.75-1.35 (m, $^4$H). $^{13}$C NMR (126 MHz, CDCl$_3$) δ 62.95, 56.75, 40.41, 38.59, 35.02, 32.68, 29.24, 25.71.

3-(5-azidopentyl)-1,2-dithiolane (2)

To a 100 mL round bottom flask with a magnetic stir bar was added the lipoic alcohol from above (0.879 g, 4.5 mmol) and 30 mL of pyridine with cooling to 0° C. To the stirring mixture was added tosyl chloride (1.91 g, 10.0 mmol), and was left to stir overnight. Complete conversion to product was observed by thin layer chromatography under conditions of 1:1 ethyl acetate:hexanes and visualized by CAM (Rf=0.65). The crude mixture was dissolved into 50 mL of diethyl ether and was extracted with 1M HCl (aq.) (2×50 mL), saturated sodium bicarbonate (1×50 mL), and brine (1×50 mL). The organic layer was dried over sodium sulfate and was positively identified by crude NMR and ESI-MS: (m/z) observed: 369.2, calculated: 369.5 [M+Na]+. The crude product was taken on to azide substitution without further purification. Into 20 mL of DMF was dissolved the tosylated lipoic alcohol and sodium azide (0.468 g, 7.2 mmol). To the stirring mixture was added a spatula tip of potassium iodide and the reaction was left to stir at 60° C. for 3 days. After such time, thin layer chromatography using 1:1 ethyl acetate:hexanes appeared to show only starting material, but crude ESI-MS indicated complete conversion to product, (m/z) observed: 240.8, calculated: 240.3 [M+Na]+. After rotary evaporation of DMF, crude product is extracted with diethyl ether and each of water, saturated aqueous sodium bicarbonate and brine (50 mL each). The extracted diethyl ether is dried over sodium sulfate and evaporated under vacuum yielding one spot by TLC, CAM (Rf=0.65), and a clean NMR of the 3-azidopentyl substituted 1,2 dithiolane. Product is a viscous yellow oil. Yield: 0.721 g, 69.2% overall yield. $^1$H NMR (500 MHz, Chloroform-d) δ 3.57 (dq, J=8.6, 6.4 Hz, 1H), 3.27 (t, J=6.9 Hz, 2H), 3.23-3.08 (m, 2H), 2.47 (m, J=13.0, 6.6, 5.4 Hz, 1H), 1.92 (dq, J=12.7, 7.0 Hz, 1H), 1.78-1.38 (m, 9H). $^{13}$C NMR (126 MHz, CDCl$_3$) δ 62.95, 56.75, 40.41, 38.59, 35.02, 32.68, 29.24, 25.71.

2,2'2''(10(3-(((1-(5-(1,2-dithiolan-3-yl)pentyl)-1,2,3-triazol-4-yl)methyl)amino)-3-oxopropyl)-1,4,7,10-tetraazacyclododecyl-gadolinium(III) complex (4)

To a 10 mL round bottom flask containing a stir bar, nitrogen atmosphere, and water (2 mL) was added copper(II) sulfate pentahydrate (0.007 g, 0.03 mmol) and tris-hydroxy-propyltriazolylamine (0.026 g, 0.06 mmol). To this mixture was further added complex 3 (0.1 g, 0.16 mmol) with stirring. After complete dissolution was observed, sodium ascorbate (0.06 g, 0.3 mmol) was added. To a separate vial was dissolved compound 2 (0.52 g, 0.24 mmol) and ethyl acetate (2 mL). The dissolved 2 in ethyl acetate was then combined with the stirring aqueous solution of complex 3 and copper, THPTA and sodium ascorbate making a biphasic mixture. To the stirring mixture was then added methanol (2 mL) to coalesce the phases, and the reaction was left to stir overnight at room temperature. ESI-MS was used to indicate complete reaction of starting materials and positively identify complex 4. Purification of complex 4 was achieved using high performance liquid chromatography (HPLC) using a Waters C8 Sunfire (semipreparative column on a Varian ProStar 500 system with freshly purified water and HPLC grade acetonitrile as the mobile phase. Specifically, purification was achieved at a flowrate of 15 mL/min using a method which held 5% acetonitrile from 0-5 minutes, followed by a linear ramp to 40% between 5-20 minutes and to 100% between 20-25 minutes. Complex 4 elutes between 13.4 and 13.8 minutes as monitored by UV absorbance at 200/210 nm. Final compound is an off white solid. Yield 0.561 g, 41.5%. (Final characterization was confirmed by high resolution ESI-TOF MS: (m/z) observed: 850.1980, calculated: 851.08 [M+Na]+.

Metals Analysis by ICP-MS

Quantitation of metal concentration was assessed by initial acid digestion of nanoconjugate samples, followed by dilution of acid into water and analysis by ICP-MS. Gadolinium and gold samples were prepared by different dilution factors such that were within the range of the selected standard concentrations. Specifically, Gd analyses were conducted by addition of 5 ul of nanoconjugate sample into 120 ul of 1:1 concentrated nitric acid: concentrated hydrochloric acid (TraceSelect Nitric acid, >69%; TraceSelect HCl, fuming 37%) for digestion of metal contents. Au analyses were made by addition of 5 uL of nanoconjugate sample to 500 uL of 1:1 HNO$_3$:HCl as above, and mixed thoroughly. Millipore water and multi-element internal standard (CLISS-1, Spex Certiprep, Metuchen, N.J., USA) containing 6Li, Sc, Y, In, Ho, Bi were added to produce a solution of 2% nitric acid (v/v), 2% HCl (v/v) and 5.0 ng/mL internal standard up to a total sample volume of 3 mL (Gd) and 10 mL (Au) after 20-fold dilution of original aliquot. Individual Au/Gd mixed-metal elemental standards were prepared at 0, 0.78125, 1.5625, 3.125, 6.25, 12.5, 25.0, 50.0, 100, and 200 ng/mL concentrations with 2% nitric acid (v/v), 2% HCl (v/v) and 5.0 ng/mL internal standards up to a total sample volume of 5 mL. Each sample was acquired using 1 survey run (10 sweeps) and 3 main (peak jumping) runs (100 sweeps). The isotopes selected were $^{197}$Au, $^{156,157}$Gd and $^{115}$In, $^{165}$Ho, and $^{209}$Bi (as internal standards for data interpolation and machine stability).

Relaxivity ($r_1$)

Figure 7:
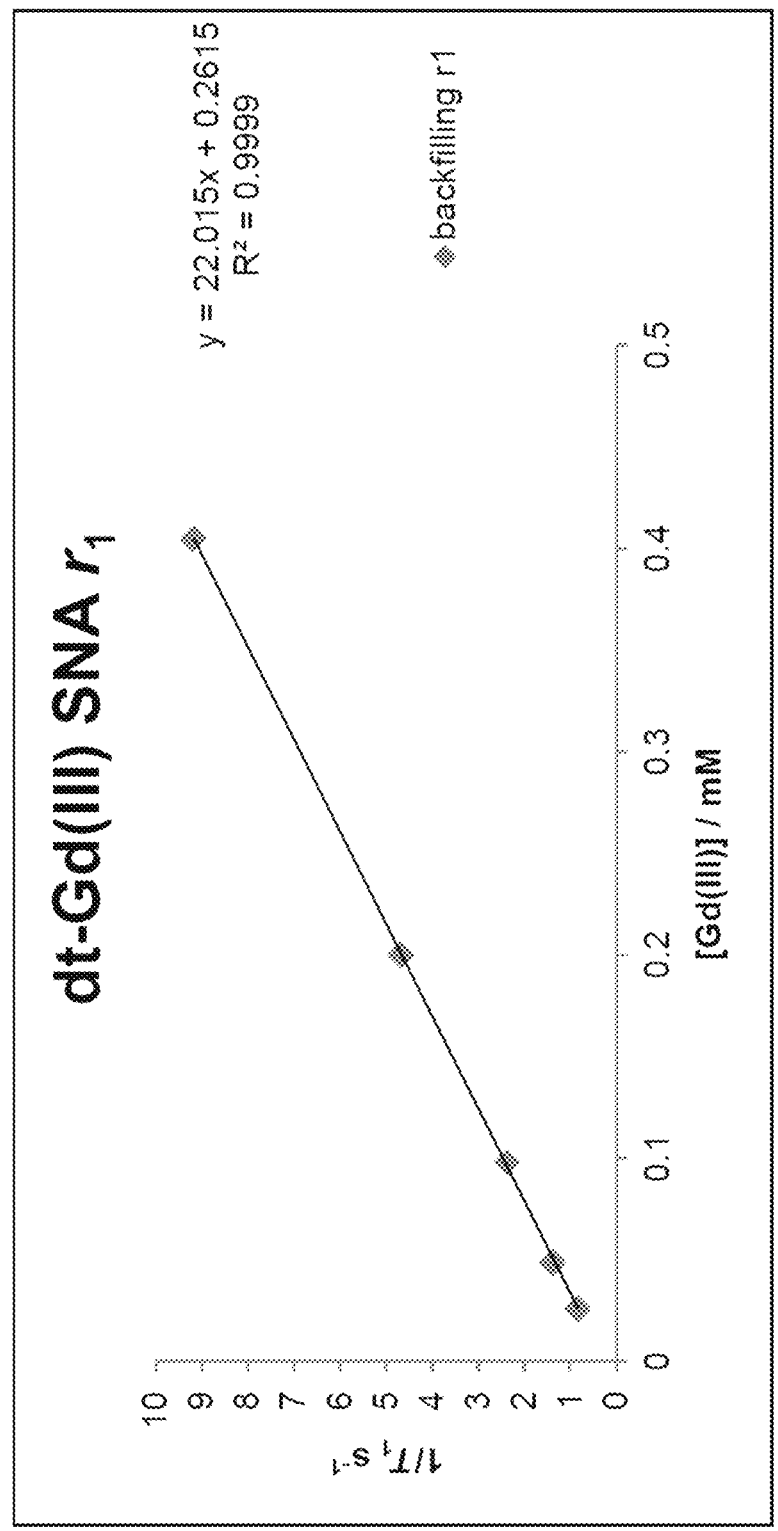
FIG. 7. Example of $r_1$ relaxivity calculation for dt-Gd(III) SNA conjugates.

A stock solution of backfilled dt-Gd(III) SNA conjugates was made (700 uL). This stock was serially diluted four times for a total of five solutions. Solutions were heated to 37° C. and two hundred μL of each concentration was placed into a Bruker minispec mq60 NMR spectrometer (60 MHz) for measurement of $T_1$ relaxation time. Data were collected using an inversion recovery pulse sequence using 4 averages, a 15 s repetition time and 10 data points. The remaining volumes of each solution were utilized for ICP analysis of [Gd(III)]. The inverse of the longitudinal relaxation time ($1/T_{1, s^{-1}}$) was plotted versus the Gd(III) concentration (mM). By applying a linear fit to this data, the slope that is generated is defined as the relaxivity of the agent (mM$^{-1}$ s$^{-1}$). Relaxivities of DNA-Gd@spheres, Gd(III)-DNA and complex 5 were collected by the analogous procedure (Table 3, FIG. 7).

Oligonucleotide Synthesis

Synthesis of oligonucleotides was performed on 3' disulfide C3 controlled pore glass beads (Glen Research). The 24mer poly-dT oligonucleotide were made using standard reagents with the single 5' modification added via the use of Cy3 phosphoramidite (Glen Research). Deprotection of the oligonucleotide from the solid phase was performed using standard 1:1 AMA conditions (ammonium hydroxide:methylamine) at 55° C. for one hour. Strands were filtered away from CPGs and purified by reverse phase HPLC and characterized by MS-MALDI. (m/z) observed: 7998, calculated: 7991 [M–H]$^-$. DNA used for synthesis of Gd(III)-DNA utilized the standard reagents from above, but included the use of amino modifier C6 dT (Glen Research), indicated as T*, and Cy3 phosphoramidite (Glen Research). The synthesized oligonucleotide consisted of the sequence 3'-S-S-TTT-TTT-TTT-TTT-T*TT-T*TT-T*TT-T*TT-Cy3-5' (SEQ ID NO: 1).

TABLE 3

Measured values of T1 and corresponding [Gd(III)] measured by ICP-MS for dt-Gd(III) SNAs.

| sample | [Gd]/mM | $T_1$ (ms) | $T_1$ (s) | $1/T_1$ |
|---|---|---|---|---|
| 1 | 0.405 | 108.9 | 0.109 | 9.18 |
| 2 | 0.200 | 214.1 | 0.214 | 4.67 |
| 3 | 0.098 | 423.3 | 0.423 | 2.36 |
| 4 | 0.049 | 726 | 0.726 | 1.38 |
| 5 | 0.026 | 1203 | 1.203 | 0.83 |

Synthesis of Gold Nanoparticles

Gold nanoparticles were synthesized by citrate reduction of HAuCl$^-$, according to published procedures. The plasmon resonance wavelength was observed by UV/Vis spectroscopy and size was confirmed by DLS and TEM. Particle size was determined by analysis of over 200 particles using image J, and particle volumes and total gold content were approximated by the geometric formula for the volume of a sphere and the density of bulk gold, here resulting in a particle content of 67,881 gold atoms per AuNP.

Nanoconjugate Synthesis

Poly-dT SNA conjugates were made by first deprotecting DNA using dithiothreitol, followed by purification on a GE NAP 5 column, and subsequent addition to spherical 13.0±1.6 nm citrate capped gold nanoparticles. A standard synthesis was started by dissolution of 18.6 OD (260 nm) of DNA (corresponding to ~225 strands of DNA per nanoparticle) into 300 μL of 100 mM dithiothreitol in 180 mM (pH 8.0) phosphate buffer, and the solution was left to stir at room temperature for 1 hour. The DNA was then run through a pre-packed G25 sephadex column (NAP-5, GE life sciences) using 180 mM phosphate buffer as the eluent, monitoring clearance of the column visually by observation of the Cy3 dye on the DNA. To 32 mL of 13.3 nM nanoparticles in water is added 34.8 μL of tween 20 (for a total concentration of 0.01% v/v) and deprotected and purified DNA in 0.7 mL 180 mM phosphate buffer. The solution is then sonicated for 30 seconds and left to stir for 30 minutes. Over the subsequent five hours, a solution of NaCl (4.753 M), phosphate buffer (10 mM) and 0.01% tween 20 is added in increments of 805, 824, 843, 862 and 882 μL, on per hour, with each addition followed by 30 seconds of sonication. Within the intervening time, the mixture was left to stir at room temperature. The final concentration of NaCl was 600 mM. The solution was left to stir a further 48 hours. Purification of Poly-dT SNA conjugates was accomplished using three consecutive rounds of centrifugation (45 minutes at 15×g) and resuspension until no further visible dye remained in the supernatant. Particle concentration was determined by ICP-MS by examination of Au content. DNA content per particle was quantified by dissolution of gold nanoparticle cores and UV/Vis analysis of Cy3 content according to a standard curve. When not in use, particles are stored at 4° C. After synthesis and characterization, DLS measurements of all nanoconjugates were conducted. Zeta-potential of bare nanostars and spheres was measured in millipore water. After Gd(III)-DNA conjugation, zeta-potential was measured in 1×DPBS (Gibco) to characterize the surface charge under physiological salt conditions.

Poly dT Particle Loading

Figure 8:
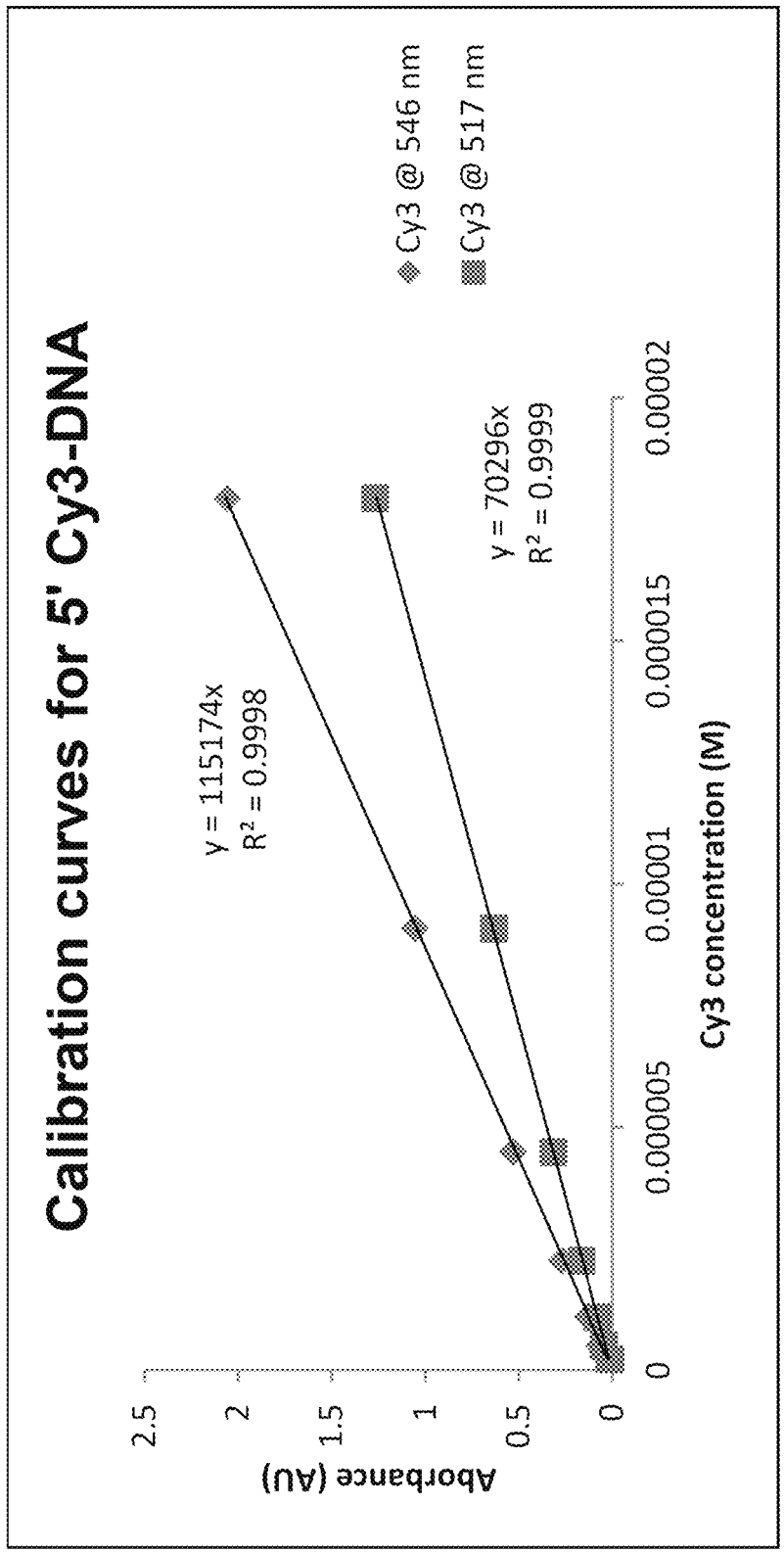
FIG. 8. Calibration curves for Cy3 fluorophore used to calculate DNA loading.

For the purposes of quantifying fluorescently labeled DNA loading on SNAs bearing without Gd(III), a calibration curve was made which was standardized to Cy3-Gd(III)-DNA, where the stoichiometric ratio of Gd(III) to DNA is 5:1. Specifically, an aliquot of DNA-Gd@spheres containing 677.5 nM particle, with a concentration 331.5 μM Gd(III), was diluted into 70 uL of solution containing 3.6 equivalents of potassium cyanide (roughly double of the molar ratio necessary for where 2 cyano groups coordinate per gold). Particles were allowed to digest at room temperature overnight until gold nanoparticle cores were completely digested. The concentration of KCN that should remain after complete dissolution of nanoparticle cores was calculated to 25 mM. All blanks, dilutions and subsequent unknowns were prepared such that the background concentrations amounted to 25 mM for standardization of conditions. From this stock of digested particles, 50 uL of solution was measured for UV/Vis absorbtion at 517 and 546 nm, and 50 uL were used to serially dilute for a further 6 concentrations. Aliquots (5 μL) of each solution used for UV/Vis absorbance were subsequently removed and digested for Gd(III) ICP analysis. Results were plotted as $\frac{1}{5}_{th}$ of Gd(III) concentration (due to the 5:1 stoichiometry between Gd(III) and Cy3) and analyzed by linear regression where the y-intercept is forced through zero (FIG. 8). Using a 38.9 nM aliquot of post purified poly-dT SNAs, a similar 3.6 equivalents of KCN was added from an aqueous 450 mM KCN stock (such that remaining KCN totaled 25 mM), and sample was left to digest overnight. The dilution factor applied to the initial gold concentration by addition of KCN was recorded and the absorbances observed for 517 and 546 nm were used to calculate the concentration of DNA per gold core (Table 4).

TABLE 4

Calibration data and calculation of Cy3-labled
oligonucleotide loading of poly-dT SNAs.
Calibration Curve Raw Data

| [Gd(III)]/ mM | [Cy3]/ mM | 517 nm Absorbance | 546 nm Absorbance |
|---|---|---|---|
| 0.0897 | 0.0179 | 1.266 | 2.058 |
| 0.0455 | 0.0091 | 0.632 | 1.056 |
| 0.0225 | 0.0045 | 0.313 | 0.530 |
| 0.0113 | 0.0023 | 0.160 | 0.270 |
| 0.0055 | 0.0011 | 0.077 | 0.133 |
| 0.0026 | 0.0005 | 0.041 | 0.068 |
| 0.0012 | 0.0002 | 0.009 | 0.022 |
| poly-dT SNAs | 0.0072 | 0.507 | 0.834 |

Kinetics of Backfilling

The particle loading resultant from the rate of backfilling were determined by performing a standard backfilling procedure while taking aliquots at specific time points. For accuracy, the standard purification procedure was used for each time point collected. Specifically, to 1 mL of 92.7 nM stock poly-dT SNAs DPBS was added 0.15 mg of complex 4 in aqueous 0.01% tween20. After 60 minutes, an aliquot of 100 µL was removed and diluted into 900 µL of DPBST (0.01% tween20). This solution was centrifuged for 45 minutes, (4° C., 15×g), and the supernatant removed. This process was repeated once more before the final diluted solution was analyzed by ICP for Gd(III)/Au content. This procedure was repeated as described for each of the remaining time points.

Nanoconjugate Stability

The colloidal stability of the dt-Gd(III) SNAs and DNA-Gd@spheres were measured under a range of cell culture related conditions over a period of 14 days at 37° C. The experiment was conducted by diluting stocks of dt-Gd(III) SNAs and DNA-Gd@spheres into 1 mL of each of PBS, DMEM, 10% FBS/DMEM and 100% FBS in a sterile environment. Each set of conditions was run in duplicate. At the time point specified, aliquots were taken from each tube and analyzed for colloidal stability by measurement of the maximum surface plasmon absorbance peak (FIGS. 4A-F and Tables 5 and 6), and then centrifuged to remove gold. From these tubes was then removed an aliquot of supernatant to analyze Gd(III) content which was lost from the surface of the particles using ICP-MS. Gd(III) particle loading was quantified at time 0 for each condition, and the supernatant analysis data is reported as a percentage of Gd(III) present therein (necessarily lost from the particle surface) over the course of 14 days. Through the course of the experiment, each of the samples was stored in an incubator set to 37° C.

TABLE 5

Maximum surface plasmon resonance absorbance peaks
for dt-Gd(III) SNAs over 14 days.
Colloidal stability of dt-Gd(III) SNAs ($\lambda_{max}$)

| Timepoint | PBS (nm) | DMEM (nm) | 10% FBS (nm) | FBS (nm) | water (nm) |
|---|---|---|---|---|---|
| time 0 | 523 | 528 | 529 | 528 | 527 |
| day 1 | 526 | — | 526 | 526 | — |
| day 7 | 521 | — | 529 | 529 | — |
| day 14 | 520 | — | 529 | 533 | — |

TABLE 6

Maximum surface plasmon resonance absorbance
peaks for DNA-Gd@spheres over 14 days.
Colloidal stability of DNA-Gd@spheres ($\lambda_{max}$)

| Timepoint | PBS (nm) | DMEM (nm) | 10% FBS (nm) | FBS (nm) | water (nm) |
|---|---|---|---|---|---|
| time 0 | 525 | 522 | 523 | 528 | 521 |
| day 1 | 522 | — | 526 | 528 | — |
| day 7 | 521 | — | 529 | 529 | — |
| day 14 | 521 | — | 531 | 531 | — |

Example 3

Figure 9A:
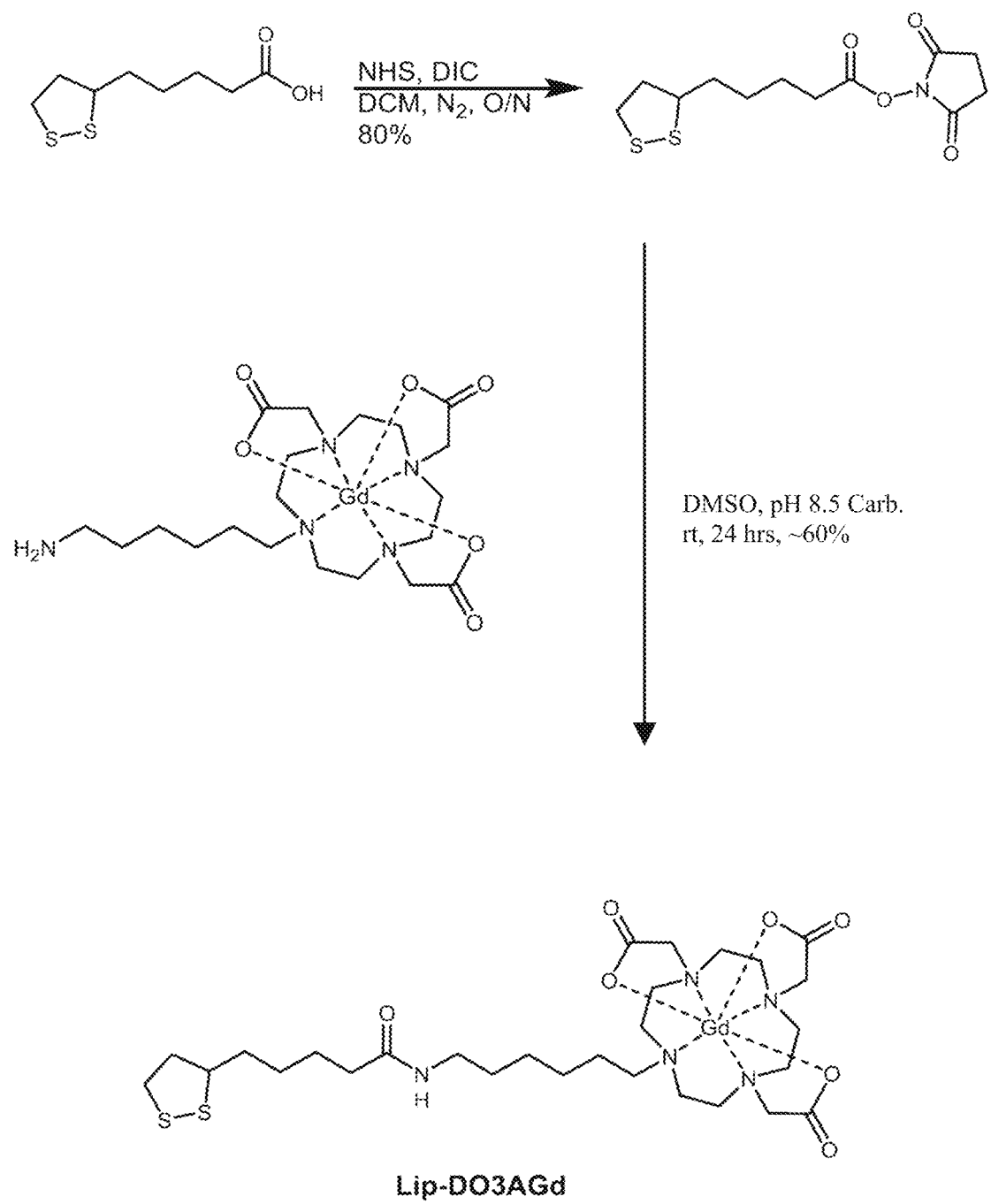
FIGS. 9A-B. Synthesis of Lip-DO3AGd and Lip-DT-PAGd. Lipoic acid converted to the lipoic NHS-ester using DIC as a coupling reagent in 80% yield. An amine-functionalized DO3A based Gd(III) complex containing a six-carbon linker was synthesized according to previous reported procedures. Subsequent peptide conjugation to the lipoic NHS-ester was performed in 1:1 DMSO:pH 8.5 carbonate buffer to form Lip-DO3AGd and purified by reverse-phase HPLC in 60% yield. Similarly, an amine functionalized DTPA based Gd(III) complex with a four-carbon linker was synthesized according to previous reported procedures. Similar peptide couple conditions with the lipoic NHS-ester was performed to form Lip-DTPAGd and purified by reverse-phase HPLC in 60% yield.
Figure 9B:
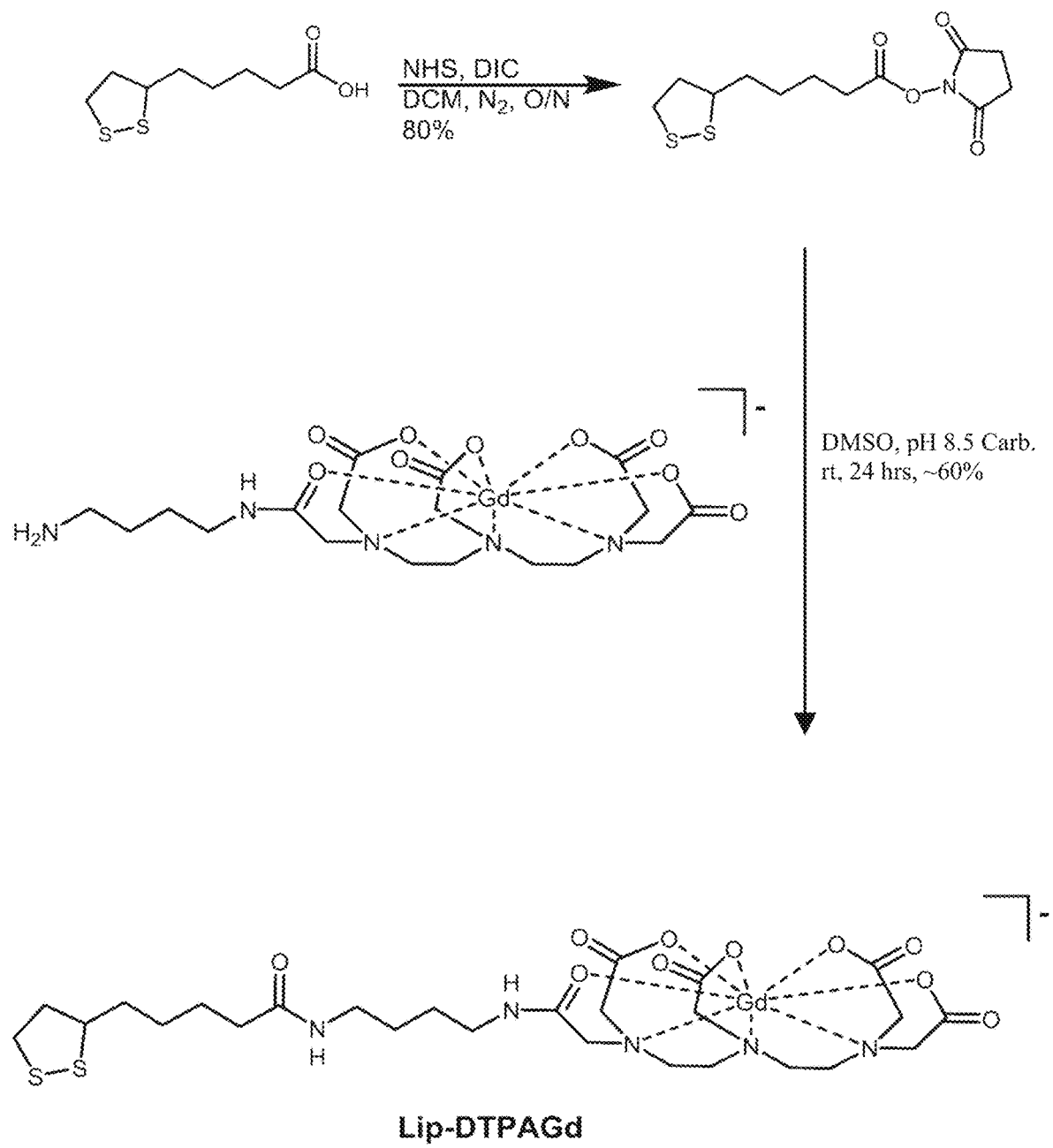

Pancreatic Tissue Labeling for MRI with Gd(III)-Dithiolane Gold Nanoparticles—Results Synthesis and Characterization of Lip-Gd@AuNPs The modification of two Gd(III) CAs was performed to investigate the Lip-Gd@AuNP system. An amine-functionalized DO3A based Gd(III) complex containing a six-carbon linker was synthesized according to previous reported procedures.[22] Subsequent peptide conjugation to the lipoic NHS-ester was performed in 1:1 DMSO:pH 8.5 carbonate buffer to form Lip-DO3AGd and purified by reverse-phase HPLC in 60% yield (FIG. 9A). Similarly, an amine functionalized DTPA based Gd(III) complex with a four-carbon linker was synthesized according to previous reported procedures. Similar peptide couple conditions with the lipoic NHS-ester was performed to form Lip-DTPAGd and purified by reverse-phase HPLC in 60% yield (FIG. 9B).

Figure 10:
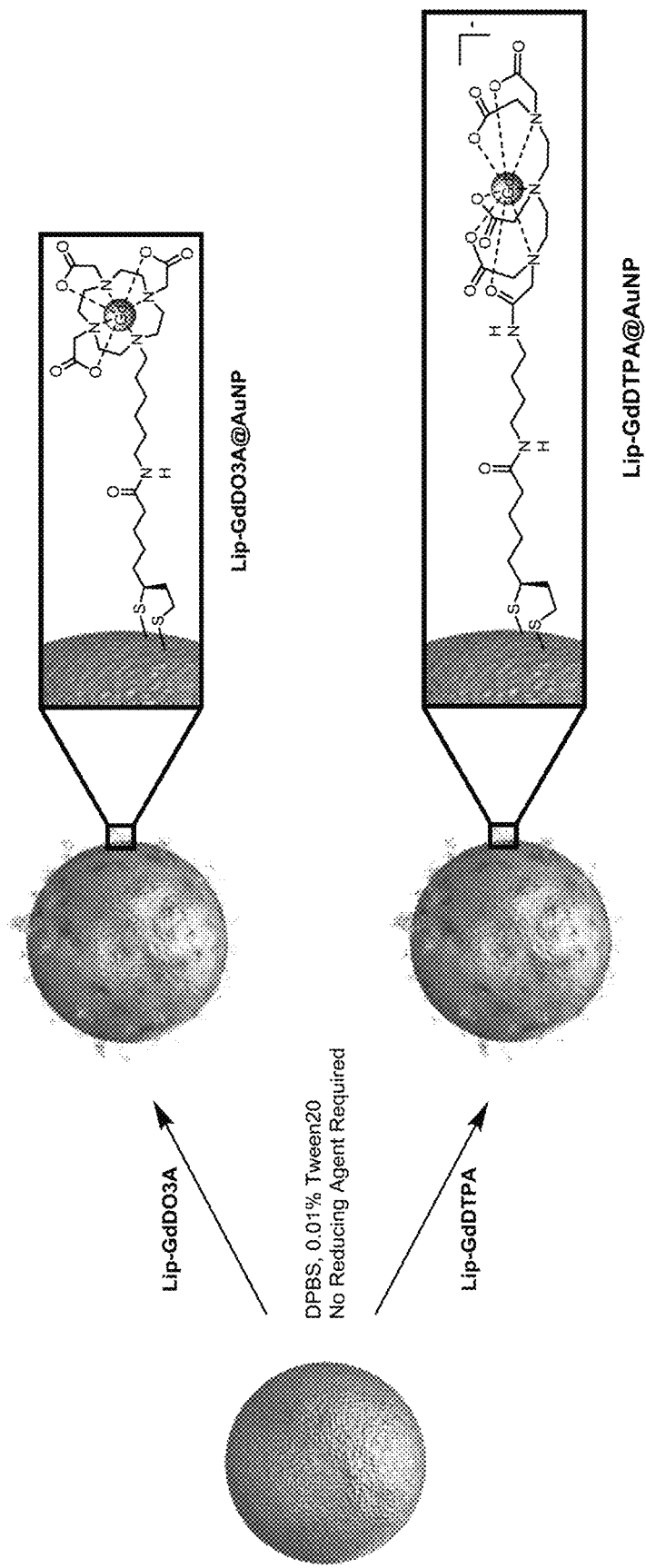
FIG. 10. Functionalization of the citrate stabilized AuNPs with Lip-DO3AGd and Lip-DTPAGd was performed through facile thiol-gold chemistry. The complexes, Lip-DO3AGd and Lip-DTPAGd, were dissolved in 500 μL of methanol and 500 μL of Milli-Q water, added to 25 mL of 10 nM AuNPs with 0.01% Tween 20 (v/v), and shaken overnight for the formation of Lip-DO3AGd@AuNP and Lip-DTPAGd@AuNP, respectively. Notably, functionalization of the AuNP surface is achieved without the addition of a reducing agent. The functionalized AuNPs, Lip-DO3AGd@AuNP and Lip-DTPAGd@AuNP.

Citrate stabilized spherical AuNPs were fabricated using the Frens protocol. The diameter of the particles was determined to be 17.2±2.1 nm via analysis of images obtained by transmission electron microscopy (TEM) and dynamic light scattering (DLS). Functionalization of the citrate stabilized AuNPs with Lip-DO3AGd and Lip-DTPAGd was performed using 25 mL of 10 nM AuNPs with 0.01% Tween 20 (v/v). The complexes, Lip-DO3AGd and Lip-DTPAGd, were dissolved in 500 µL of methanol and 500 µL of Milli-Q water, added to the AuNP solution, and shaken overnight for the formation of Lip-DO3AGd@AuNP and Lip-DTPAGd@AuNP, respectively (FIG. 10). Notably, functionalization of the AuNP surface is achieved without the addition of a reducing agent. The functionalized AuNPs, Lip-DO3AGd@AuNP and Lip-DTPAGd@AuNP, were purified using ultra-centrifugation. Five rounds of centrifugation at 21.1×g (20 min, 7° C.) were performed to sediment the particles. Following each round of centrifugation, the top solution was subsequently decanted, and the particles were resuspended in Dulbecco's phosphate buffered saline (DPBS) with 0.01% Tween 20. The particles were concentrated down to 250 nM AuNPs as a 1 mL stock solution in DPBS 0.01% Tween 20. When not in use, particles were stored at 4° C.

Gd(III) Loading and Relaxivity of Lip-Gd@AuNPs

To quantify Gd(III) loading, inductively coupled plasma mass spectrometry (ICP-MS) was used to determine the ratio of Gd(III) to Au. Lip-DO3AGd@AuNP contained 2,375±81 Gd(III) complexes per AuNP, corresponding to a packing density of 2.54±0.13 Gd(III) chelates per $nm_2$ of AuNP surface. In comparison, Lip-DTPAGd@AuNP contained 1,477±47 Gd(III) complexes per AuNP, corresponding to a packing density of 1.58±0.09 Gd(III) chelates per $nm_2$ of AuNP surface. The loading of Lip-DO3AGd@AuNP and Lip-DTPAGd@AuNP represents greater than a threefold and two-fold respective increase in Gd(III) payload and packing density relative to previously reported DNA-Gd@AuNP (Table 7). This phenomenon is attributed to the inefficient packing of polyvalent DNA-Gd(III) conjugates on the surface of the AuNP relative small molecular Gd(III) chelates; although embodiments herein are not limited to any particular mechanism of action and an understanding of the mechanism of action is not necessary to practice such embodiments. Surface packing density between Lip-DO3AGd@AuNP and Lip-DTPAGd@AuNP is attributed to the charge and steric bulk of the Gd(III) chelate—the negative charge of Lip-DTPA limits surface packing due to electrostatic repulsion.

TABLE 7

Gd(III) loading characterization of Lip-DO3AGd@AuNPs and Lip-DTPAGd@AuNPs.

|  | Loading Gd/AuNS | Coverage Gd/nm² |
| --- | --- | --- |
| Lip-GdDO3A@AuNP | 2,375 ± 81 | 2.54 ± 0.13 |
| Lip-GdDTPA@AuNP | 1,477 ± 47 | 1.58 ± 0.09 |
| DNA-Gd@AuNP[12] | 564 | 0.8 |

To assess the performance of Lip-Gd@AuNPs, the $r_1$ of the Lip-DO3AGd@AuNP and Lip-DTPAGd@AuNP was determined by taking the slope of the linear plot of $1/T_1$ vs. Gd(III) concentration at low field (1.5 T) and high field (7 T). Lip-DO3AGd@AuNP was observed to have an ionic $r_1$ of 14.6±0.7 and 4.0±0.1 mM$^{-1}$s$^{-1}$ at 1.5 and 7 T, respectively. Based on particle loading of Lip-DO3A@AuNP, this yields a per particle $r_1$ of 34,675±2040 and 9,500±402 mM$^{-1}$s$^{-1}$ at 1.5 and 7 T, respectively. In comparison, Lip-DTPAGd@AuNP was observed to have an ionic $r_1$ of 13.7±0.8 and 4.7±0.2 mM$^{-1}$s$^{-1}$ at 1.5 and 7 T, respectively. Based on particle loading of Lip-DTPA@AuNP, this yields a per particle $r_1$ of 20,235±1346 and 6,942±369 mM$^{-1}$s$^{-1}$ at 1.5 and 7 T, respectively. The ionic relaxivity is comparable to previously reported DNA-Gd@AuNPs with an $r_1$ of 14.6 mM$^{-1}$s$^{-1}$ (Table 8). The ionic $r_1$ values of both Lip-DO3AGd@AuNP and Lip-DTPAGd@AuNP reflect an increase in relaxivity due to an increase in the rotational correlation time, $\tau_r$, from conjugation to the AuNP surface by ultimately slowing the Gd(III) reorientation time.

TABLE 8

Relaxivities of Lip-DO3AGd@AuNPs and Lip-DTPAGd@AuNPs at 1.5 and 7 T. 'Ionic' r1 refers to the contribution of each individual Gd(III) complex to proton relaxation, whereas 'particle' describes the product of each particle's payload and ionic r1.

|  | $r_{1,\ ionic}$ (mM$^{-1}$s$^{-1}$) @ 1.5 T | $r_{1,particle}$ (mM$^{-1}$s$^{-1}$) @ 1.5 T | $r_{1,ionic}$ (mM$^{-1}$s$^{-1}$) @ 7 T | $r_{1,particle}$ (mM$^{-1}$s$^{-1}$) @ 7 T |
| --- | --- | --- | --- | --- |
| Lip-GdDO3A@AuNP | 14.6 ± 0.7 | 34,675 ± 2040 | 4.0 ± 0.1 | 9,500 ± 402 |
| Lip-GdDTPA@AuNP | 13.7 ± 0.8 | 20,235 ± 1346 | 4.7 ± 0.2 | 6,942 ± 369 |
| DNA-Gd@AuNP | 14.6 | 8,234 | 5.8 | 3,271 |

In Vivo Studies of Lip-Gd@AuNPs

Male C-57 black mice (wild type) were acquired from Charles River (Wilminton, Mass.), and were housed under pathogen free conditions. Animal studies were conducted at Northwestern University in accordance with the National Institutes of Health Guide for the Care and Use of Laboratory Animals and established institutional animal use and care protocols. Animals were injected with 4.0 nmol/kg body weight of AuNPs through IP administration. For Lip-DO3AGd@AuNPs and Lip-DTPAGd@AuNPs, this equates to 9.0 and 5.5 μmol/kg body weight of Gd(III), respectively. After 24 h, organs were harvested, and quantification of Gd(III) and Au was performed using ICP-MS. The total μg of Gd(III) and Au per gram of tissue was measured, respectively.

Figure 11A:
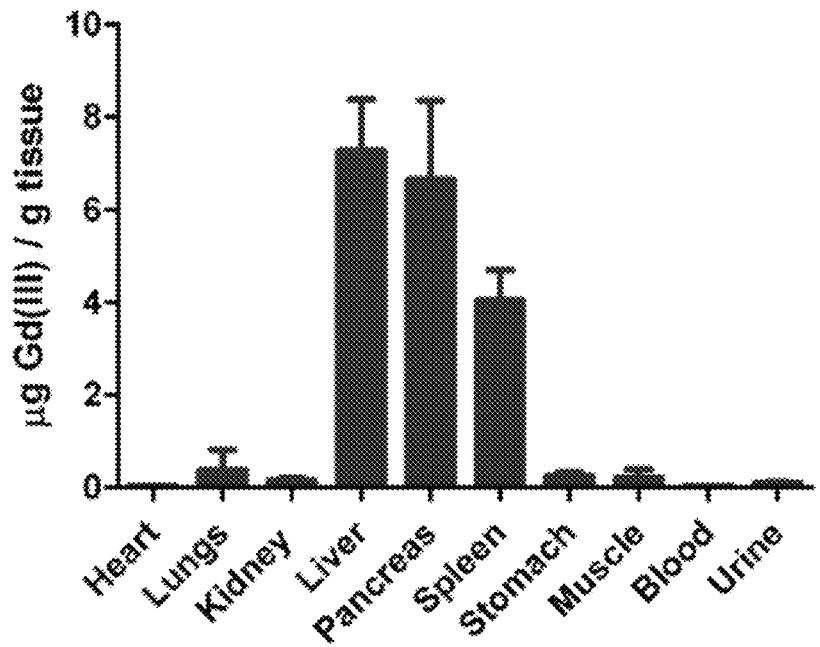
FIGS. 11A-B. Biodistribution of Lip-DO3AGd@AuNPs in C-57 mice. Following IP administration and 24 h incubation, organs were harvested and metal analysis was conducted via ICP-MS to determine the amount of Gd(III) (A) and Au (B) per g of organ. Lip-DO3AGd@AuNPs accumulate in the clearance organs, liver and spleen, and accumulates in the pancreas.
Figure 11B:
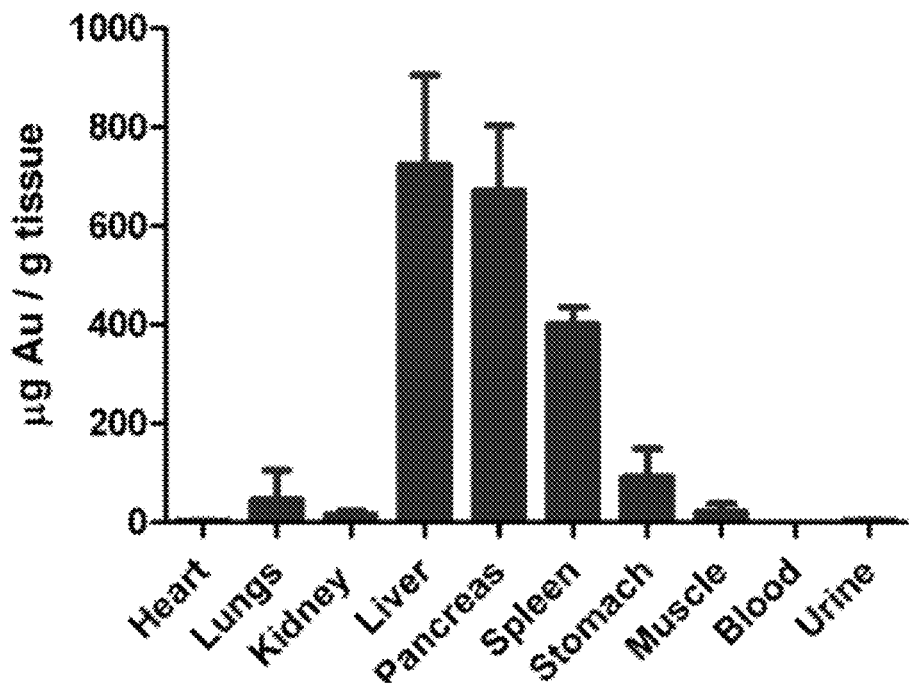
Figure 12A:
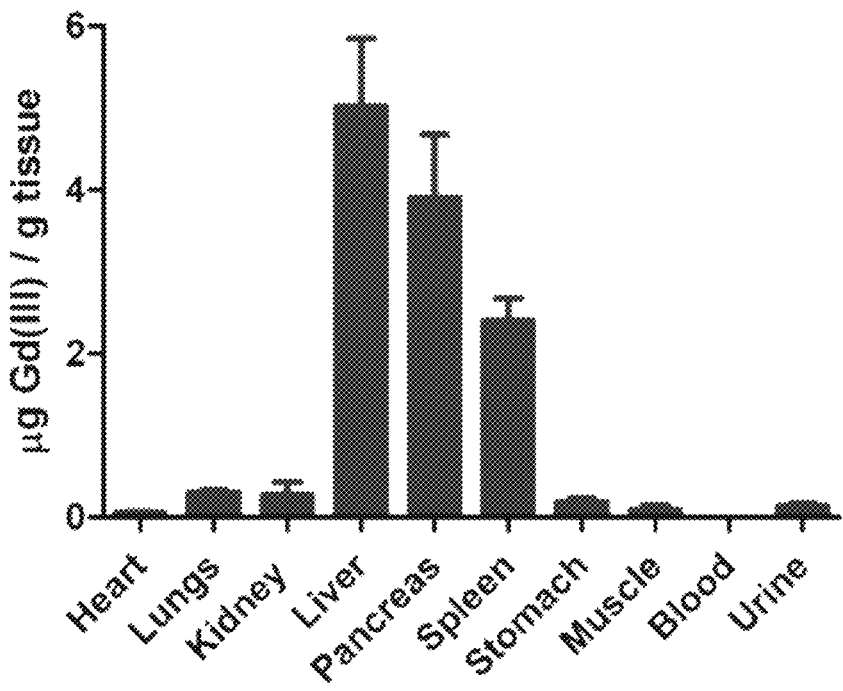
FIGS. 12A-B. Biodistribution of Lip-DTPAGd@AuNPs in C-57 mice. Following IP administration and 24 h incubation, organs were harvested and metal analysis was conducted via ICP-MS to determine the amount of Gd(III) (A) and Au (B) per g of organ. Lip-DTPAGd@AuNPs accumulate in the clearance organs, liver and spleen, and accumulates in the pancreas.
Figure 12B:
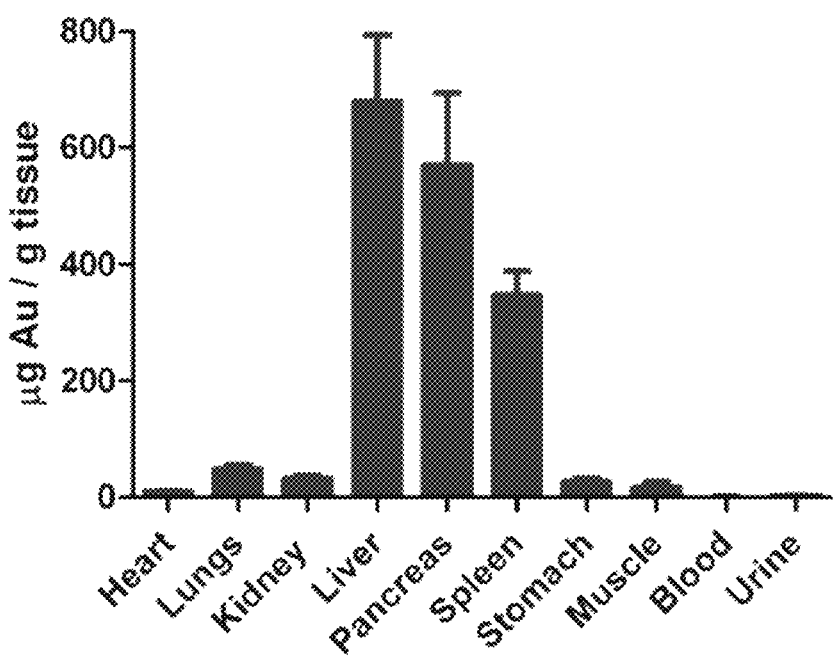

AuNP accumulation and biodistribution of Lip-DO3AGd@AuNPs and Lip-DTPAGd@AuNPs were similar (FIGS. 11 and 12). Significant accumulation in the liver and spleen (~700 and ~400 μg of Au per g of tissue, respectively) was observed for Lip-DO3AGd@AuNPs and Lip-DTPAGd@AuNPs. The high levels of AuNPs found in the liver and spleen indicate that reticuloendothelial system (RES) is the dominant mode of clearance for these particles. Furthermore, significant accumulation to the pancreas was observed (~650 μg of Au per g of tissue) for both Lip-DO3AGd@AuNPs and Lip-DTPAGd@AuNPs. Indeed, the levels of accumulation of Gd(III) in the pancreas reflects the Gd(III) loading of Lip-DO3AGd@AuNPs and Lip-DTPAGd@AuNPs with ~7 and ~4 μg of Gd(III) per g of tissue, respectively.

Figure 13B:
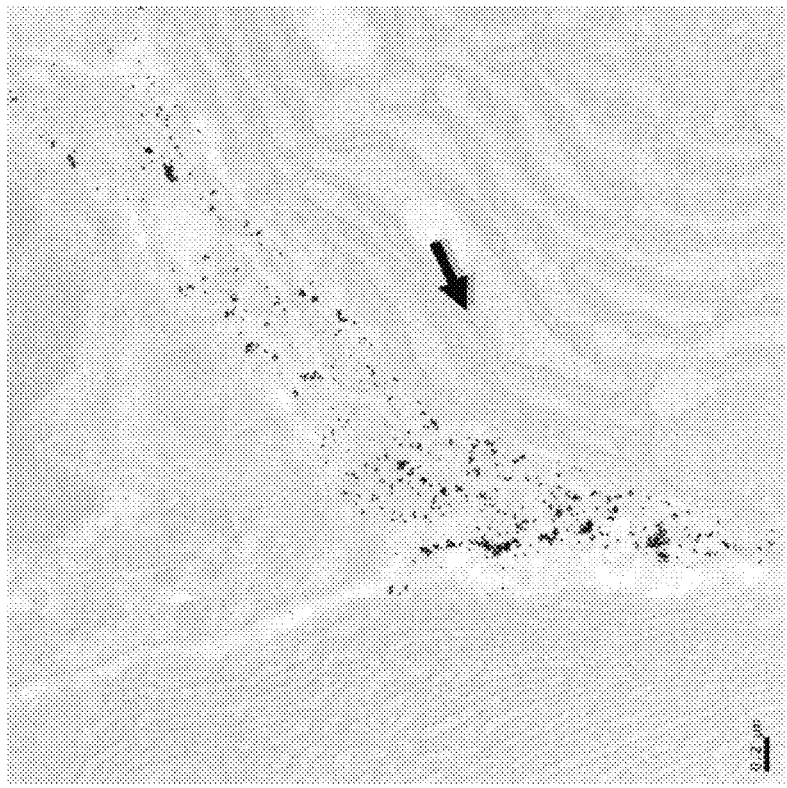
FIGS. 13A-B. TEM images of pancreatic tissue from a mouse treated with Lip-DO3AGd@AuNPs. Particles are present (as black spheres) in (A) large (1 μm) lysosomes as particle aggregates and (B) the interstitial spaces in acrine cells as identified by the extensive ER organelles (black arrow).
Figure 13A:
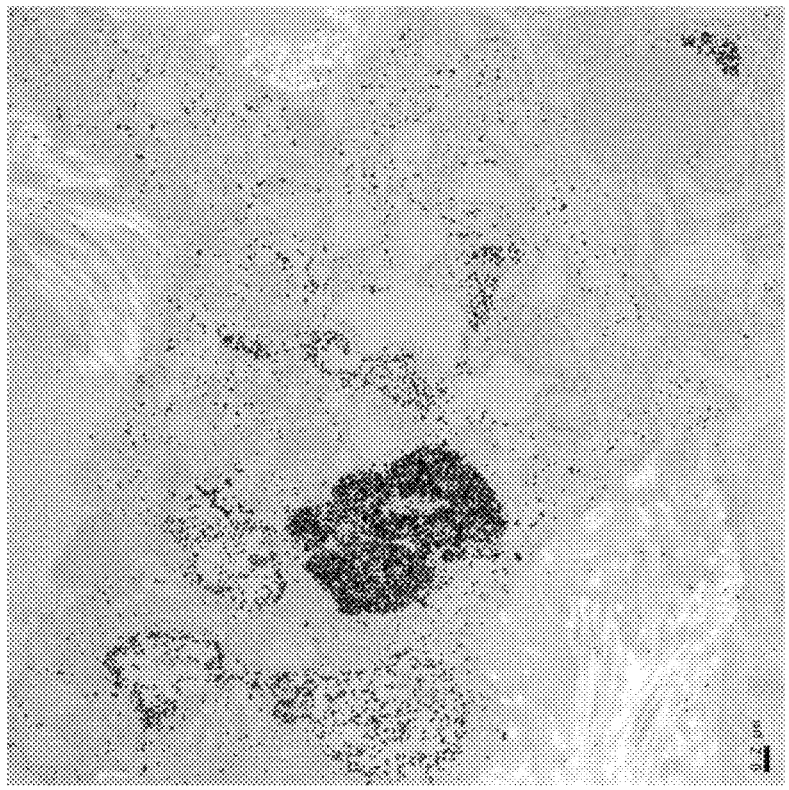
Figure 14:
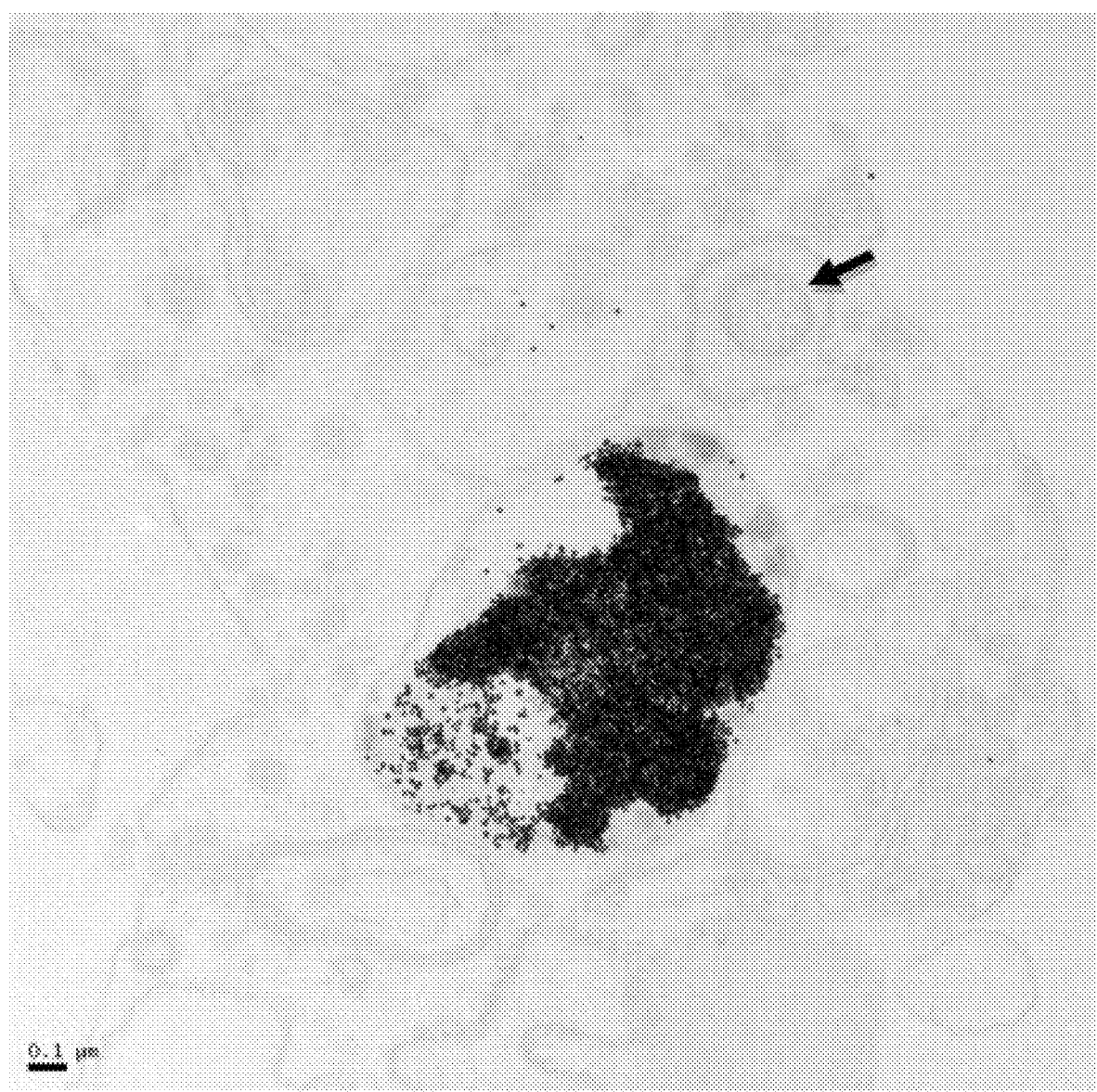
FIG. 14. TEM image of pancreatic tissue from a mouse treated with Lip-DTPAGd@AuNPs. Particles are present in large (1 μm) lysosomes as particle aggregates in an islet cell as identified by the presence of insulin granules (black arrow).

In an effort to validate the accumulation of Lip-Gd@AuNPs to the pancreas, TEM and histology were performed for the pancreas of one mouse following 24 h incubation with Lip-DO3AGd@AuNPs and Lip-DTPAGd@AuNPs, respectively. Immediately following harvesting of the pancreas, the tissue was divided in two and fixed in formalin. The tissue was then separately prepared for sectioning for TEM and Histology. TEM images of pancreatic tissue slices revealed the presence of AuNPs in both animals incubation with Lip-DO3AGd@AuNPs and Lip-DTPAGd@AuNPs. Significant presence of individual Lip-DO3AGd@AuNPs was observed in the interstitial spaces between acrine cells of the pancreatic tissue (FIGS. 13A-B). The identification of the acrine cells were based on the presence of extensive endoplasmic reticulum (ER) organelles, as they are indicative of this particular pancreatic cell type. Similarly, the presence of Lip-DTPAGd@AuNPs was observed in the interstitial spaces of acrine cells. However, large particle aggregates of Lip-DPTAGd@AuNPs were observed to be encapsulated in lysosomes of pancreatic islet cells (FIG. 14). Although this particular particle accumulation was only observed in animals incubated with Lip-DPTAGd@AuNPs, the similar cellular localizing behavior maybe occurring for Lip-DO3AGd@AuNPs, and was simply not present in the tissue section.

Figure 15:
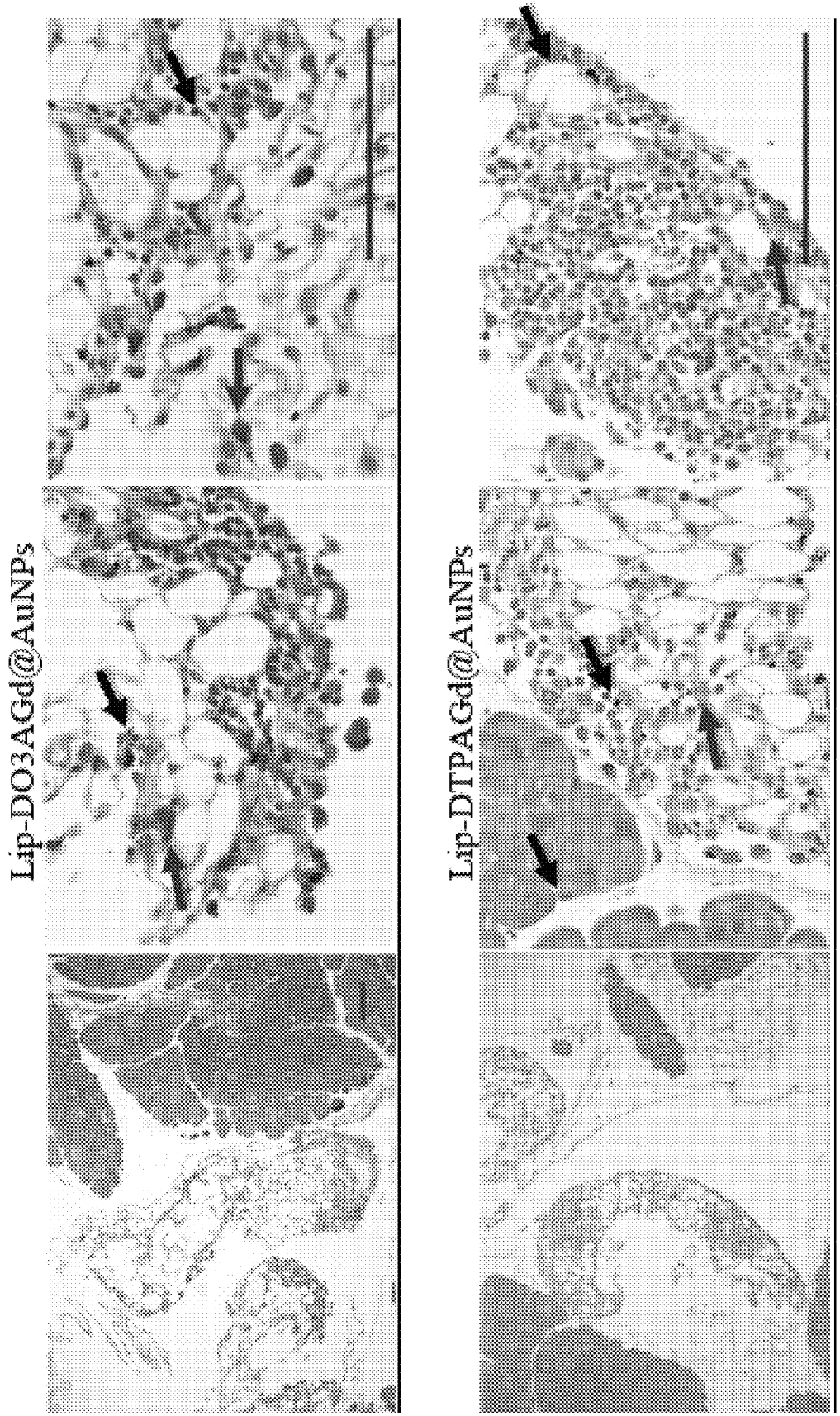
FIG. 15. Histology reveal mild inflammatory foreign material reaction in the adjacent tissue of the pancreas. The low magnification images on the left panel showed Lip-DO3AGd@AuNPs and Lip-DTPAGd@AuNPs labeled pancreatic tissue and the adjacent fatty tissues. No structural and morphological abnormalities were noted in neither of the two pancreas. However, slight inflammation was noted in the adjacent fatty tissues. Under the high power magnification, black nanoparticles are diffusely distributed in the fatty and pancreatic tissue (black arrows) of both pancreas slices. The inflammatory cells include lymphocytes and histocytes, some with phagocytic nanoparticles (red arrows). (H&E, Left, ob.x4; Middle and Right, ob.x60 Scale bar: 100 μm).

Further confirmation of pancreatic tissue labeling by Lip-Gd@AuNPs were obtained through histology. The presence of AuNP aggregates are observed in hematoxylin and eosin stained pancreatic tissue sections for both animals incubated with Lip-DO3AGd@AuNPs and Lip-DTPAGd@AuNPs (FIG. 15). No structural and morphological abnormalities were noted in neither of the two pancreases. However, slight inflammation was noted in the adjacent fatty tissues. Under high power magnification (100×), black AuNP aggregates are diffusely distributed in the fatty tissue of both pancreas. The inflammatory cells include lymphocytes and histocytes, some with phagocytic nanoparticles. Furthermore, the tissue labeled with Lip-DTPAGd@AuNPs contains nanoparticle aggregates directly in the pancreatic tissue.

Figure 16B:
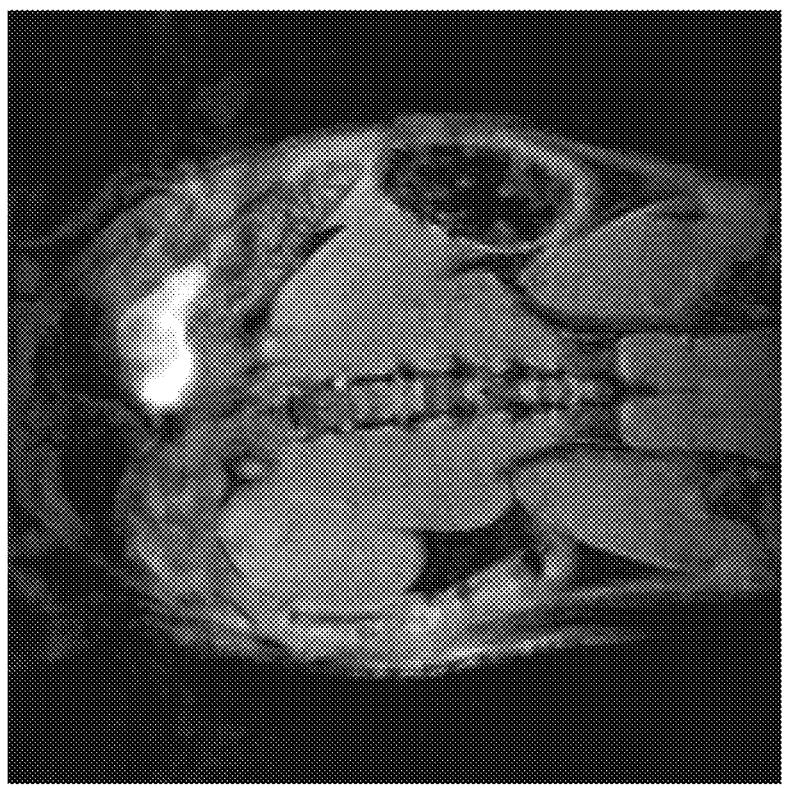
FIGS. 16A-B. Raw MRI images of paritineal cavity of C-57 mouse labeled with Lip-DO3AGd@AuNPs and Lip-DTPAGd@AuNPs, respectively. Particles were injected IP and incubated for 24 h prior to imaging. Pancreatic image contrast enhancement is observed for both Lip-DO3AGd@AuNP and Lip-DTPAGd@AuNP labeled mice. However, Lip-DTPAGd@AuNPs provide better image contrast enhancement of the pancreas, relative to Lip-DO3AGd@AuNPs.
Figure 16A:
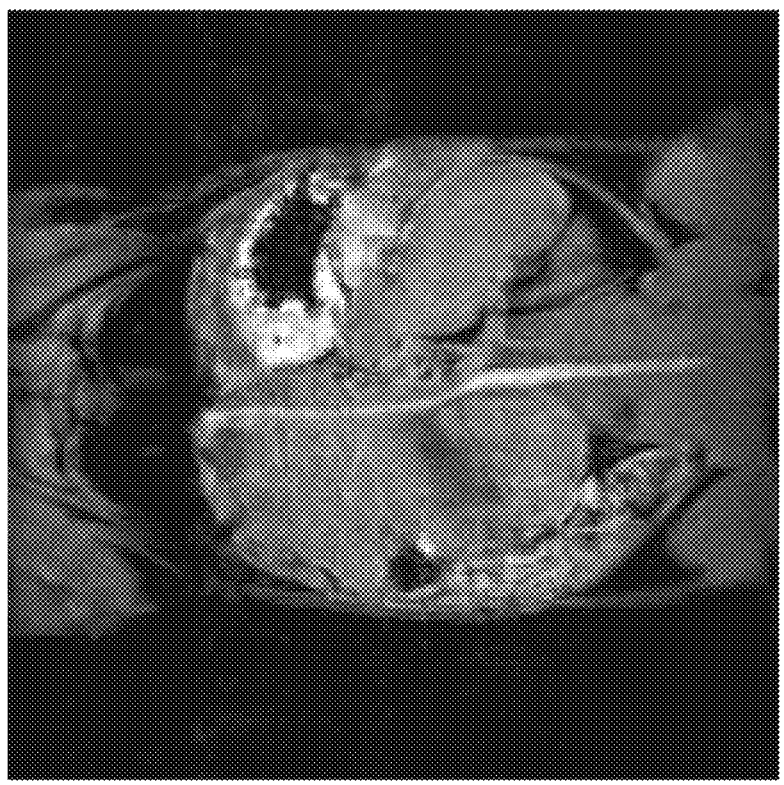

In vivo imaging of animals incubated with Lip-Gd@AuNPs was conducted to determine enhanced MR image contrast in pancreatic tissue. Following IP injection of Lip-DO3AGd@AuNPs and Lip-DTPAGd@AuNPs and 24 h incubation, MR images were acquired of the peritoneal cavity at 9.4 T using standard T1-weighted rapid acquisition rapid echo (RARE) scans. Increased contrast enhancement in the pancreas was observed for Lip-DO3AGd@AuNPs and Lip-DTPAGd@AuNPs (FIGS. 16A-B). While Lip-DO3AGd@AuNPs were able to provide modest contrast enhancement within the region of the pancreas, Lip-DTPAGd@AuNPs provided the most compelling contrast enhancement.

The biodistribution analysis of these agents suggests greater accumulation of Lip-DO3AGd@AuNPs in pancreatic tissue, relative to Lip-DTPAGd@AuNPs. However, the image contrast enhancement is observed to be greater for Lip-DTPAGd@AuNPs. It is contemplated the relaxivity of Lip-DO3AGd@AuNPs is diminished in vivo due to the endogenous presence of carbonate in biological milieu; although embodiments herein are not limited to any particular mechanism of action and an understanding of the mechanism of action is not necessary to practice such embodiments. The Lip-DO3AGd chelate has seven coordinating ligands that bind to the Gd(III) metal center, which provides two open coordination sites for bound water molecules (q=2). The cis nature of the two open coordination sites allow carbonate to coordinate to the Gd(III) metal center and effectively compete with water coordination (yielding a q=0 chelate). This capping of the Gd(III) metal center by carbonate may diminish the reflexivity of Lip-DO3AGd, and as a result decrease MR image contrast. In contrast, the Lip-DTPAGd chelate has eight coordinating ligands that permits one water molecule to bind to the Gd(III) metal center (q=1) and is not susceptible to carbonate binding.

Cellular Delivery of Lip-Gd@AuNPs

Figure 17:
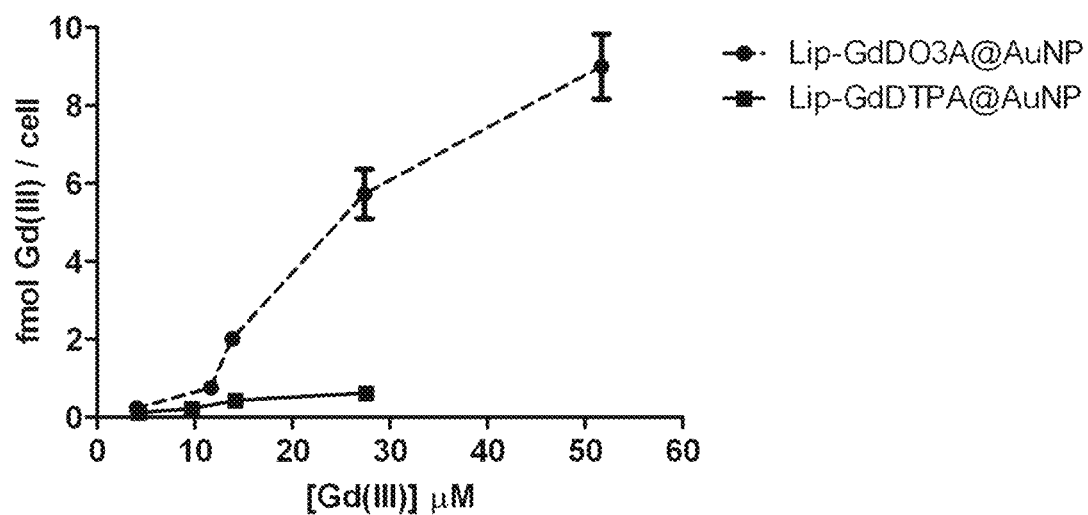
FIG. 17. Cell uptake for MDA-MB-231 Cherry cells following 24 h incubation with Lip-DO3AGd@AuNPs or Lip-DTPAGd@AuNPs, respectively. The Lip-DO3AGd@AuNPs achieved approximately ten times greater Gd(III) uptake over Lip-DTPAGd@AuNPs with 9.0 and 0.9 fmol of Gd(III)/cell, respectively.
Figure 18:
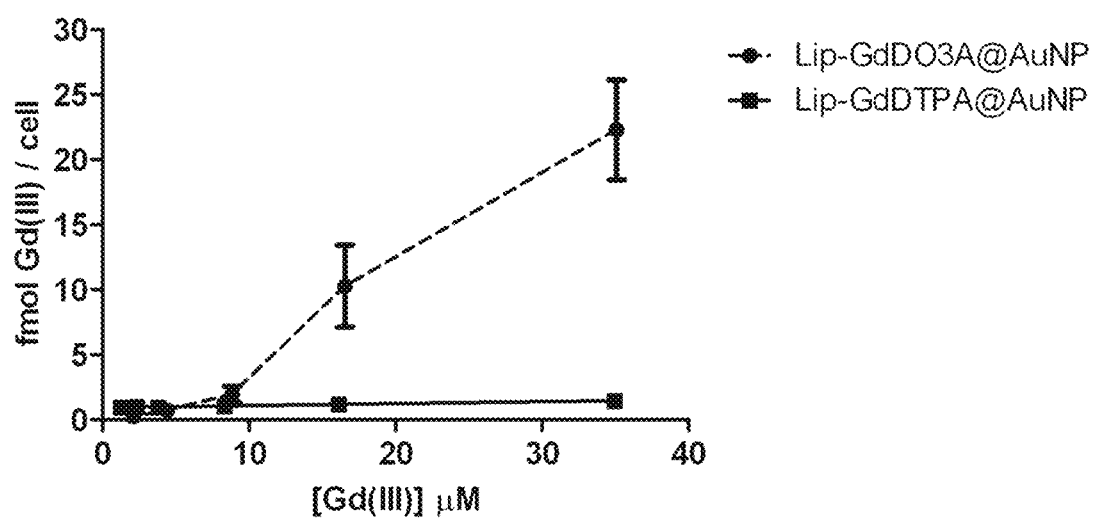
FIG. 18. Cell uptake for MDA-MB-231 Cherry cells following 72 h incubation with Lip-DO3AGd@AuNPs or Lip-DTPAGd@AuNPs, respectively. The Lip-DO3AGd@AuNPs achieved approximately ten times greater Gd(III) uptake over Lip-DTPAGd@AuNPs 20.0 and 2.0 fmol of Gd(III)/cell, respectively.
Figure 19:
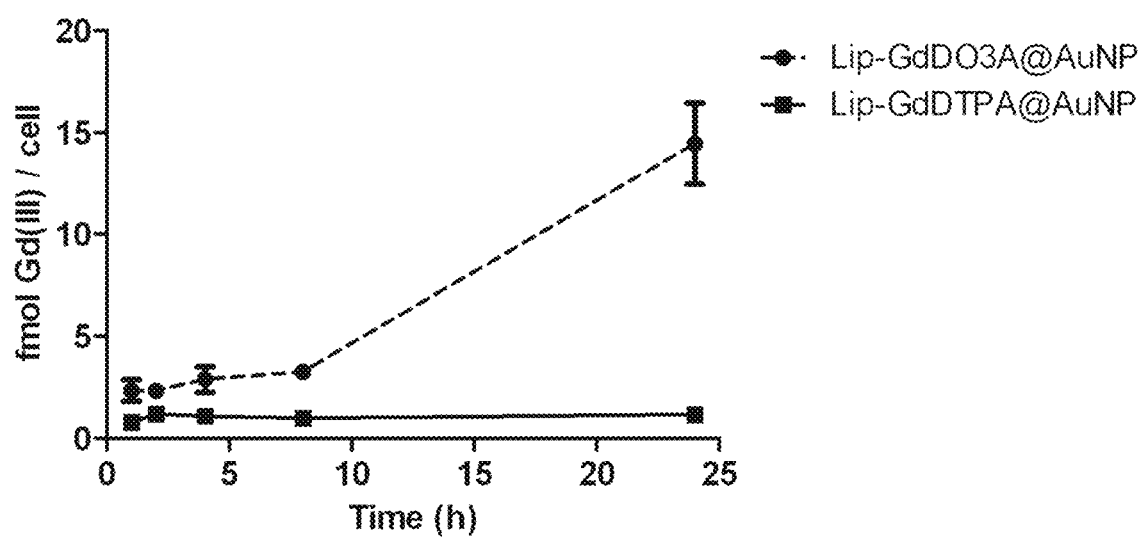
FIG. 19. Time-dependent uptake for the cellular delivery of Lip-DO3AGd@AuNPs and Lip-DTPAGd@AuNPs was performed with MDA-MB-231 Cherry cells. Cells were incubated with 50 μM of either Lip-DO3AGd@AuNP or Lip-DTPAGd@AuNP for 1, 2, 4, 8, and 24 hours at 37° C. The similar ten-fold increase in cell uptake of Gd(III) between Lip-DO3AGd@AuNPs and Lip-DTPAGd@AuNPs was observed (FIG. 17). However, the uptake of Lip-DTPAGd@AuNPs did not appear to be time-dependent—maximum cell uptake of was achieved within one hour. In contrast, the cell uptake of Lip-DO3AGd@AuNPs was time dependent. Significant increase in cell uptake of Lip-DO3AGd@AuNPs was observed between 8 and 24 h incubation, suggesting uptake occurs concurrently with cell division.
Figure 20A:
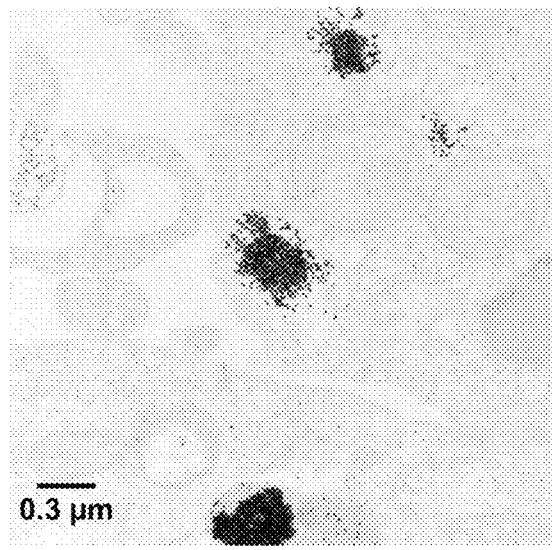
FIGS. 20A-D. TEM images of MDA-MB-231 Cherry cells following 24 h incubation with Lip-DO3AGd@AuNPs. Particles are present in large (0.5 m) lysosomes as particle aggregates (A and B). Lyosomes of particle aggregates are observed to be merging following endocytosis (C and D).
Figure 20B:
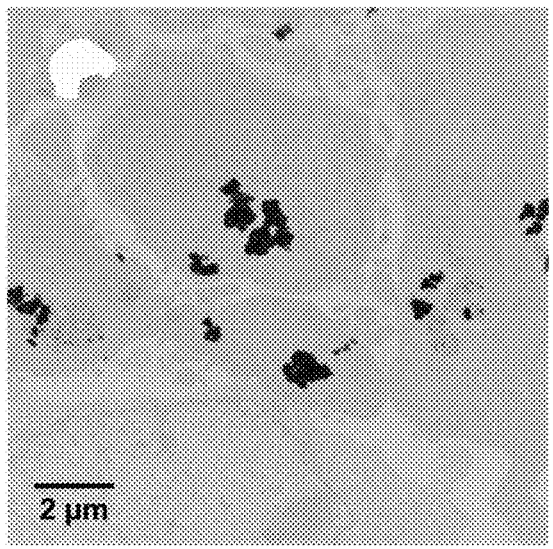
Figure 20C:
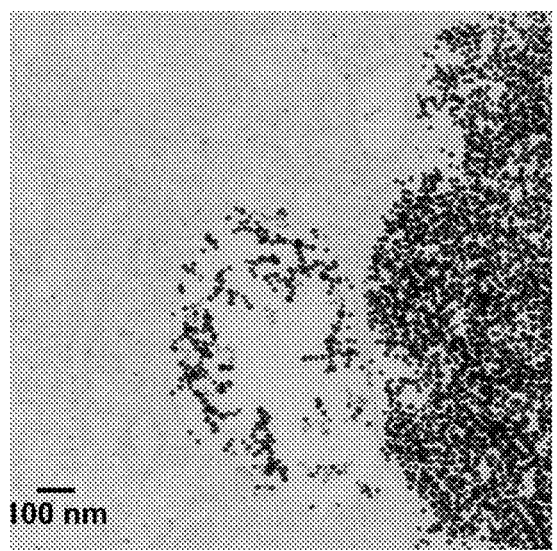
Figure 20D:
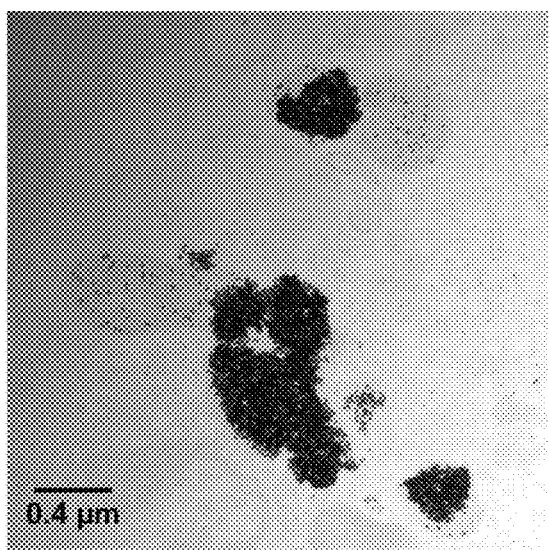
Figure 21A:
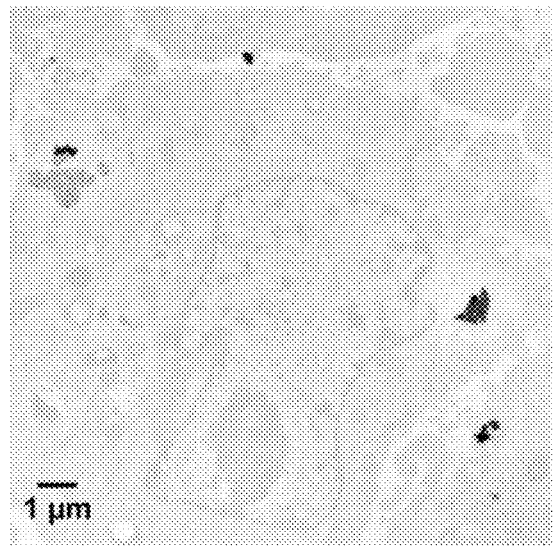
FIGS. 21A-D. TEM images of MDA-MB-231 Cherry cells following 24 h incubation with Lip-DTPAGd@AuNPs. Particles are present in large (0.5 m) lysosomes as particle aggregates (A and B). Lyosomes of particle aggregates are observed to be merging following endocytosis (C and D).
Figure 21B:
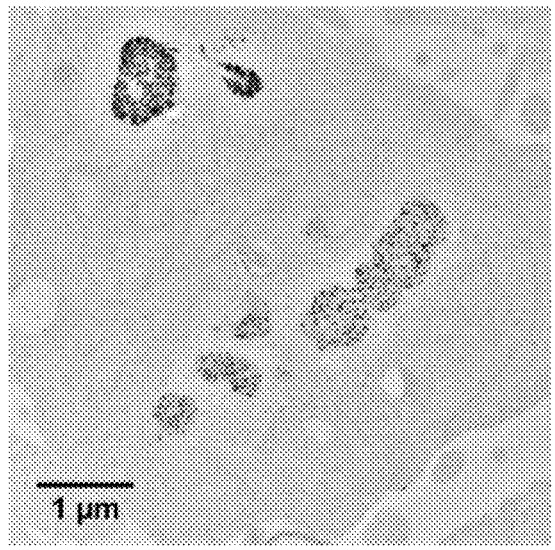
Figure 21C:
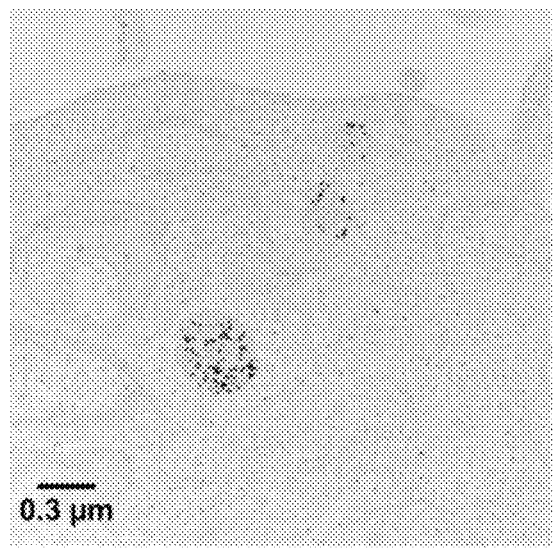
Figure 21D:
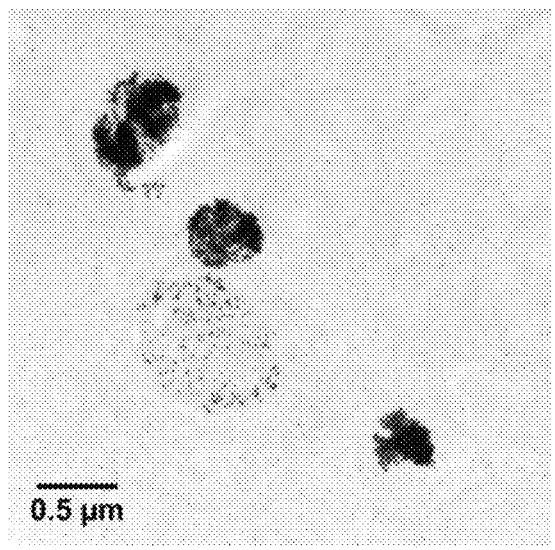

Cellular delivery studies were performed with MDA-MB-231 Cherry cells to evaluate the cell uptake and general biocompatibility of Lip-Gd@AuNPs. Cells were treated with various concentrations of Lip-DO3AGd@AuNPs and Lip-DTPAGd@AuNPs and incubated for 24 and 72 h at 37° C. The treated cells were harvested and counted through flow cytometry and Gd(III) quantified through ICP-MS to determine cell uptake in Gd(III) fmol per cell. Significant differences in the cell uptake of Gd(III) were observed between Lip-DO3AGd@AuNPs and Lip-DTPAGd@AuNPs. For 24 h incubation, the Lip-DO3AGd@AuNPs achieved approximately ten times greater Gd(III) uptake over Lip-DTPAGd@AuNPs with 9.0 and 0.9 fmol of Gd(III)/cell, respectively (FIG. 17). Similarly, 72 h incubation with Lip-DO3AGd@AuNPs and Lip-DTPAGd@AuNPs yields an overall increase in cell uptake of 20.0 and 2.0 fmol of Gd(III)/cell, respectively—a 10 times greater cell uptake of Lip-DO3AGd@AuNPs (FIG. 18). In addition, time-dependent uptake for the cellular delivery of Lip-Gd@AuNPs was performed with MDA-MB-231 Cherry cells. Cells were incubated with 50 μM of either Lip-DO3AGd@AuNP or Lip-DTPAGd@AuNP for 1, 2, 4, 8, and 24 hours at 37° C. For each time point, cells were harvested and subsequently counted and the Gd(III) content quantified. The similar ten-fold increase in cell uptake of Gd(III) between Lip-DO3AGd@AuNPs and Lip-DTPAGd@AuNPs was observed (FIG. 19). However, the uptake of Lip-DTPAGd@AuNPs did not appear to be time-dependent. Maximum cell uptake of Lip-DTPAGd@AuNPs was achieved within one hour. Conversely, the cell uptake of Lip-DO3AGd@AuNPs was time dependent. Significant increase in cell uptake of Lip-DO3AGd@AuNPs was observed between 8 and 24 h incubation, indicating uptake occurs concurrently with cell division.

To confirm AuNP uptake, cells incubated with Lip-DO3AGd@AuNPs and Lip-DTPAGd@AuNPs were prepared for TEM. The presence of both Lip-DO3AGd@AuNPs and Lip-DTPAGd@AuNPs were observed. In particular, Lip-DO3AGd@AuNPs appear in more abundance, relative to Lip-DTPAGd@AuNPs, and appear to undergo phagocytosis in large aggregate form. Furthermore, the phagosomes appear to merge together and sequester the AuNPs in a single, large vesicle (FIGS. 20A-D). In similar fashion, this behavior is observed for Lip-DTPAGd@AuNPs (FIGS. 21A-D). However, the abundance and size of vesicles containing AuNPs are decreased (as determined through empirical observation), relative to Lip-DO3AGd@AuNPs. This corresponds to the differences in cell uptake between Lip-DO3AGd@AuNPs and Lip-DTPAGd@AuNPs. These studies reveal Lip-Gd@AuNPs undergo a form of endocytosis (or phagocytosis) and accumulate inside the cell for Gd(III) cell labeling.

Example 4

Pancreatic Tissue Labeling for MRI with Gd(III)-Dithiolane Gold Nanoparticles—Materials/Methods Chemical Synthesis and Characterization Reagents and solvents were purchased from Sigma-Aldrich unless otherwise noted. Chemical synthesis was performed under ambient conditions unless described explicitly. Chemical characterization was achieved using a Varian 500 MHz NMR and a Bruker AutoFlex III MALDI spectrometer. Ligand and Gd(III) complex purification was performed using a Varian Prostar 500 HPLC using a Waters 4.6×250 mm 5 m Atlantis C18 column and mobile phases of Millipore water, 0.05% trifluoroacetic acid in Millipore water, and acetonitrile. Nanoparticle characterization was performed on JOEL 1230 and Hitachi HD7700 TEMs.

Synthesis of Lipoic NHS-Ester

To a 100 mL round bottom flask containing a magnetic stir bar and (±)-lipoic acid (0.500 g, 2.4 mmol) and N-hydroxysuccinimide (0.418 g, 3.6 mmol) was added 20 mL of chloroform. The mixture was stirred at room temperature until dissolution of the NHS, at which time is added N,N'-diisopropylcarbodiimmide (0.563 mL, 3.6 mmol) dropwise at room temperature. Complete formation of the coupled NHS ester was assessed by the appearance of product by TLC (Rf=0.4) in diethyl ether and was visualized by CAM stain. Purification of the product was achieved by silica gel chromatography using 100% diethyl ether. $^1$H NMR (500 MHz, Chloroform-d) δ 3.64-3.53 (m, 1H), 3.24-3.07 (m, 2H), 2.84 (s, 4H), 2.63 (t, J=7.3 Hz, 2H), 2.47 (q, J=12.3, 6.6 Hz, 1H), 1.92 (q, J=13.5, 6.9 Hz, 1H), 1.85-1.43 (m, 7H). $^{13}$C NMR (126 MHz, CDCl$_3$) δ 169.10, 168.40, 56.09, 40.15, 38.52, 34.42, 30.79, 28.32, 25.59, 24.37.

Synthesis of Lip-DO3AGd

To a 10 mL round bottom flask containing a magnetic stir bar is added Gd-DO3A-C6 amine (0.100 g, 0.17 mmol) and 1 mL of carbonate buffer pH 9.2. In a separate vial is added Lip-NHS (0.08 g, 0.20 mmol) and 2 mL DMSO. Upon complete dissolution of Lip-NHS, the solution is added to the stirring solution of Gd-DO3A-C6 amine at room temperature, and left to stir for 12 hours. Reaction completeness is monitored by ESI-MS for the disappearance of starting material at m/z 600.2 [M+H]$^+$. Purification of final product is achieved by semipreparative HPLC. The crude mixture injected directly, eluting via the use of the following method, where the mobile phase consists of Millipore water and HPLC grade acetonitrile (ACN): initial conditions of 0% ACN were held constant for 5 min, then ramped to 32% ACN between 5-17 min, followed by a gradual ramp to 40% ACN at 31 min. The product peak elutes between 23 and 26 minutes, as monitored by UV absorption at 210 nm. The product is collected, and lyophilized to a fluffy pale yellow solid. (m/z) observed: 811.0, calculated: 811.2 [M+Na]$^+$.

Synthesis of Lip-DTPAGd

Lip-DTPAGd is synthesized by an analogous procedure to Lip-GdDO3A. Specifically, a 10 mL round bottom flask is charged with a magnetic stir bar and Gd-DTPA-C4 amine (0.100 g, 0.16 mmol) and 1 mL of carbonate buffer pH 9.2. In a separate vial is added Lip-NHS (0.08 g, 0.20 mmol) and 2 mL DMSO. Upon complete dissolution of Lip-NHS, the solution is added to the stirring solution of Gd-DTPA-C4 amine at room temperature, and left to stir for 12 hours. Reaction completeness is monitored by ESI-MS for the disappearance of starting material at m/z 617.1 [M]−. Purification of final product is achieved by semipreparative HPLC. The crude mixture injected directly, eluting via the use of the following method, where the mobile phase consists of Millipore water and HPLC grade acetonitrile (ACN): initial conditions of 0% ACN were held constant for 5 min, then ramped to 5% ACN between 5-10 min, and held constant at 5% CAN until 20 min. Acetonitrile is then ramped to 100% through 25 min and held constant at 100% ACN until 30 min. The product peak elutes between 26.0 and 26.9 minutes, as monitored by UV absorption at 210 nm.

Relaxivity (r1)

A stock solution of Lip-DO3AGd@AuNP was made (700 uL). This stock was serially diluted four times for a total of five solutions. Solutions were heated to 37° C. and two hundred uL of each concentration was placed into a Bruker minispec mq60 NMR spectrometer (60 MHz) for measurement of $T_1$ relaxation time. Data were collected using an inversion recovery pulse sequence using 4 averages, a 15 s repetition time and 10 data points. The remaining volumes of each solution were utilized for ICP analysis of [Gd(III)]. The inverse of the longitudinal relaxation time ($1/T_1$, $s_{-1}$) was plotted versus the Gd(III) concentration (mM). By applying a linear fit to this data, the slope that is generated is defined as the relaxivity of the agent (mM$^{-1}$ s$^{-1}$). Relaxivitiy of Lip-DTPAGd@AuNP was collected by the analogous procedure.

Metals Analysis by ICP-MS

ICP-MS was performed on either a computer-controlled (Plasmalab software) Thermo (Thermo Fisher Scientific, Waltham, Mass.) PQ ExCell ICP-MS equipped with a CETAC 500 autosampler or a computer-controlled (Plasmalab software) Thermo X series II ICP-MS equipped with an ESI (Omaha, Nebr., USA) SC-2 autosampler.

Quantitation of metal concentration was performed by acid digestion of nanoconjugate samples, followed by ICP-MS analysis. Gadolinium and gold analyses were prepared by different dilution factors such that were within the range of the selected standard concentrations. Specifically, Gd analyses were digested by addition of 20 ul of nanoconjugate sample into 120 ul of 1:1 concentrated nitric acid: concentrated hydrochloric acid (TraceSelect Nitric acid, >69%; TraceSelect HCl, fuming 37%) and mixed thoroughly. Au analyses were made by addition of 5 uL of nanoconjugate sample to 500 uL of 1:1 HNO$_3$:HCl as above, and mixed thoroughly. Millipore water and multi-element internal standard (CLISS-1, Spex Certiprep, Metuchen, N.J., USA) containing 6Li, Sc, Y, In, Ho, Bi were added to produce a solution of 2% nitric acid (v/v), 2% HCl (v/v) and 5.0 ng/mL internal standard up to a total sample volume of 3 mL (Gd) and 10 mL (Au) after 20-fold dilution of original aliquot. Individual Au and Gd elemental standards were prepared at 0, 0.78125, 1.5625, 3.125, 6.25, 12.5, 25.0, 50.0, 100, and 200 ng/mL concentrations with 2% nitric acid (v/v), 2% HCl (v/v) and 5.0 ng/mL internal standards up to a total sample volume of 5 mL. Each sample was acquired using 1 survey run (10 sweeps) and 3 main (peak jumping) runs (100 sweeps). The isotopes selected were $^{197}$Au, $^{156, 157}$Gd and $^{115}$In, $^{165}$Ho, and $^{209}$Bi (as internal standards for data interpolation and machine stability).

High Field Relaxivity (7 T)

MR imaging and T1 measurements were performed on a Bruker Pharmscan 7 T imaging spectrometer fitted with shielded gradient coils at 25° C. Samples were prepared by serial dilution, and confirmation of concentration by ICP-MS for [Gd]. Solutions were imaged in glass capillary tubes of approximate diameter=1 mm.

Spin-lattice relaxation times (T1) were measured using a rapid-acquisition rapid-echo (RARE-VTR) T1-map pulse sequence, with static TE (11 ms) and variable TR (150, 250, 500, 750, 1000, 2000, 4000, 6000, 8000, and 10000 ms) values. Imaging parameters were as follows: field of view (FOV)=25×25 mm2, matrix size (MTX)=256×256, number of axial slices=4, slice thickness (SI)=1.0 mm, and averages (NEX)=3 (total scan time=2 h 36 min). T1 analysis was carried out using the image sequence analysis tool in Paravision 5.0 pl3 software (Bruker, Billerica, Mass., USA) with monoexponential curve-fitting of image intensities of selected regions of interest (ROIs) for each axial slice.

General Cell Culture

Dulbecco's modified phosphate buffered saline (DPBS), media, and dissociation reagents were purchased from Life Technologies (Carlsbad, Calif.). CorningBrand® cell culture consumables (flasks, plates, etc.) and sera were purchased from VWR Scientific (Radnor, Pa.). MDA-MB-231 Cherry (ATCC® HTB-26™) cells were purchased from the American Type Culture Collection (ATCC, Manassas, Va.) and cultured in phenol red-free minimum essential media (MEM) supplemented with 10% fetal bovine serum (FBS). Prior to all experiments, cells were plated and allowed to incubate for 24 hours before dosing. Cells were harvested with 0.25% TrypLE for 5 minutes at 37° C. in a 5.0% CO$_2$ incubator. For sterilization, all Gd(III)-labeled molecules were filtered with 0.2 µm sterile filters prior to concentration determination and storage at 4° C. GO was used as prepared without further sterilization. Cells were grown in a humidified incubator operating at 37° C. and 5.0% CO$_2$.

Guava ViaCount Assay for Cell Counting

Cell counting was conducted using a Guava EasyCyte Mini Personal Cell Analyzer (EMD Millipore, Billerica, Mass.). After cell harvesting, an aliquot (50 µL) of the cell suspensions was mixed with Guava ViaCount reagent (150 µL) and allowed to stain at room temperature for at least 5 minutes. The dilution factor of 4 was determined based upon optimum machine performance (20-150 cells/µL). After vortexing for 10 sec, stained cells were counted using a Guava EasyCyte Mini Personal Cell Analyzer (PCA) using the ViaCount software module. For each sample, 1000 events were acquired. Gating of live/dead and cell/debris classifications were performed manually by the operator. Instrument reproducibility was assessed biweekly using GuavaCheck Beads and following the manufacturer's suggested protocol using the Daily Check software module.

Cellular Delivery Studies

Cellular delivery studies were performed with MDA-MB-231 Cherry cells. MDA-MB-231 Cherry cells were plated at a cell density of approximately 25,000 and 10,000 cells per well for 24 and 72 hour uptake, respectively, in a 24-well plate as counted by a hemocytometer. Stock solutions of Lip-DO3AGd@AuNP and Lip-DTPAGd@AuNP (500 mM Gd) were prepared by diluting with media to give a final concentration of 80 µM Gd. This solution was serially diluted further with media to prepare incubating solutions of 180 µL per well. Cells were incubated with either Lip-DO3AGd@AuNP or Lip-DTPAGd@AuNP for 24 and 72 hours, respectively. Time-dependent uptake for cellular delivery studies were performed with MDA-MB-231 Cherry cells. MDA-MB-231 Cherry cells were plated at a cell density of approximately 37,000 cells per well in a 24-well plate as counted by a hemocytometer. Cells were incubated with 50 µM of either Lip-DO3AGd@AuNP or Lip-DTPAGd@AuNP for 1, 2, 4, 8, and 24 hours. To harvest, cells were rinsed in-plate three times with 500 µL PBS and trypsinized using 100 µL 0.25% TrypLE. Following trypsin treatment, 150 µL of media was added to each well and mixed by a pipette to ensure that all cells were lifted into suspension. 50 µL of the cell suspension was used for cell counting and 150 µL was used for Gd content analysis via ICP-MS.

Example 5

In Vivo Studies

Experiments conducted during development of embodiments herein demonstrate that dithiolane-Gd(III) gold nanoparticle nanoconjugates exhibit very high per particle values of r1 relaxivity at both low and high magnetic field strengths due to the high Gd(III) payload, and demonstrate pancreatic tissue labeling via MR images, post-mortem biodistribution analysis, and pancreatic tissue evaluation of particle localization. Significant contrast enhancement was observed allowing clear identification of the pancreas with contrast-to-noise ratios exceeding 35:1.

Mouse MRI

In vivo MR images (n=3) were acquired 24 h post injection of Lip-Gd@AuNPs on a 9.4 T Bruker Biospec (Bruker Biospin, Billerica, Mass., U.S.A.) using a 38 mm quadrature mouse body volume coil. For anatomical reference, T2 weighted accelerated spin echo (TurboRARE) images were acquired with TR/TE=570 ms/24 ms, RARE factor 8, field of view 4 cm×4 cm, matrix 256×256, 1 mm slice thickness, 7 slices, 0.3 mm slice gap, and 9 averages. To measure contrast enhancement, T1 weighted gradient echo FLASH images were acquired with TR/TE/α=100 ms/2.2 ms/45° and 2 averages. Slice geometry was identical to the T2 weighted images except for a matrix of 192×192. During imaging, mice were held under 1-2% inhaled isoflurane anesthesia and respiration was monitored using an SA Instruments MR compatible monitoring system (SA Instruments, Stonybrook, N.Y., U.S.A.). Images were processed using JIM 6 software (Xinapse Systems, Essex, United Kingdom). Contrast-to-noise ratio (CNR) maps were measured by placing a signal region of interest in leg skeletal muscle and the bladder, and a noise region in the corner of the image, subtracting muscle signal from each pixel in the image, and dividing by the standard deviation of the noise. For visualization, CNR maps were set to a threshold at a value of 35, a color lookup table was applied, and the map was overlaid on the T2 weighted anatomical reference image.

Figure 22:
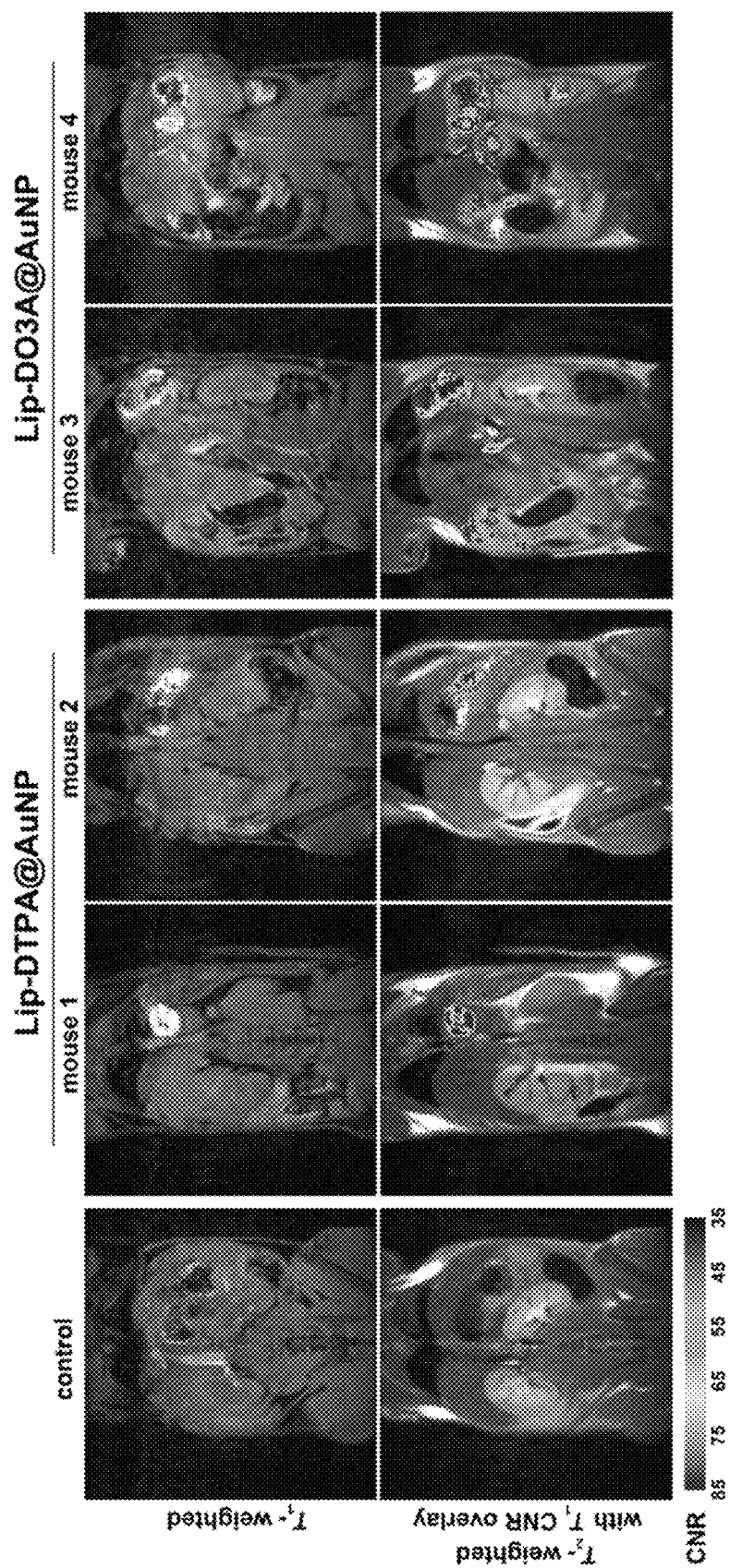
FIG. 22. T1-weighted FLASH images were obtained at 9.4 T to assess contrast of Lip-DTPA@AuNPs and Lip-DO3A@AuNPs. Contrast-to-noise ratio (CNR) relative to muscle, computed from T1-weighted FLASH images, were overlaid on TurboRARE T2-weighted anatomical images at 9.4 T after administration of Lip-DTPA@AuNPs, Lip-DO3A@AuNPs, and no agents (control) following 24 h incubation. Upon administration of both Lip-Gd@AuNP constructs, significant contrast enhancement is observed in the region of the pancreas.
Figure 24:
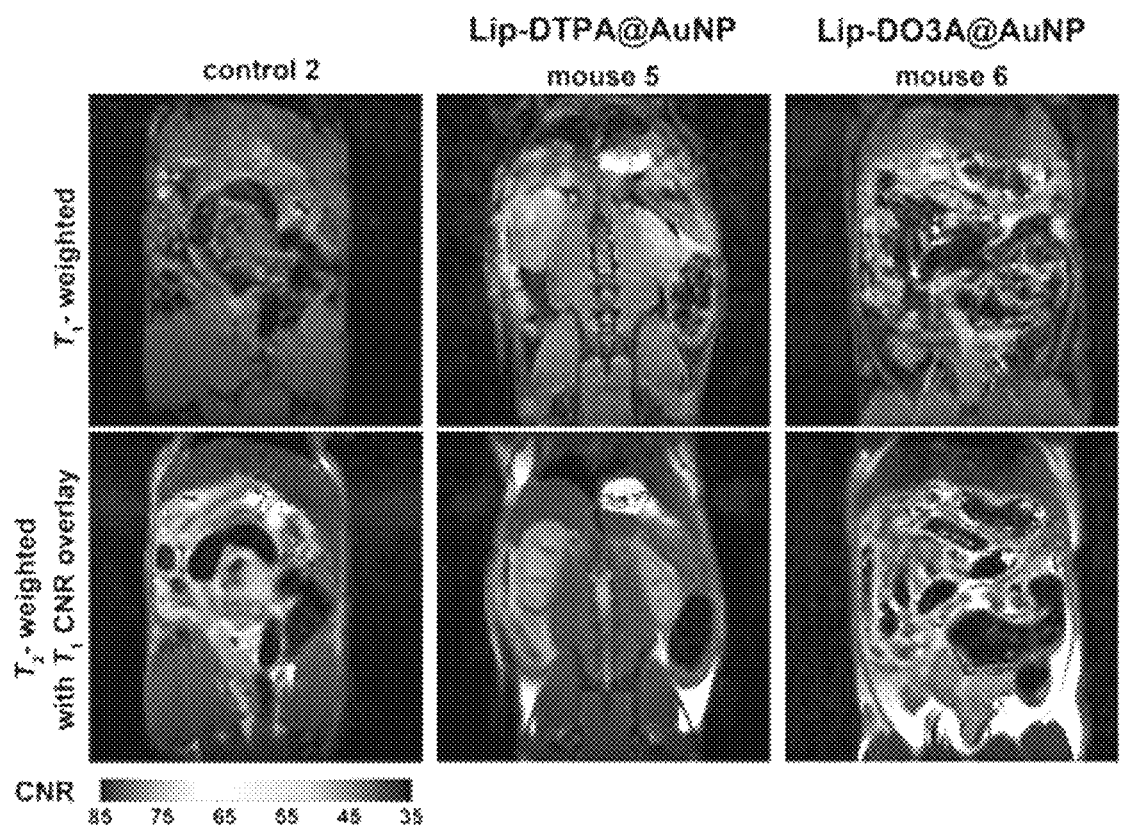
FIG. 24. T1-weighted FLASH images of Lip-DTPA@AuNPs and Lip-DO3A@AuNPs were obtained at 9.4 T. Contrast-to-noise ratio (CNR) relative to muscle, computed from T1-weighted FLASH images, were overlaid on TurboRARE T2-weighted anatomical images at 9.4 T after administration of Lip-DTPA@AuNPs, Lip-DO3A@AuNPs, and no agents (control) following 24 h incubation.
Figure 25:
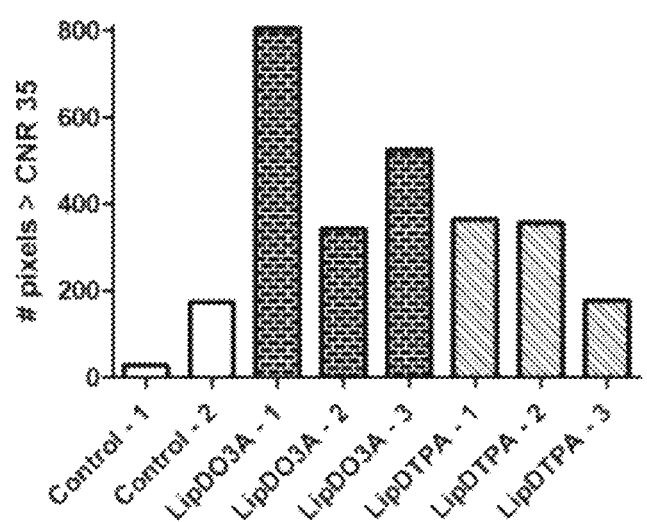
FIG. 25. Graph depicting number of pixels in pancreas ROI above CNR of 35 relative to muscle in each mouse tested. CNR maps were measured by placing a single region of interest around the pancreas, in leg skeletal muscle, the bladder, and a noise region in the corner of the image. The muscle signal was subtracted from each pixel in the pancreas ROI, and divided by the standard deviation of the noise. CNR maps were set to a threshold at a value of 35, and the number of pixels in the pancreas ROI of each mouse was counted.

In vivo imaging of animals incubated with Lip-Gd@AuNPs was conducted to measure enhanced MR image contrast in pancreatic tissue. In particular, pancreatic imaging in rodents can be challenging because the organ is not a well-defined solid retroperitoneal organ but rather a thin membrane spread throughout the upper abdomen and lying immediately adjacent to the gut. Furthermore, the low intrinsic T1-weighted contrast of the pancreas, motion artifacts, and intestinal gas makes MR detection of the pancreas notoriously difficult. In an effort to evaluate the performance of Gd(III)@AuNPs for pancreatic imaging, animals were injected with 4.0 nmol/kg body weight of AuNPs through ip administration. For Lip-DO3A@AuNPs, this equates to 8.8 µmol/kg body weight of Gd(III). For Lip-DTPA@AuNPs, this equates to 5.5 µmol/kg body weight of Gd(III). Following ip injection and 24 h incubation, MR images were acquired of the peritoneal cavity at 9.4 T (n=3 for Lip-DO3A@AuNP and Lip-DTPA@AuNP, respectively) using standard T1-weighted FLASH scans. Significantly increased contrast enhancement was observed for mice treated with Lip-Gd@AuNPs, allowing obvious identification of the pancreas, with high contrast-to-noise ratios (CNRs) in all subjects (FIG. 22). The muscle signal was subtracted from each pixel in the pancreas region of interest (ROI) and divided by the standard deviation of the noise to generate the CNR map. The resulting CNR maps were set to a threshold at a value of 35 and the number of pixels in the pancreas ROI of each mouse was counted (see FIGS. 24 and 25). The number of pixels with a CNR greater than 35 ranged from 343 to 805 for Lip-DO3A@AuNPs and from 178 to 364 for Lip-DTPA. Furthermore, the two control mice were observed to have 27 and 174 pixels with CNRs greater than 35. The marked increase in CNR of the T1-weighted images of mice dosed with Lip-Gd@AuNPs indicates the localization of particles within the pancreas and subsequent contrast enhancement.

Biodistribution Analysis

Figure 23A:
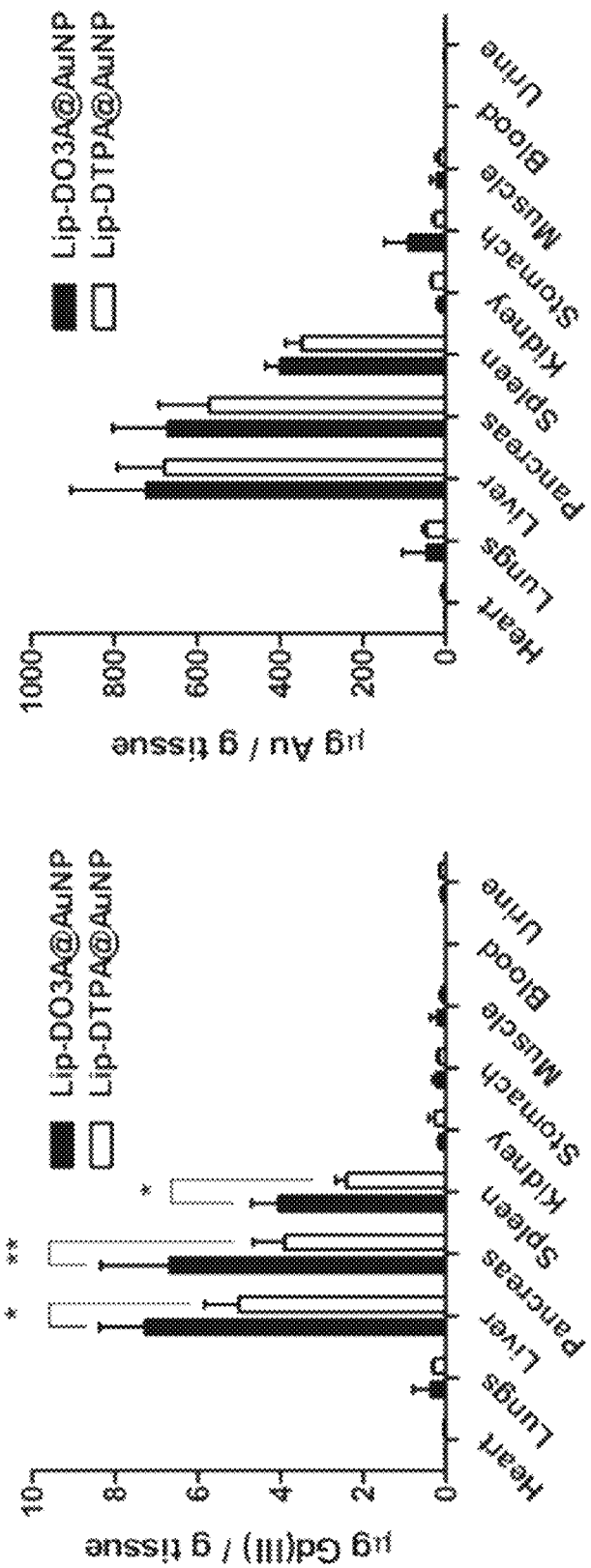
FIGS. 23A-C. (a) Biodistribution of Lip-DTPA@AuNPs and Lip-DO3A@AuNPs in C-57 mice. Following ip administration and 24 h incubation, organs were harvested and metal analysis was conducted via ICP-MS to determine the amount of Gd(III) and Au per gram of organ. Lip-Gd@AuNPs accumulate in the clearance organs, liver and spleen, and accumulates in the pancreas. Similar amounts of Au per gram of organ were observed for both Lip-DO3A@AuNP and Lip-DTPA@AuNP. However, Lip-DO3A@AuNP was observed to have a greater amount of Gd(III) per gram of organ, reflecting the higher Gd(III) loading onto the particle. Two-tailed t test: *$P<0.01$, **$P<0.05$. (b) TEM images of pancreatic tissue from mice treated with Lip-DTPA@AuNPs and Lip-DO3A@AuNPs. Particles are present (as black spheres) in a lysosome as particle aggregates (<1 μm) in the macrophage. The labeled cell is present in the interstitial spaces of acrine cells as identified by the extensive ER organelles (scale bars are 1 μm). (c) Histology reveals mild inflammatory foreign material reaction in the adjacent tissue of the pancreas. The low-magnification images (10×) show Lip-DTPA@AuNPs and Lip-DO3A@AuNPs labeled pancreatic tissue and the adjacent fatty tissues. No structural or morphological abnormalities were noted in either of the two pancreases. Under the high-power magnification (100×), black nanoparticles are diffusely distributed in the fatty and pancreatic tissue (black arrows) of both pancreas slices. The inflammatory cells include lymphocytes and histocytes, some with phagocytic nanoparticles (gray arrows) (scale bars are 100 μm).
Figure 23B:
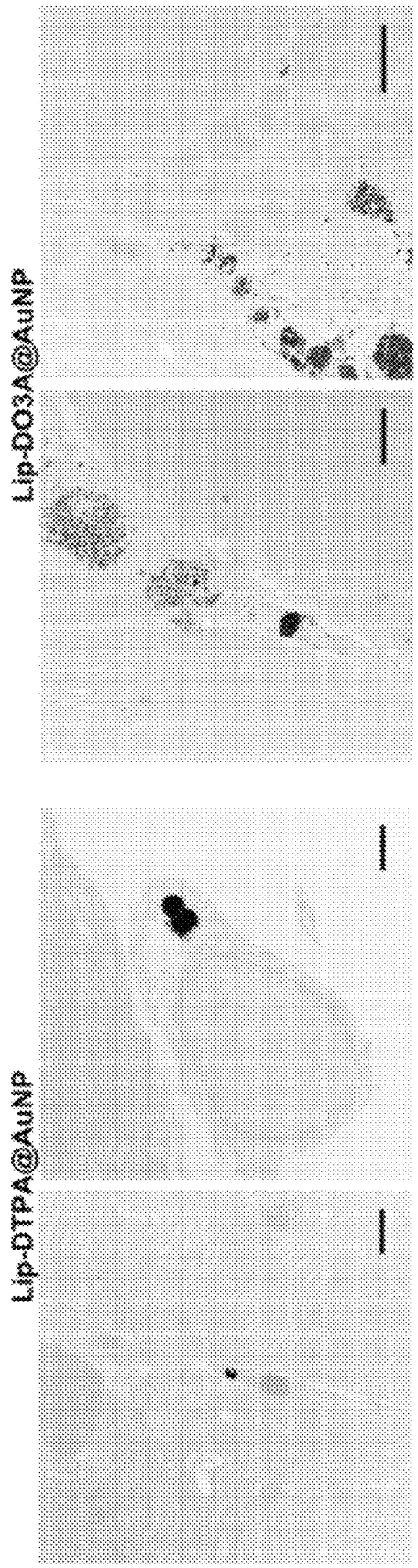
Figure 23C:
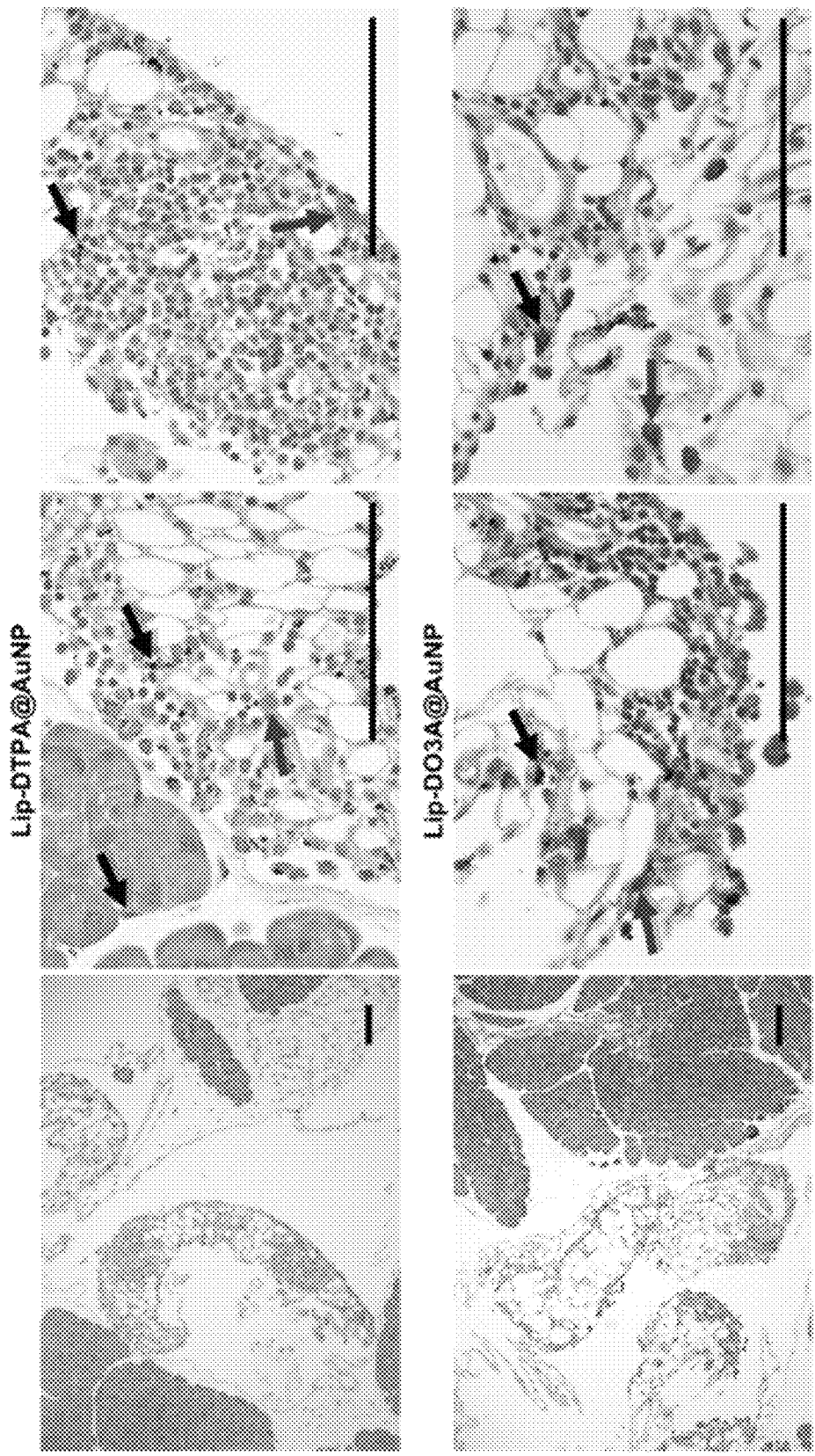

To investigate the performance observed in MR imaging, biodistribution of Lip-Gd@AuNPs was conducted. Animals were sacrificed and organs were harvested for quantification of Gd(III) and Au using ICP-MS (FIGS. 23A-C). Significant accumulation in the liver and spleen was observed (~700 and ~400 µg of Au per gram of tissue, respectively, for both Lip-DO3A@AuNPs and Lip-DTPA@AuNPs). The high levels of AuNPs found in the liver and spleen indicate that the reticuloendothelial system (RES) is the dominant mode of clearance for these particles. However, despite this high accumulation, no significant MR contrast enhancement is observed in these organs when compared to the pancreas. This phenomenon may be attributed to organ density and differences in contrast agent diffusion rates within the tissues. Significant localization to the pancreas was observed (~550 µg of Au per gram of tissue for both Lip-DO3A@AuNPs and Lip-Gd@AuNPs). Indeed, the levels of Gd(III) relative to Au in all tissues reflect the Gd(III) loading observed for Lip-DO3A@AuNPs and Lip-DTPA@AuNPs and not the differences in charge of the two chelates.

In an effort to validate the accumulation of Lip-Gd@AuNPs to the pancreas, TEM and histology of the pancreas were performed following 24 h incubation with Lip-DO3A@AuNPs and Lip-DTPA@AuNPs, respectively. Immediately following harvesting of the pancreas, the tissue was divided in two and fixed in formalin. The tissue was separately prepared for sectioning for TEM and histology. TEM images of pancreatic tissue slices revealed the presence of AuNPs in mice incubated with both Lip-Gd@AuNP constructs (FIGS. 2A-D). Significant presence of particles was observed to be encapsulated in large particle aggregates in lysosomes (~1 µm) of macrophages and located in the interstitial spaces between acinar cells of the pancreatic tissue. The identification of the acinar cells was based on the presence of extensive endoplasmic reticulum (ER) organelles because they are indicative of this particular pancreatic cell type.

Further confirmation of pancreatic tissue labeling by Lip-Gd@AuNPs was obtained through histological analysis. The presence of AuNP aggregates is observed in hematoxylin and eosin stained pancreatic tissue sections for animals incubated with Lip-DO3A@AuNPs and Lip-DTPA@AuNPs, respectively (FIG. 23). No structural and morphological abnormalities were noted in either of the two pancreases. However, slight inflammation was noted in the adjacent fatty tissues. Under high-power magnification (100×), black AuNP aggregates are diffusely distributed in the surrounding fatty tissue of the pancreas. The inflammatory cells include lymphocytes and histiocytes and nanoparticle-laden phagocytes. Furthermore, the tissue contained nanoparticle aggregates directly in the pancreatic tissue among acinar cells. It is contemplated that Lip-Gd@AuNPs (e.g., when delivered by ip administration) elicit an immune response that drives accumulation to the pancreas through sequestration by macrophages.

All publications and patents provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

REFERENCES

The following references are herein incorporated by reference in their entireties.
(1) Klein, A. P. Identifying people at a high risk of developing pancreatic cancer. Nat. Rev. Cancer 2012, 13, 66-74.
(2) Abbruzzese, J. The challenge of pancreatic cancer. Int. J. Gastrointest. Cancer 2003, 33, 1-2.
(3) Hidalgo, M.; Cascinu, S.; Kleeff, J.; Labianca, R.; Lo¨hr, J. M.; Neoptolemos, J.; Real, F. X.; Van Laethem, J.-L.; Heinemann, V. Addressing the challenges of pancreatic cancer: Future directions for improving outcomes. Pancreatology 2015, 15, 8-18.
(4) Dempsey, M. F.; Condon, B.; Hadley, D. M. MRI safety review. Seminars in Ultrasound, CT and MRI 2002, 23, 392-401.
(5) Shellock, F. G.; Spinazzi, A. MRI Safety Update 2008: Part 1, MRI Contrast Agents and Nephrogenic Systemic Fibrosis. AJR, Am. J. Roentgenol. 2008, 191, 1129-1139.
(6) Willinek, W. A.; Schild, H. H. Clinical advantages of 3.0 T MRI over 1.5 T. Eur. J. Radiol. 2008, 65, 2-14.
(7) Harrison, V. S. R.; Carney, C. E.; MacRenaris, K. W.; Waters, E. A.; Meade, T. J. Multimeric Near IR-MR Contrast Agent for Multimodal In Vivo Imaging. J. Am. Chem. Soc. 2015, 137, 9108.
(8) Strauch, R. C.; Mastarone, D. J.; Sukerkar, P. A.; Song, Y.; Ipsaro, J. J.; Meade, T. J. Reporter Protein-Targeted Probes for Magnetic Resonance Imaging. J. Am. Chem. Soc. 2011, 133, 16346-16349.
(9) Sukerkar, P. A.; MacRenaris, K. W.; Meade, T. J.; Burdette, J. E. A Steroid-Conjugated Magnetic Resonance Probe Enhances Contrast in Progesterone Receptor Expressing Organs and Tumors in Vivo. Mol. Pharmaceutics 2011, 8, 1390-1400.
(10) Hung, A. H.; Holbrook, R. J.; Rotz, M. W.; Glasscock, C. J.; Mansukhani, N. D.; MacRenaris, K. W.; Manus, L. M.; Duch, M. C.; Dam, K. T.; Hersam, M. C.; Meade, T. J. Graphene Oxide Enhances Cellular Delivery of Hydrophilic Small Molecules by Co-incubation. ACS Nano 2014, 8, 10168-10177.
(11) Jensen, S. A.; Day, E. S.; Ko, C. H.; Hurley, L. A.; Luciano, J. P.; Kouri, F. M.; Merkel, T. J.; Luthi, A. J.; Patel, P. C.; Cutler, J. I.; Daniel, W. L.; Scott, A. W.; Rotz, M. W.; Meade, T. J.; Giljohann, D. A.; Mirkin, C. A.; Stegh, A. H. Spherical Nucleic Acid Nanoparticle Conjugates as an RNAi-Based Therapy for Glioblastoma. Sci. Transl. Med. 2013, 5, 209ra152.
(12) Rotz, M. W.; Culver, K. S. B.; Parigi, G.; MacRenaris, K. W.; Luchinat, C.; Odom, T. W.; Meade, T. J. High Relaxivity Gd(III)-DNA Gold Nanostars: Investigation of Shape Effects on Proton Relaxation. ACS Nano 2015, 9, 3385-3396.
(13) Song, Y.; Xu, X.; MacRenaris, K. W.; Zhang, X.-Q.; Mirkin, C. A.; Meade, T. J. Multimodal Gadolinium-Enriched DNA-Gold Nanoparticle Conjugates for Cellular Imaging. Angew. Chem., Int. Ed. 2009, 48, 9143-9147.
(14) Alric, C.; Taleb, J.; Duc, G. L.; Mandon, C.; Billotey, C.; Meur-Herland, A. L.; Brochard, T.; Vocanson, F.; Janier, M.; Perriat, P.; Roux, S.; Tillement, O. Gadolinium Chelate Coated Gold Nanoparticles As Contrast Agents for Both X-ray Computed Tomography and Magnetic Resonance Imaging. J. Am. Chem. Soc. 2008, 130, 5908-5915.
(15) Park, J.-A.; Reddy, P. A. N.; Kim, H.-K.; Kim, I.-S.; Kim, G.-C.; Chang, Y.; Kim, T.-J. Gold nanoparticles functionalised by Gd complex of DTPA-bis(amide) conjugate of glutathione as an MRI contrast agent. Bioorg. Med. Chem. Lett. 2008, 18, 6135-6137.
(16) Sung, S.; Holmes, H.; Wainwright, L.; Toscani, A.; Stasiuk, G. J.; White, A. J. P.; Bell, J. D.; Wilton-Ely, J. D. E. T. Multimetallic Complexes and Functionalized Gold Nanoparticles Based on a Combination of d- and f-Elements. Inorg. Chem. 2014, 53, 1989-2005.
(17) Irure, A.; Marradi, M.; Arnaiz, B.; Genicio, N.; Padro, D.; Penades, S. Sugar/gadolinium-loaded gold nanoparticles for labelling and imaging cells by magnetic resonance imaging. Biomater. Sci. 2013, 1, 658-668.
(18) Ferreira, M. F.; Goncalves, J.; Mousavi, B.; Prata, M. I. M.; Rodrigues, S. P. J.; Calle, D.; Lopez-Larrubia, P.; Cerdan, S.; Rodrigues, T. B.; Ferreira, P. M.; Helm, L.; Martins, J. A.; Geraldes, C. F. G. C. Gold nanoparticles functionalised with fast water exchanging Gd3+ chelates: linker effects on the relaxivity. Dalton Transactions 2015, 44, 4016-4031.
(19) Lewis, D. J.; Pikramenou, Z. Lanthanide-coated gold nanoparticles for biomedical applications. Coord. Chem. Rev. 2014, 273-274, 213-225.
(20) Zeng, Y.; Zhang, D.; Wu, M.; Liu, Y.; Zhang, X.; Li, L.; Li, Z.; Han, X.; Wei, X.; Liu, X. Lipid-AuNPs@PDA Nanohybrid for MRI/CT Imaging and Photothermal Therapy of Hepatocellular Carcinoma. ACS Appl. Mater. Interfaces 2014, 6, 14266-14277.
(21) Arvizo, R. R.; Miranda, O. R.; Moyano, D. F.; Walden, C. A.; Giri, K.; Bhattacharya, R.; Robertson, J. D.; Rotello, V. M.; Reid, J. M.; Mukherjee, P. Modulating Pharmacokinetics, Tumor Uptake and Biodistribution by Engineered Nanoparticles. PLoS One 2011, 6, e24374.

(22) Hung, A. H.; Duch, M. C.; Parigi, G.; Rotz, M. W.; Manus, L. M.; Mastarone, D. J.; Dam, K. T.; Gits, C. C.; MacRenaris, K. W.; Luchinat, C.; Hersam, M. C.; Meade, T. J. Mechanisms of Gadographene-Mediated Proton Spin Relaxation. J. Phys. Chem. C 2013, 117, 16263-16273.

(23) Burda, C.; Chen, X.; Narayanan, R.; El-Sayed, M. A. Chemistry and Properties of Nanocrystals of Different Shapes. Chem. Rev. 2005, 105, 1025-1102.

(24) Grimm, J.; Potthast, A.; Wunder, A.; Moore, A. Magnetic resonance imaging of the pancreas and pancreatic tumors in a mouse orthotopic model of human cancer. Int. J. Cancer 2003, 106, 806-811.

(25) Lasagna-Reeves, C.; Gonzalez-Romero, D.; Barria, M. A.; Olmedo, I.; Clos, A.; Sadagopa Ramanujam, V. M.; Urayama, A.; Vergara, L.; Kogan, M. J.; Soto, C. Bioaccumulation and toxicity of gold nanoparticles after repeated administration in mice. Biochem. Biophys. Res. Commun. 2010, 393, 649-655.

(26) Sadauskas, E.; Wallin, H.; Stoltenberg, M.; Vogel, U.; Doering, P.; Larsen, A.; Danscher, G. Kupffer cells are central in the removal of nanoparticles from the organism. Part. Fibre Toxicol. 2007, 4, 10.

(27) Koh, D.-M.; Collins, D. J. Diffusion-Weighted MRI in the Body: Applications and Challenges in Oncology. AJR, Am. J. Roentgenol. 2007, 188, 1622-1635.

(28) Patra, C. R.; Bhattacharya, R.; Mukhopadhyay, D.; Mukherjee, P. Fabrication of gold nanoparticles for targeted therapy in pancreatic cancer. Adv. Drug Delivery Rev. 2010, 62, 346-61.

(29) Patra, C. R.; Bhattacharya, R.; Wang, E.; Katarya, A.; Lau, J. S.; Dutta, S.; Muders, M.; Wang, S.; Buhrow, S. A.; Safgren, S. L.; Yaszemski, M. J.; Reid, J. M.; Ames, M. M.; Mukherjee, P.; Mukhopadhyay, D. Targeted delivery of gemcitabine to pancreatic adenocarcinoma using cetuximab as a targeting agent. Cancer Res. 2008, 68, 1970-8.

(30) Bellingan, G. J.; Xu, P.; Cooksley, H.; Cauldwell, H.; Shock, A.; Bottoms, S.; Haslett, C.; Mutsaers, S. E.; Laurent, G. J. Adhesion Molecule-dependent Mechanisms Regulate the Rate of Macrophage Clearance During the Resolution of Peritoneal Inflammation. J. Exp. Med. 2002, 196, 1515-1521.

(31) Miller, F. H.; Rini, N. J.; Keppke, A. L. MRI of adenocarcinoma of the pancreas. AJR, Am. J. Roentgenol. 2006, 187, W365-74.

(32) Tummala, P.; Junaidi, O.; Agarwal, B. Imaging of pancreatic cancer: An overview. J. Gastrointest. Oncol. 2011, 2, 168-74.

(33) Lee, G. Y.; Qian, W. P.; Wang, L.; Wang, Y. A.; Staley, C. A.; Satpathy, M.; Nie, S.; Mao, H.; Yang, L. Theranostic nanoparticles with controlled release of gemcitabine for targeted therapy and MRI of pancreatic cancer. ACS Nano 2013, 7, 2078-89.

(34) Torres, G. M.; Erquiaga, E.; Ros, P. R.; Burton, S. S.; Barreda, R.; Langmo, L. S.; Kennedy, S. J. Preliminary results of MR imaging with superparamagnetic iron oxide in pancreatic and retroperitoneal disorders. Radiographics: a review publication of the Radiological Society of North America, Inc 1991, 11, 785-91 discussion 792-3.

(35) Botsikas, D.; Terraz, S.; Vinet, L.; Lamprianou, S.; Becker, C. D.; Bosco, D.; Meda, P.; Montet, X. Pancreatic magnetic resonance imaging after manganese injection distinguishes type 2 diabetic and normoglycemic patients. Islets 2012, 4, 243-8.

(36) Diehl, S. J.; Lehmann, K. J.; Gaa, J.; McGill, S.; Hoffmann, V.; Georgi, M. MR imaging of pancreatic lesions. Comparison of manganese-DPDP and gadolinium chelate. Invest. Radiol. 1999, 34, 589-95.

(37) Schima, W. MRI of the pancreas: tumours and tumour-simulating processes. Cancer Imaging 2006, 6, 199-203.

(38) Birchard, K. R.; Semelka, R. C.; Hyslop, W. B.; Brown, A.; Armao, D.; Firat, Z.; Vaidean, G. Suspected pancreatic cancer: evaluation by dynamic gadolinium-enhanced 3D gradient-echo MRI. AJR, Am. J. Roentgenol. 2005, 185, 700-3.

The invention claimed is:

1. A method of observing a cell, tissue, and/or organ of a subject comprising:
   (a) administering to a subject a chelated metal-ion contrast agent conjugated to a gold nanoparticle by a dithiolane linkage, wherein the metal ion is selected from the group consisting of Mn(II), Gd(III), Dy(III), Ho(III), Er(III), Eu(III), Tb(III), Sm(III), Ce(III), Pr(III), Yb(III), Tm(III), Nd(III) and Tb(IV); wherein the metal ion is chelated by a chelation moiety comprising EDTA, DTPA, TTHA, DOTA, TAGA, DOTP, DTPA-BMA, DO2P or DO3A; wherein a linker moiety between the chelated metal-ion contrast agent and the dithiolane linkage comprises $(CH_2)_4COHN(CH_2)_y$, wherein y is 4 or 6, and
   (b) imaging the cell, tissue, and/or organ by magnetic resonance imaging.

2. The method of claim 1 wherein the cell, tissue, and/or organ comprises the pancreas of a subject.

3. The method of claim 2, wherein the composition is administered systemically.

4. The method of claim 2, wherein the composition is administered to the peritoneum.

5. The method of claim 2, wherein the composition is administered to the pancreas.

6. The method of claim 1, wherein the metal ion is Gd(III).

7. The method of claim 1, wherein the chelation moiety comprises DO3A.

8. The method of claim 1, wherein the chelation moiety comprises DTPA.

9. The method of claim 1, wherein the dithiolane linkage is the reaction product of a dithiolane functional group and the gold nanoparticle, and comprises two bonds between the sulfurs of the dithiolane functional group and the gold nanoparticle.

10. The method of claim 1, wherein the linker moiety further comprises an alkyl chain, heteroalkyl chain, substituted alkyl chain, or substituted heteroalkyl chain.

11. The method of claim 1, wherein the linker moiety comprises $(CH_2)_4CONH(CH_2)_6$.

12. The method of claim 1, wherein the linker further comprises a 1,2,3-triazole.

13. The method of claim 12, wherein the linker comprises the reaction product of an azide and an alkyne.

14. The method of claim 1, wherein the composition does not comprise nucleic acid.

\* \* \* \* \*